United States Patent
Grantcharov et al.

(10) Patent No.: US 12,051,500 B2
(45) Date of Patent: *Jul. 30, 2024

(54) OPERATING ROOM BLACK-BOX DEVICE, SYSTEM, METHOD AND COMPUTER READABLE MEDIUM FOR EVENT AND ERROR PREDICTION

(71) Applicant: SURGICAL SAFETY TECHNOLOGIES INC., Toronto (CA)

(72) Inventors: Teodor Pantchev Grantcharov, Stouffville (CA); Kevin Lee Yang, Mississauga (CA)

(73) Assignee: SST CANADA INC., Toronto (CA)

( * ) Notice: Subject to any disclaimer, the term of this patent is extended or adjusted under 35 U.S.C. 154(b) by 22 days.

This patent is subject to a terminal disclaimer.

(21) Appl. No.: 17/734,834

(22) Filed: May 2, 2022

(65) Prior Publication Data

US 2022/0270750 A1 Aug. 25, 2022

Related U.S. Application Data

(63) Continuation of application No. 15/561,877, filed as application No. PCT/CA2016/000081 on Mar. 24, 2016, now Pat. No. 11,322,248.

(Continued)

(30) Foreign Application Priority Data

Sep. 23, 2015 (WO) ................ PCT/CA2015/000504

(51) Int. Cl.
*G16H 40/20* (2018.01)
*A61B 5/00* (2006.01)
(Continued)

(52) U.S. Cl.
CPC ........... *G16H 40/20* (2018.01); *A61B 5/0022* (2013.01); *G06F 1/12* (2013.01); *G06F 17/40* (2013.01);
(Continued)

(58) Field of Classification Search
CPC ........ G16H 40/20; G16H 30/20; G16H 40/63; G16H 50/50; G16H 20/40; G16H 40/67;
(Continued)

(56) References Cited

U.S. PATENT DOCUMENTS

2020/0258616 A1* 8/2020 Likosky ............... H04N 21/439

FOREIGN PATENT DOCUMENTS

WO  WO-2015179778 A1 * 11/2015 ............... G06F 9/50
WO  WO-2022256931 A1 * 12/2022 ............. A61B 34/10

OTHER PUBLICATIONS

Machine Learning and Artificial Intelligence in Surgical Fields, Springer Link, by Melissa Egert, James E. Steward & Chandra P. Sundaram, Published Jul. 15, 2020, vol. 11, pp. 573-577 (Year: 2020).*

(Continued)

*Primary Examiner* — Mamon Obeid
*Assistant Examiner* — Teresa S Williams
(74) *Attorney, Agent, or Firm* — Norton Rose Fulbright Canada LLP

(57) ABSTRACT

A multi-channel recorder/encoder for collecting, integrating, synchronizing and recording medical or surgical data received as independent live or real-time data streams from a plurality of hardware units. The medical or surgical data relating to a live or real-time medical procedure. Example hardware units include a control interface, cameras, sensors, audio devices, and patient monitoring hardware. Further example systems may include a cloud based platform incorporating the encoder.

20 Claims, 28 Drawing Sheets

Related U.S. Application Data

(60) Provisional application No. 62/138,647, filed on Mar. 26, 2015.

(51) Int. Cl.
*G06F 1/12* (2006.01)
*G06F 17/40* (2006.01)
*G06N 20/00* (2019.01)
*G16H 20/40* (2018.01)
*G16H 30/20* (2018.01)
*G16H 40/63* (2018.01)
*G16H 40/67* (2018.01)
*G16H 50/50* (2018.01)
*H04L 9/40* (2022.01)

(52) U.S. Cl.
CPC ............. *G06N 20/00* (2019.01); *G16H 20/40* (2018.01); *G16H 30/20* (2018.01); *G16H 40/63* (2018.01); *G16H 40/67* (2018.01); *G16H 50/50* (2018.01); *H04L 63/0421* (2013.01)

(58) Field of Classification Search
CPC ......... A61B 5/0022; G06F 1/12; G06F 17/40; H04L 63/0421; G06N 20/00
USPC .......................................................... 705/2
See application file for complete search history.

(56) References Cited

OTHER PUBLICATIONS

Canadian Intellectual Property Office (CIPO), Examiner's Requisition issue to CA Application 2,980,618 dated Apr. 4, 2022.

\* cited by examiner

FIG. 25

OPERATING ROOM BLACK-BOX DEVICE, SYSTEM, METHOD AND COMPUTER READABLE MEDIUM FOR EVENT AND ERROR PREDICTION

CROSS REFERENCE TO RELATED APPLICATIONS

This application is a Continuation of U.S. application Ser. No. 15/561,877 filed Sep. 26, 2017, which is a 371 US National Stage Application of PCT Application No. PCT/CA2016/000081 filed on Mar. 24, 2016, which claims priority, including benefit, to U.S. Provisional Application No. 62/138,647 entitled "OPERATING ROOM BLACK-BOX DEVICE, SYSTEM, METHOD AND COMPUTER READABLE MEDIUM", and filed Mar. 26, 2015; and International (PCT) Patent Application No. PCT/CA2015/000504, entitled "OPERATING ROOM BLACK-BOX DEVICE, SYSTEM, METHOD AND COMPUTER READABLE MEDIUM", and filed Sep. 23, 2015, the entire contents of each of which is hereby incorporated by reference.

FIELD

Embodiments described herein relate generally to the field of medical devices, systems and methods and, more particularly, to a medical or surgical black-box device, system, method and computer readable medium.

BACKGROUND

Prior attempts to implement data collection in a live operating room (OR) setting or patient intervention area may not have been successful. Example reasons may include: (1.) Data collection may be not comprehensive enough. Previous attempts included a very limited number of inputs, which may have resulted in a failure to identify chains of events leading to adverse outcomes, and/or a failure to validate offering quality improvement benefits. (2.) A lack of synchronization. Prior attempts did not achieve requisite synchronization to record multiple video-audio feeds. (3.) Rigorous data analysis methods were not applied. Prior attempts used metrics in isolation. The attempts did not have ability to analyze multiple aspects of surgery simultaneously—e.g., technical performance, non-technical skill, human factors, workflow, occupational safety, communication, etc. and, (4.) The value of the analysis may not have been adequately demonstrated. These are examples only.

BRIEF DESCRIPTION OF THE DRAWINGS

In the Figures,

FIG. 25 is a timeline chart illustrative of some results where the system was able to identify potential errors in relation to actual technical errors and/or technical events, according to some embodiments.

SUMMARY

Figure 1:
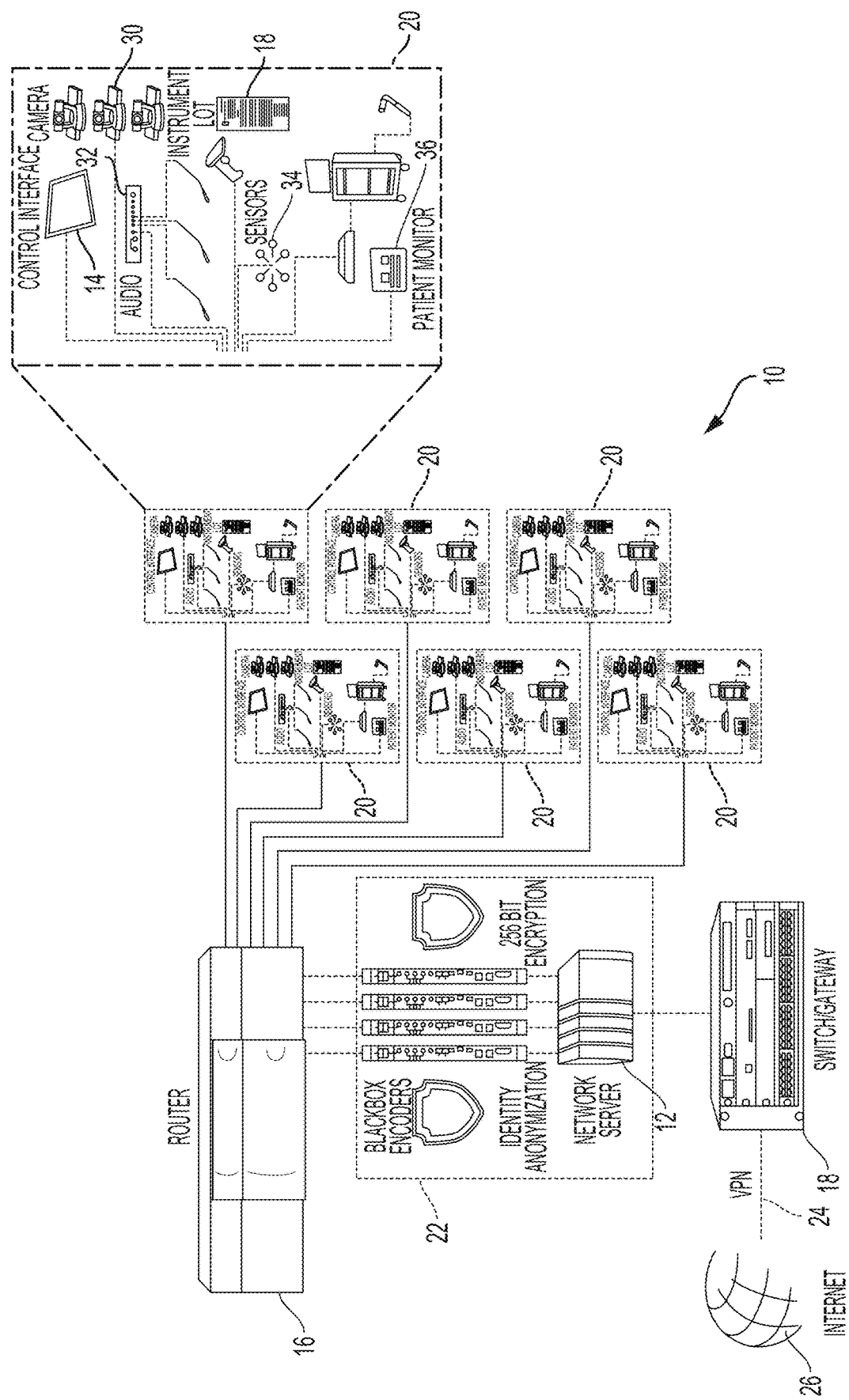
FIG. 1 illustrates a schematic of an architectural platform according to some embodiments.

In an aspect, there is provided a system for collecting and processing medical or surgical data. The system has a plurality of hardware units for collecting real-time medical or surgical data streams having a control interface coupled by a network to cameras, sensors, audio devices, and patient monitoring hardware, the real-time medical or surgical data streams relating to a real-time medical procedure within an operating or clinical site. The system has an encoder with a network server for synchronizing and recording the real-time medical or surgical data streams to a common clock or timeline to generate a session container file. The network server configured to control a multi-nodal perception engine to: generate a protocol for data extraction from the session container file; process the data using the protocol to extract patterns for time-stamped clinical events within the session container file, each time-stamped clinical event associated with a confidence level; generate an interface indicator for a temporal sequence of the time-stamped clinical events within the session container file and error assessments, the interface indicator identifying each of the time-stamped clinical events and the associated confidence levels; generate a predictive data model for refining protocol generation using support vector machines or artificial intelligence network data structures with neural networks for modelling correlation of data for interference and feature extraction.

In some embodiments, the device middleware and hardware to establishes a secure reliable connection using a network infrastructure for communication with the encoder and the hardware units, the device middleware and hardware for translating, connecting, and formatting the real-time medical or surgical data streams received independently from the hardware units.

In some embodiments, the device middleware and hardware implements data conformity and accurate synchronization for the real-time medical or surgical data streams using network protocols for clock synchronization between the hardware units to assist the encoder to generate the session container file.

In some embodiments, the encoder and device middleware and hardware are operable to interface with third party devices to receive additional data feeds as part of the real-time medical or surgical data streams.

In some embodiments, a central control station accessible using the control interface, the control station configured to control processing of the data streams in response to input control comprising play/pause, stop session, record session, move to session frame, split-display, recording status indicator, and log file.

In some embodiments, network infrastructure provides increased fail-over and redundancy for the real-time medical or surgical data streams from the hardware units.

In some embodiments, a storage area network for storing data container files of the real-time medical or surgical data streams until scheduled transmission.

In some embodiments, the encoder implements identity anonymization and encryption to the medical or surgical data.

In some embodiments, the encoder processes the real-time medical or surgical data streams to generate measurement metrics relating to the medical procedure.

In some embodiments, the real-time medical or surgical data streams correlates to a timeline, wherein the encoder detects events within the real-time medical or surgical data streams at corresponding times on the timeline, and tags and timestamps the session container file with the events, the timestamps corresponding to times on the timeline.

In some embodiments, an intelligent dashboard interface for annotation and tagging of the synchronized medical or surgical data streams, wherein the intelligent dashboard may implement a viewer with playback viewing for reviewing content and interface controls for tagging content.

In some embodiments, the intelligent dashboard is multi-dimensional in that the union of all dimension variables for the medical procedure may indicate a specific set of one or more applicable annotation dictionaries or coding templates.

In some embodiments, example variables that may be used to determine the annotation and tagging dictionary may be: the type of medical procedure being performed, the aspect of the procedure that is being analyzed, the geographic area/region where the procedure is being performed.

In another aspect, there is provided a multi-channel encoder for collecting, integrating, synchronizing and recording medical or surgical data streams onto a single interface with a common timeline or clock, the medical or surgical data streams received as independent real-time or live data streams from a plurality of hardware units, the encoder having a network server for scheduling transmission of session file containers for the recordings, the encoder processing the medical or surgical data streams to generate measurement metrics relating to a real-time medical procedure, the encoder configured to generate a protocol for data extraction from the session container file; process the data using the protocol to define patterns for time-stamped clinical events within the session container file; generate an interface indicator for a visual sequence of the time-stamped clinical events within the session container file and correspondence assessments; generate a predictive data model for refining protocol generation using support vector machines or artificial intelligence network data structures.

In some embodiments, the encoder generates as output a single session transport file using lossless compression operations.

The encoder detects completion of a recording of the data streams and securely encrypts the single transport file.

In some embodiments, the encoder implements identity anonymization to the medical or surgical data.

In some embodiments, the data streams comprising audio, video, text, metadata, quantitative, semi-quantitative, and data feeds.

In another aspect, there is provided a method for collecting and processing medical or surgical data comprising: receiving, at a multi-channel encoder, a plurality of live or real-time independent input feeds from one or more data capture devices located in an operating room or other patient intervention area, the input feeds relating to a live or real-time medical procedure; synchronizing, by the encoder, the plurality of live independent input feeds onto a single interface with a common timeline or clock; recording the synchronized input feeds using a network server; generating, by the encoder, an output session file using the synchronized input feeds; transmitting the output session file using the network server; generating a protocol for data extraction from the session container file; processing the data using the protocol to define patterns for time-stamped clinical events within the session container file; generating an interface indicator for a visual sequence of the time-stamped clinical events within the session container file and correspondence assessments; and generating a predictive data model for refining protocol generation using support vector machines or artificial intelligence network data structures.

In some embodiments, the method may involve processing the data streams for identity anonymization.

In some embodiments, the method may involve routing the data streams using a switch router to the encoder.

In another aspect, there is provided a cloud based system for collecting and processing medical or surgical data comprising: an encoder having a control interface for, in response to receiving a control command, triggering collection of real-time medical or surgical data streams by smart devices including cameras, sensors, audio devices, and patient monitoring hardware, the medical or surgical data relating to a real-time medical procedure within an operating or clinical site, the encoder for authenticating the smart devices, the smart devices synchronizing the real-time medical or surgical data streams by embedding timestamp markers within the real-time medical or surgical data streams, the timestamp markers generated by each smart device by a device clock; a media management hub server with middleware and hardware for translating, connecting, formatting, and recording the real-time medical or surgical data streams to generate session container files on network accessible storage devices; wireless network infrastructure to provide a secure network connection between the encoder, the smart devices and the media management hub server for communication of the real-time medical or surgical data streams; a central content server for storing and distributing the session container files and providing a two-way communication interface for the media management hub to implement a file transfer handshake for the session container files. The central content server is configured to: generate a protocol for data extraction from the session container file; process the data using the protocol to define patterns for time-stamped clinical events within the session container file; generate an interface indicator for a visual sequence of the time-stamped clinical events within the session container file and correspondence assessments; generate a predictive data model for refining protocol generation using support vector machines or artificial intelligence network data structures; and switching or gateway hardware to transmit the session container files from the media management hub to the central content server.

In some embodiments, the media management hub server broadcasts clock data to the smart devices for synchronization of the device clocks.

In some embodiments, the encoder provides a user interface to receive the control command and display real-time visual representations of the medical or surgical data.

In some embodiments, the media management hub server aggregates, packages, compresses and encrypts the real-time data streams to generate the session container files.

In some embodiments, the media management hub server manages the smart devices based on location, schedule, zone and requirements.

In some embodiments, the media management hub server receives operating status data from the smart devices to generate a management interface with a visual representation of the operating status data for the smart devices, the operating status data including online, offline, running capture, and on-board storage.

In some embodiments, the media management hub server processes the operating status data to detect smart devices operating outside of normal conditions and in response generating an alert notification of the detected smart devices operating outside of normal conditions.

In some embodiments, the media management hub server implements a device communication interface for the smart devices to implement a device data transfer handshake for the real-time medical or surgical data streams.

In some embodiments, the media management hub server authenticates the smart devices.

In another aspect there is provided a computational intelligence platform for receiving the session container files to construct an analytics model to identify clinical factors within the session container files for predictions, costs and safety hazards, the analytics model providing a network for extracting features, correlations and event behaviour from the session container files that involve multivariable data sets with time-variant parameters.

In some embodiments, a training or education server may receive the session container files, process the session container files to identify root causes of adverse patient outcomes and generate a training interface to communicate training data using the identified root causes and the session container files.

In some embodiments, the smart devices include motion tracking devices for markerless motion tracking of objects within the operating or clinical site, the system further comprising a processor configured to convert captured motion data from the motion tracking devices into data structures identifying human factors, workflow design and chain-of-events.

In some embodiments, the time-stamped clinical events within the session container file is stored with associated metadata for duration and frequency of each time-stamped clinical event.

In some embodiments, the network server or encoder uses patterns for time-stamped clinical events within the session container file to identify and extract features from the session container file for correlation or spectral analysis based on temporal nature of the time-stamped clinical events within the session container file.

In some embodiments, the network server or encoder identifies frequent temporal events as patterns leading to adverse events or errors in the timeline and develops predictive models to identify critical events during the real-time medical procedures.

In some embodiments, the network server or encoder groups the time-stamped clinical events within the session container file into technical and non-technical events.

In some embodiments, the interface indicator comprises an audio representation of the sequence of the time-stamped clinical events. In some embodiments, the interface indicator comprises a video representation of the sequence of the time-stamped clinical events.

In some embodiments, the network server or encoder configures the multi-nodal perception engine for filtering the time-stamped clinical events within the session container file using machine learning with feature extraction for event correlation using computational intelligence, the multi-nodal perception engine interfacing with distributed hardware units.

In some embodiments, the network server or encoder generates the predictive data model by generating an Attribute-Relation File Format and the artificial intelligence network data structures and creates the temporal sequence of the time-stamped clinical events within the session container file, the temporal sequence relating to predicted locations of surgical error, wherein the interface indicator receives rating indicia for the error assessments of the time-stamped clinical events.

In some embodiments, the network server implements post-processing of the time-stamped clinical events within the session container file for comparative processing for outcome links to generate hazard maps for the interface indicator.

These are illustrative example embodiments and other variations may be described herein.

DETAILED DESCRIPTION

To illustrate various embodiments, reference will be made to components, architecture, descriptions and definitions. Embodiments may provide a system, method, platform, device, and/or computer readable medium which provides comprehensive data collection of details of patient care in a surgical operating room (OR), intensive care unit, trauma room, emergency department, interventional suite, endoscopy suite, obstetrical suite, and/or medical or surgical ward, outpatient medical facility, clinical site, or healthcare training facility (simulation centres). These different example environments or settings may be referred to herein as an operating or clinical site.

Embodiments described herein may provide device, system, method, platform and/or computer readable medium which provides comprehensive data collection of all details of patient care in one or more such settings to: identify and/or analyze errors, adverse events and/or adverse outcomes; provide comprehensive data allowing investigation of the chain of events from an error to adverse events; provide information concerning individual and/or team performance, e.g., for high-stakes assessment of competence, certification and/or re-certification of healthcare professionals; provide data to be used for design of individualized training interventions for surgical and/or medical teams based on demonstrated performance deficiencies; identify critical safety deficiencies in human performance and/or safety processes, e.g., for creation of individualized solutions aimed to reduce risks and/or enhance patient safety; and/or assess critical safety deficiencies in medical technology and/or provide feedback for improvement in design and/or performance, analyze and monitor efficiency and safety processes in a clinical environment.

In an aspect, embodiments described herein relate to a system for collecting and processing medical or surgical data. The system may have a plurality of hardware units for collecting real-time medical or surgical data streams having a control interface coupled by a network to cameras, sensors, audio devices, and patient monitoring hardware, the real-time medical or surgical data streams relating to a real-time medical procedure within an operating or clinical site. The hardware units may gather or collect one or more independent data streams from different devices, and in turn each data stream provided the hardware unit may be independent of other data streams provided by other hardware units. According, the system may implement synchronization techniques of the data streams as described herein. The system may have device middleware and hardware for translating, connecting, and formatting the real-time medical or surgical data streams received independently from the hardware units (which in turn may receive data feeds from different devices independently).

A technical challenge with surgical recordings results from a lack of synchronization of audio/video feeds with digital data streams (e.g., from sensors). Synchronization is an important feature that may be significantly advantageous in converting unstructured data into structured data, for example, as inputs into a perception engine (e.g., that can utilized automate the assessment process and/or provide other types of machine-learning outputs, predictions and/or estimations). For example, replacing (and/or reducing) a need for manual evaluation of the recordings with automated software may help provide a cheap and scalable approach.

The system may have an encoder with a network server for synchronizing and recording the real-time medical or surgical data streams to a common clock or timeline to generate a session container file. As noted, the synchronization may aggregate independent data feeds in a consistent manner to generate a comprehensive data feed generated by data from multiple independent devices.

The system may have network infrastructure connecting the encoder, the device middleware and hardware and the hardware units, and switching or gateway hardware for a virtual private network to transmit the session container file.

In some example embodiments, the device middleware and hardware establishes a secure reliable connection using the network infrastructure for communication with the encoder and the hardware units.

In some example embodiments, the device middleware and hardware implements data conformity and accurate synchronization for the real-time medical or surgical data streams using network protocols for clock synchronization between the hardware units to assist the encoder to generate the session container file.

The perception engine, for example, may be utilized to provide a multi-nodal approach for machine learning. The perception engine may receive as inputs, for example, various recording data, physiological data, among others.

The perception engine may be configured for generating a protocol for data extraction from the session container file, processing the data using the protocol to extract patterns for time-stamped clinical events within the session container file, generating an interface indicator for a temporal sequence of the time-stamped clinical events within the session container file and error assessments, and generating a predictive data model for refining protocol generation using support vector machines or artificial intelligence network data structures with neural networks for modelling correlation of data for interference and feature extraction. For example, the obtained data may be provided in the form of audio clippings recorded from surgical procedures, and the perception engine may apply machine learning techniques to generate automated predictions. These predictions may be verified and/or compared against records of tracked incidents and/or events for accuracy, and the perception engine may be tuned over a period of time based on the particular outputs desired, their accuracy, specificity, and sensitivity, among others. The data extraction may involve extracting audio data for processing. The extraction may involve extracting video data for processing.

The machine-learning approaches may include alternating decision trees, random forests, among others, and may be tuned for application in relation to surgical or medical contexts. Where the perception engine is being used for analysis of medical and/or clinical events (e.g., a surgical error/adverse outcome), the perception engine may be tuned to improve the likelihood of detecting true positives, at the cost of increasing the likelihood of detecting false positives. For example, the perception engine may be utilized to provide instruction sets such as metadata indicative of when a medical reviewer should review a surgical procedure. In such a scenario, it may be advantageous for the perception engine to apply a broader scope of detection, possibly including false positives (which can then be verified and discarded by a medical reviewer).

The outputs from the perception engine may be provided in the form of various interfaces, such as graphical user interfaces for indication of when clinical events have been estimated, or application programming interfaces for computerized interactions with third party devices and/or databases.

In some example embodiments, the encoder and device middleware and hardware are operable to interface with third party devices to receive additional data feeds as part of the real-time medical or surgical data streams.

In some example embodiments, the system has a central control station accessible using the control interface, the control station configured to control processing of the data streams in response to input control comprising play/pause, stop session, record session, move to session frame, split-display, recording status indicator, and log file.

In some example embodiments, the network infrastructure provides increased fail-over and redundancy for the real-time medical or surgical data streams from the hardware units.

In some example embodiments, the system has a storage area network for storing data container files of the real-time medical or surgical data streams until scheduled transmission.

In some example embodiments, the encoder implements identity anonymization and encryption to the medical or surgical data.

In some example embodiments, the encoder processes the real-time medical or surgical data streams to generate measurement metrics relating to the medical procedure.

In some example embodiments, the real-time medical or surgical data streams correlates to a timeline, wherein the encoder detects events within the real-time medical or surgical data streams at corresponding times on the timeline, and tags and timestamps the session container file with the events, the timestamps corresponding to times on the timeline.

In some example embodiments, the system has an intelligent dashboard interface for annotation and tagging of the synchronized medical or surgical data streams, wherein the intelligent dashboard may implement a viewer with playback viewing for reviewing content and interface controls for tagging content.

In some example embodiments, the intelligent dashboard is multi-dimensional in that the union of all dimension variables for the medical procedure as represented by the real-time medical or surgical data streams may indicate a specific set of one or more applicable annotation dictionaries or coding templates.

In some example embodiments, example variables that may be used to determine the annotation and tagging dictionary may be: the type of medical procedure being performed, the aspect of the procedure that is being analyzed, the geographic area/region where the procedure is being performed.

In another aspect, there is provided a multi-channel encoder for collecting, integrating, synchronizing and recording medical or surgical data streams onto a single interface with a common timeline or clock, the medical or surgical data streams received as independent real-time or live data streams from a plurality of hardware units, the encoder having a network server for scheduling transmission of session file containers for the recordings, the encoder processing the medical or surgical data streams to generate measurement metrics relating to a real-time medical procedure. The encoder aggregates multiple independent data streams or feeds received from different hardware unit and smart devices.

In some example embodiments, the encoder generates as output a single session transport file using lossless compression operations.

In some example embodiments, the encoder detects completion of a recording of the data streams and securely encrypts the single transport file.

In some example embodiments, the encoder implements identity anonymization to the medical or surgical data.

In some example embodiments, the data streams include audio, video, text, metadata, quantitative, semi-quantitative, and data feeds.

In another aspect, there is provided a method for collecting and processing medical or surgical data. The method involves receiving, at a multi-channel encoder, a plurality of live or real-time independent input feeds from one or more data capture devices located in an operating room or other patient intervention area, the input feeds relating to a live or real-time medical procedure;

The method may involve synchronizing, by the encoder, the plurality of live independent input feeds onto a single interface with a common timeline or clock, and recording the synchronized input feeds using a network server. The method may involve generating, by the encoder, an output session file using the synchronized input feeds, and transmitting the output session file using the network server.

In some example embodiments, the method further involves processing the data streams for identity anonymization.

In some example embodiments, the method further involves routing the data streams using a switch router to the encoder.

In a further aspect, there is provided a cloud based system for collecting and processing medical or surgical data. The system may have an encoder having a control interface for, in response to receiving a control command, triggering collection of real-time medical or surgical data streams by smart devices including cameras, sensors, audio devices, and patient monitoring hardware, the medical or surgical data relating to a real-time medical procedure within an operating or clinical site, the encoder for authenticating the smart devices, the smart devices synchronizing the real-time medical or surgical data streams by embedding timestamp markers within the real-time medical or surgical data streams, the timestamp markers generated by each smart device by a device clock. The system also has a media management hub server with middleware and hardware for translating, connecting, formatting, and recording the real-time medical or surgical data streams to generate session container files on network accessible storage devices, and wireless network infrastructure to provide a secure network connection between the encoder, the smart devices and the media management hub server for communication of the real-time medical or surgical data streams. The system has a central content server for storing and distributing the session container files and providing a two-way communication interface for the media management hub to implement a file transfer handshake for the session container files. The system has switching or gateway hardware for a virtual private network tunnel to transmit the session container files from the media management hub to the central content server. The cloud based system may enable autonomous, independent smart devices to time stamp collected data and implement synchronization techniques to aggregate independent data streams and feeds to generate a comprehensive, real-time data representation of the medical or surgical procedure or unit.

In some example embodiments, the media management hub server broadcasts clock data to the smart devices for synchronization of the device clocks.

In some example embodiments, the encoder provides a user interface to receive the control command and display real-time visual representations of the medical or surgical data.

In some example embodiments, the media management hub server aggregates, packages, compresses and encrypts the real-time data streams to generate the session container files.

In some example embodiments, the media management hub server manages the smart devices based on location, schedule, zone and requirements.

In some example embodiments, the media management hub server receives operating status data from the smart devices to generate a management interface with a visual representation of the operating status data for the smart devices, the operating status data including online, offline, running capture, and on-board storage.

In some example embodiments, the media management hub server processes the operating status data to detect smart devices operating outside of normal conditions and in response generating an alert notification of the detected smart devices operating outside of normal conditions.

In some example embodiments, the media management hub server implements a device communication interface for the smart devices to implement a device data transfer handshake for the real-time medical or surgical data streams.

In some example embodiments, the media management hub server authenticates the smart devices.

In some example embodiments, the system has a computational intelligence platform for receiving the session container files to construct an analytics model to identify clinical factors within the session container files for predictions, costs and safety hazards, the analytics model providing a network for extracting features, correlations and event behaviour from the session container files that involve multivariable data sets with time-variant parameters.

In some example embodiments, the system has a training or education server to receive the session container files, process the session container files to identify root causes of adverse patient outcomes and generate a training interface to communicate training or performance feedback data using the identified root causes and the session container files.

In some example embodiments, the smart devices include motion tracking devices for markerless motion tracking of objects within the operating or clinical site, the system further comprising a processor configured to convert captured motion data from the motion tracking devices into data structures identifying human factors, workflow design and chain-of-events.

The platform may have different aspects including hardware, software, front end components, middleware components, back end components, rich content analysis software and analytics software (e.g., database).

FIG. 1 shows an architectural platform according to some embodiments. The platform 10 includes various hardware components such as a network communication server 12 (also "network server") and a network control interface 14 (including monitor, keyboard, touch interface, tablet, processor and storage device, web browser) for on-site private network administration.

Multiple processors may be configured with operating system and client software (e.g., Linux, Unix, Windows Server, or equivalent), scheduling software, backup software. Data storage devices may be connected on a storage area network.

FIG. 1 shows a surgical or medical data encoder 22. The encoder may be referred to herein as a data recorder, a "black-box" recorder, a "black-box" encoder, and so on. Further details will be described herein. The platform 10 may also have physical and logical security to prevent unintended or unapproved access. A network and signal router 16 connects components.

The platform 10 includes hardware units 20 that include a collection or group of data capture devices for capturing and generating medical or surgical data feeds for provision to encoder 22. The hardware units 20 may include cameras 30 (e.g., wide angle, high definition, pan and zoom camera, such as a Sony EVI-HD1™ or other example camera) mounted within the surgical unit, ICU, emergency unit or clinical intervention units to capture video representations of the OR as video feeds for provision to encoder 22. The video feed may be referred to as medical or surgical data. An example camera 30 is a laparoscopic or procedural view camera (AIDA™ Karl Storz™ or equivalent) resident in the surgical unit, ICU, emergency unit or clinical intervention units. Example video hardware includes a distribution amplifier for signal splitting of Laparoscopic cameras. The hardware units 20 have audio devices 32 (e.g., condenser gooseneck microphones such as ES935ML6™, Audio Technica™ or other example) mounted within the surgical unit, ICU, emergency unit or clinical intervention units to provide audio feeds as another example of medical or surgical data. Example sensors 34 installed or utilized in a surgical unit, ICU, emergency unit or clinical intervention units include but not limited to: environmental sensors (e.g., temperature, moisture, humidity, etc., acoustic sensors (e.g., ambient noise, decibel), electrical sensors (e.g., hall, magnetic, current, mems, capacitive, resistance), flow sensors (e.g., air, fluid, gas) angle/positional/displacement sensors (e.g., gyroscopes, altitude indicator, piezoelectric, photoelectric), and other sensor types (e.g., strain, level sensors, load cells, motion, pressure). The sensors 34 provide sensor data as another example of medical or surgical data. The hardware units 20 also include patient monitoring devices 36 and an instrument lot 18.

The customizable control interface 14 and GUI (may include tablet devices, PDA's, hybrid devices, convertibles, etc.) may be used to control configuration for hardware components of unit 20. The platform 10 has middleware and hardware for device-to-device translation and connection and synchronization on a private VLAN or other network. The computing device may be configured with anonymization software, data encryption software, lossless video and data compression software, voice distortion software, transcription software. The network hardware may include cables such as Ethernet, RJ45, optical fiber, SDI, HDMI, coaxial, DVI, component audio, component video, and so on to support wired connectivity between components. The network hardware may also have wireless base stations to support wireless connectivity between components.

Descriptions and Definitions for an Illustrative Embodiment

Illustrative definitions of various components are provided as examples of various embodiments.

A Private VLAN may refer to a networking technique, which provides network segregation and secure hosting of a network on the clients, existing backbone architecture via restricted "private ports".

A VPN may extend a private network across a public network, such as the Internet. It enables a computer or network-enabled device to send and receive data across shared or public networks as if it were directly connected to the private network, while benefiting from the functionality, security and management policies of the private network. FIG. 1 shows an example VPN 24 (Virtual Private Network) connecting to a switch and gateway hardware and to encoder 22.

Anonymization Software for anonymizing and protecting the identity of all medical professionals, patients, distinguishing objects or features in a medical, clinical or emergency unit. This software implements methods and techniques to detect facial, distinguishing objects, or features in a medical, clinical or emergency unit and distort/blur the image of the distinguishing element. The extent of the distortion/blur is limited to a localized area, frame by frame, to the point where identity is protected without limiting the quality of the analytics.

Voice or Vocabulary Alteration Software for anonymizing and protecting the identity of all medical professionals, patients, distinguishing objects or features in a medical, clinical or emergency environment. This software may implement methods and techniques running on hardware in a medical, clinical or emergency environment to alter voices, conversations and/or remove statements of everyday language to preserve the identity of the speaker while at the same time maintaining the integrity of the input stream so as to not adversely impact the quality of the analytics.

Data Encryption Software may execute to encrypt computer data in such a way that it cannot be recovered without access to the key. The content may be encrypted at source as individual streams of data or encrypted as a comprehensive container file for purposes of storage on an electronic medium (i.e. computer, storage system, electronic device) and/or transmission over internet 26. Encrypt/decrypt keys may either be embedded in the container file and accessible through a master key, or transmitted separately.

Lossless Video and Data Compression software executes with a class of data compression techniques that allows the original data to be perfectly or near perfectly reconstructed from the compressed data.

Device middleware and hardware may be provided for translating, connecting, formatting and synchronizing of independent digital data streams from source devices. The platform 10 may include hardware, software, algorithms and methods for the purpose of establishing a secure and reliable connection and communication directly, or indirectly (via router, wireless base station), with the OR encoder 22, and third-party devices (open or proprietary) used in a surgical unit, ICU, emergency or other clinical intervention unit.

The hardware and middleware may assure data conformity, formatting and accurate synchronization. Synchronization may be attained by utilizing networking protocols for clock synchronization between computer systems and electronics devices over packet-switched networks like NTP, etc.

The hardware unit may include third party devices (open or proprietary) non limiting examples being $O_2$ Sat monitors, Anesthesia monitors, patient monitors, energy devices, intelligent surgical devices (i.e. smart staplers, smart laparoscopic instruments), autonomous surgical robots, etc. hospital patient administration systems (i.e. electronic patient records), Intelligent implants, Sensors including but not limited to: Environmental sensors: i.e. temperature, moisture, humidity, etc. Acoustic sensors: i.e. ambient noise, decibel, etc. Electrical sensors: i.e. hall, magnetic, current, mems, capacitive, resistance, etc. Flow sensors: i.e. air, fluid, gas, etc. angle/positional/displacement sensors: i.e. gyroscopes, attitude indicator, piezoelectric, photoelectric, etc. Other sensors: strain, level sensors, load cells, motion, pressure, and so on.

Transcription Software may assist in the conversion of human speech into a text transcript utilizing technologies such as natural language speech recognition.

OR or Surgical encoder: The OR or Surgical encoder (e.g., encoder 22) may be a multi-channel encoding device that records, integrates, ingests and/or synchronizes independent streams of audio, video, and digital data (quantitative, semi-quantitative, and qualitative data feeds) into a single digital container. The digital data may be ingested into the encoder as streams of metadata and is sourced from an array of potential sensor types and third-party devices (open or proprietary) that are used in surgical, ICU, emergency or other clinical intervention units. These sensors and devices may be connected through middleware and/or hardware devices which may act to translate, format and/or synchronize live streams of data from respected sources.

Customizable Control Interface and GUI. The Control Interface (e.g., 14) may include a Central control station (non-limiting examples being one or more computers, tablets, PDA's, hybrids, and/or convertibles, etc.) which may be located in the clinical unit or another customer designated location. The Customizable Control Interface and GUI may contain a customizable graphical user interface (GUI) that provides a simple, user friendly and functional control of the system.

Example features of the Customizable Control Interface and GUI may include but are not limited to: Play/Pause button which may enable some segments of the procedure to not be recorded. To omit these segments from the recording, the user interface can pause the recordings and re-start when desired. The pause and play time-stamps are recorded in a log file, indicating the exact times of the procedure that were extracted; Stop session button that when selected, files are closed and automatically transferred to the storage area network (SAN); Split-screen quadrant display of video feeds, which may provide visual displays of videos in real-time during recording; Visual indicator of recording may be a colored, blinking dot appeared on screen to provide visual indication to the team that video and audio feeds are being recorded; Log file where at the end of the recording, a log file may be generated that indicates key time points, including start and end time of the recording session, pauses and replays; Password protection, which may refer to an interface that is secured with one or several layers of password protection to ensure maintenance of patient confidentiality and privacy.

System Level Application may refer to a platform 10 that is designed to be a scalable platform ranging from small single clinical intervention unit to large-scale clinical intervention unit(s). Where necessary, a switching router may be used in larger scale applications to maximize efficiency and/or deliver increased fail-over and redundancy capabilities.

Example Applications

In an aspect, embodiments described may provide an illustrative small scale application. As a small single encoder platform, audio, video and data feeds are connected to the encoder 22 directly via cable or indirectly via connected wireless base station.

Using the Customizable Control Interface and GUI, activation of the system may commence recording, collection and streaming of all available audio, video, sensor and data feeds (which may be referred to as medical and surgical data feeds) to the encoder 22. It will use all available cameras including both mounted and laparoscopic, all audio microphones and all available and implemented sensors and third-party devices (open or proprietary) used in a surgical units, ICU, emergency or other clinical intervention units. Pause or Stop or Play commands will send corresponding commands to the encoder 22. Digital data will be formatted, translated and synchronized through middleware hardware and software and using networking protocols for clock synchronization across the network. Digital data will be ingested into the encoder 22 as metadata.

The encoder 22 may be responsible for synchronizing all feeds, encoding them into a signal transport file using lossless audio/video/data compression software.

Upon completion of the recording, the container file will be securely encrypted. Encrypt/decrypt keys may either be embedded in the container file and accessible through a master key, or transmitted separately.

The encrypted file may either be stored on the encoder 22 or stored on a Storage area network until scheduled transmission.

The communications server on the private VLAN will be responsible for schedule management and the automated file and key transmission. This may be done through a private VLAN on the client environment and transmitted via Virtual Private Network (VPN) 24 on public data lines directed back to a back office.

The communications server may be responsible for backing up data including audio, video, data, encrypted files, etc. utilizing backup software as part of the configuration.

The communications server may be responsible for hosting and directing all traffic between the private VLAN and back office.

In another aspect, embodiments described herein may involve an encoder configured for hosting and operating anonymization and voice or vocabulary alteration software(s) for the purpose of protecting the identity of medical professionals, patients, distinguishing objects or features in a medical, clinical or emergency environment. This may be done either before compressing, containerizing and/or encrypting the collective data, or after receipt of transmission to back office and decryption.

In an aspect, embodiments described may provide an illustrative larger scale application.

Larger application environments may be required. In order to maximize efficiency and deliver increased fail-over and redundancy capabilities, a switching router may be used (e.g., router 16 of FIG. 1). In this example, larger application audio, video and data feeds may connect by cable or via connected wireless base station to a switching router 16. The purpose of the router is to route audio, video and data feeds to one of multiple encoders 22 available on the network. This may provide for more cost effective implementation, greater spatial coverage and increased redundancy and fail-over for the platform 10.

Using the Customizable Control Interface 14 and GUI, activation signals may trigger or commence recording, collection and streaming of all available audio, video and data feeds (from components of hardware units 20) to one of multiple available encoders 22 via the switching router 16. For example, the data stream or feeds may be from all available cameras including both mounted and laparoscopic, all audio microphones and all available and implemented sensors and third-party devices (open or proprietary) used in hardware units 20 which may relate to surgical units, ICU, emergency or other clinical intervention units. Control commands such as Pause/Stop/Play commands received at Control Interface 14 may send corresponding control commands to the encoder 22. Digital data may be formatted, translated and synchronized through middleware hardware and software and using networking protocols for clock synchronization across the network. Digital data streams may be ingested into the encoder 22 as Metadata. The encoder 22 may be responsible for synchronizing all feeds and encoding them into a signal transport file using lossless audio/video/data compression software.

Upon completion of the recording, the container file may be securely encrypted. Encrypt/decrypt keys may either be embedded in the master file and accessible through a master key, or have a separate key. The encrypted file will either be stored on the encoder 22 or stored on a Storage area network until scheduled transmission.

The communications server on the private VLAN 24 may be responsible for schedule management and the automated file and key transmission. This may be done through a private VLAN on the client environment and transmitted via VPN 24 on public data lines directed back to a back end office, or other system.

The communications server (e.g., network server 12) may be responsible for backing up data including audio, video, data, encrypted files, etc. utilizing backup software as part of the configuration. The communications server may be responsible for hosting and directing all traffic between the private VLAN and back office system, for example.

In some examples, encoder 22 may also be responsible for hosting and operating anonymization and voice/vocabulary distortion software(s) for the purpose of protecting the identity of all medical professionals, patients, distinguishing objects or features in a medical, clinical or emergency environment captured in data streams of hardware units 20. This may be done either before compression, containerizing and encryption, or after decrypting in back office system.

In an aspect, embodiments described herein may provide a device, system, method, platform and/or computer readable medium which is housed in clinical areas and allows gathering of comprehensive information from every aspect of the individual, team and/or technology performances and their interaction during clinical interventions. The data capture devices may be grouped as one or more hardware units 20 as shown in FIG. 1.

According to some embodiments, this information may include: video from the procedural field; video of the clinical environment; audio; physiological data from the patient; environmental factors through various sensors (e.g., environmental, acoustic, electrical, flow, angle/positional/displacement and other potential sensors); software data from the medical devices used during intervention; and/or individual data from the healthcare providers (e.g., heart rate, blood pressure, skin conductance, motion and eye tracking, etc.).

According to some embodiments, this information then may be synchronized (e.g., by the encoder 22) and/or used to evaluate: technical performance of the healthcare providers; non-technical performance of the clinical team members; patient safety (through number of registered errors and/or adverse events); occupational safety; workflow; visual and/or noise distractions; and/or interaction between medical/surgical devices and/or healthcare professionals, etc.

According to some embodiments, this may be achieved by using objective structured assessment tools and questionnaires and/or by retrieving one or more continuous data streams from sensors 34, audio devices 32, an anesthesia device, medical/surgical devices, implants, hospital patient administrative systems (electronic patient records), or other data capture devices of hardware unit 20.

According to some embodiments, significant "events" may be detected, tagged, time-stamped and/or recorded as a time-point on a timeline that represents the entire duration of the procedure and/or clinical encounter. The timeline may overlay captured and processed data to tag the data with the time-points.

Upon completion of data processing and analysis, one or more such events (and potentially all events) may be viewed on a single timeline represented in a GUI, for example, to allow an assessor to: (i) identify event clusters; (ii) analyze correlations between two or more registered parameters (and potentially between all of the registered parameters); (iii) identify underlying factors and/or patterns of events that lead up to adverse outcome; (iv) develop predictive models for one or more key steps of an intervention (which may be referred to herein as "hazard zones") that may be statistically correlated to error/adverse event/adverse outcomes, v) identify a relationship between performance outcomes and clinical costs. These are non-limiting examples of uses an assessor may make of a timeline presented by the GUI representing recorded events.

Analyzing these underlying factors according to some embodiments may allow one or more of: (i) proactive monitoring of clinical performance; and/or (ii) monitoring of performance of healthcare technology/devices (iii) creation of educational interventions—e.g., individualized structured feedback (or coaching), simulation-based crisis scenarios, virtual-reality training programs, curricula for certification/re-certification of healthcare practitioners and institutions; and/or identify safety/performance deficiencies of medical/surgical devices and develop recommendations for improvement and/or design of "intelligent" devices and implants—to curb the rate of risk factors in future procedures and/or ultimately to improve patient safety outcomes and clinical costs.

The device, system, method and computer readable medium according to some embodiments, may combine capture and synchronization, and secure transport of video/audio/metadata with rigorous data analysis to achieve/demonstrate certain values. The device, system, method and computer readable medium according to some embodiments may combine multiple inputs, enabling recreation of a full picture of what takes place in a clinical area, in a synchronized manner, enabling analysis and/or correlation of these factors (between factors and with external outcome parameters (clinical and economical). The system may bring together analysis tools and/or processes and using this approach for one or more purposes, examples of which are provided herein.

Beyond development of a data platform 10, some embodiments may also include comprehensive data collection and/or analysis techniques that evaluate multiple aspects of any procedure. One or more aspects of embodiments may include recording and analysis of video, audio and metadata feeds in a synchronized fashion. The data platform 10 may be a modular system and not limited in terms of data feeds—any measurable parameter in the OR/patient intervention areas (e.g., data captured by various environmental acoustic, electrical, flow, angle/positional/displacement and other sensors, wearable technology video/data stream, etc.) may be added to the data platform 10. One or more aspects of embodiments may include analyzing data using validated rating tools which may look at different aspects of a clinical intervention. These aspects may include: technical performance, non-technical "team" performance, human factors, patient safety, occupational safety, workflow, audio/visual distractions, etc. Video, audio and synchronized metadata may be analyzed using manual and/or automatic data analysis techniques, which may detect pre-determined "events" that can be tagged and/or time-stamped. All tagged events may be recorded on a master timeline that represents the entire duration of the procedure. Statistical models may be used to identify and/or analyze patterns in the tagged events. Various embodiments may encompass a variety of such statistical models, current and future.

According to some embodiments, all video feeds and audio feeds may be recorded and synchronized for an entire medical procedure. Without video, audio and data feeds being synchronized, rating tools designed to measure the technical skill and/or non-technical skill during the medical procedure may not be able to gather useful data on the mechanisms leading to adverse events/outcomes and establish correlation between performance and clinical outcomes.

According to some embodiments, measurements taken (e.g., error rates, number of adverse events, individual/team/technology performance parameters) may be collected in a cohesive manner. According to some embodiments, data analysis may establish correlations between all registered parameters if/as appropriate. With these correlations, hazard zones may be pinpointed, high-stakes assessment programs may be developed and/or educational interventions may be designed.

In an aspect, embodiments described herein may provide a device, system, method and/or computer readable medium for recording data which comprises multiple audio/video/metadata feeds captured by hardware devices in the OR/patient intervention areas (e.g., room cameras, microphones, procedural video, patient physiology data, software data from devices used for patient care, metadata captured by environmental/acoustic/electrical/flow-/angle/positional/displacement sensors and other parameters outlined herein). The captured data feeds may be simultaneously processed with an encoder (e.g., encoder 22 of FIG. 1), synchronized and recorded. These synchronized video, audio, and time-series data may provide a complete overview of the clinical procedure/patient interaction. At the end of the procedure, the data may be synchronized, compressed, encrypted and may be anonymized prior to transmission to a data analysis computing system/centre for assessment and/or statistical analysis.

The data may be analyzed using encoder 22 (which may include analysis software and database) which preserves the time synchronization of data captured using multiple assessment tools/data parameters and allows export of the analyzed data into different statistical software. The exported data may be a session container file.

A device, system, method and/or computer readable medium according to some embodiments may record video, audio and digital data feeds from a clinical area in a synchronized fashion. The platform may be a modular system and is not limited in terms of the example data feeds described. Other data feeds relating to medical procedures may also be collected and processed by platform 10. For example, any measurable parameter in the OR (e.g., data captured by various environmental acoustic, electrical, flow, angle/positional/displacement and other sensors, wearable technology video/data stream, etc.) may be added to the data recorder (e.g., encoder 22 of FIG. 1).

A device, system, method and/or computer readable medium according to some embodiments analyzes comprehensive, synchronized data using validated rating tools that consider different aspects or measurements of surgery/clinical interventions. These aspects or measurements may include: technical surgical performance, non-technical "team" performance, human factors, patient safety, occupational safety, workflow, audio/visual distractions, etc. Video, audio and/or metadata may be analyzed using manual and/or automatic data analysis techniques, which may detect specific "events" which may be tagged and time-stamped in the session container file or processed data stream.

A device, system, method and/or computer readable medium according to some embodiments records all tagged events on a master timeline that represents the entire duration of the procedure/clinical interaction. Statistical models may be used to identify and analyze patterns in the tagged events. The master timeline may be correlated to the processed medical data and the session file.

A device, system, method and/or computer readable medium according to some embodiments generates structured performance reports based on the captured and processed medical data for identification and determination of individual/team/technology performance measurements and organizational deficiencies that may impact patient safety, efficiency and costs.

A device, system, method and/or computer readable medium according to some embodiments provides a base for the design of targeted educational interventions to address specific safety hazards. These may include individualized training curricula, simulation-based training scenarios, Virtual Reality simulation tasks and metrics, and educational software.

A device, system, method and/or computer readable medium according to some embodiments may provide for high-stakes assessment programs for performance assessment, certification and re-certification.

Embodiments described herein may integrate multiple, clinically relevant feeds (audio/video/metadata) for a medical procedure, and allows a comprehensive analysis of human and technology performance for the medical procedure, organizational processes and links them to safety efficiency and outcomes as events, to develop solutions which aim to improve safety and efficiency and reduce costs.

Embodiments described herein may enable successful identification, collection and synchronization of multiple video, audio and metadata feeds relevant to a medical procedure (e.g., to evaluate different metrics of the medical procedure) with ample processing power to render all the video and audio in a useable fashion.

Embodiments described herein may employ measurement tools, and enable and incorporates objective assessment of various aspects of human and technology performance and environmental factors, with a view to understanding chains of events which lead to adverse outcomes in medical procedures and other aspects of medicine.

Possible applications for some embodiments include one or more of the following: (i) Documentation of various aspects of patient care in clinical areas with a high-risk for adverse outcomes. Comprehensive data collection by the encoder according to some embodiments may enable and/or provide for a detailed reconstruction of any clinical encounter. (ii) Analysis of chains of events leading to adverse outcomes. The data collection and processing according to some embodiments provide an opportunity to retrospectively evaluate one or more mechanisms and/or root causes leading to adverse outcomes in medicine and surgery. (iii) The analysis according to some embodiments may generate knowledge of the incidence and background of human errors and may enable development of strategies to mitigate the consequences of such errors. (iv) Design of training interventions for surgical teams. According to some embodiments, all identified crisis scenarios may be stored in a database and associated with simulation interventions which aim to prepare clinical teams for common clinical challenges and mitigate the impact of errors on clinical outcomes. (v) Evaluation/Improvement/development of existing/new healthcare technology and new treatments. According to some embodiments, the comprehensive data set may be used to evaluate safety hazards associated with implementation of new healthcare technologies. Furthermore, it may enable evaluation of the impact of healthcare technologies on efficiency. (vi) Use for certification and accreditation purposes. According to some embodiments, the data may be used for assessment of human performance and development of pass/fail scores using standard setting methodologies.

Embodiments described herein may be for use in association with OR settings. Embodiments, however, are not so limited. Embodiments may also find application in medical settings more generally, in surgical settings, in intensive care units ("ICU"), in trauma units, in interventional suites, in endoscopy suites, in obstetrical suites, and in emergency room settings. Embodiments may be used in outpatient treatment facilities, dental centers and emergency medical services vehicles. Embodiments can be used in simulation/training centers for education of healthcare professionals.

Example applications are presented for the purpose of illustration and are not intended to be exhaustive or to limit embodiments to the precise form disclosed. Other advantages, features and/or characteristics of some embodiments, as well as methods of operation and/or functions of the related elements of the device, system, method, platform and/or computer readable medium, and/or the combination of steps, parts and/or economies of manufacture, may become more apparent upon consideration of the accompanying drawings. Certain features of the system, method, device and/or computer readable medium according to some embodiments, as to their organization, use, and/or method of operation, together with further objectives and/or advantages thereof, may be better understood from the accompanying drawings in which present example embodiments. The drawings are for the purpose of illustration and/or description only, and are not intended as a definition of the limits of the invention.

Naturally, alternate designs and/or embodiments may be possible (e.g., with substitution of one or more components, units, objects, features, steps, algorithms, etc. for others, with alternate configurations of components, units, objects, features, steps, algorithms, etc.).

Although some of the components, units, objects, features, steps, algorithms, relations and/or configurations according some embodiments may not be specifically referenced in association with one another, they may be used, and/or adapted for use, in association therewith. The herein mentioned, depicted and/or various components, units, objects, structures, configurations, features, steps, algorithms, relationships, utilities and the like may be, but are not necessarily, incorporated into and/or achieved by some embodiments. Any one or more of the herein mentioned components, units, objects, structures, configurations, features, steps, algorithms, relationships, utilities and the like may be implemented in and/or by some embodiments, on their own, and/or without reference, regard or likewise implementation of any of the other herein mentioned components, units, objects, structures, configurations, features, steps, algorithms, relationships, utilities and the like, in various permutations and combinations.

Other modifications and alterations may be used in the design, manufacture, and/or implementation of other embodiments according to the present invention without departing from the spirit and scope of the invention.

Multi-Channel Recording Device or ENCODER

Figure 2:
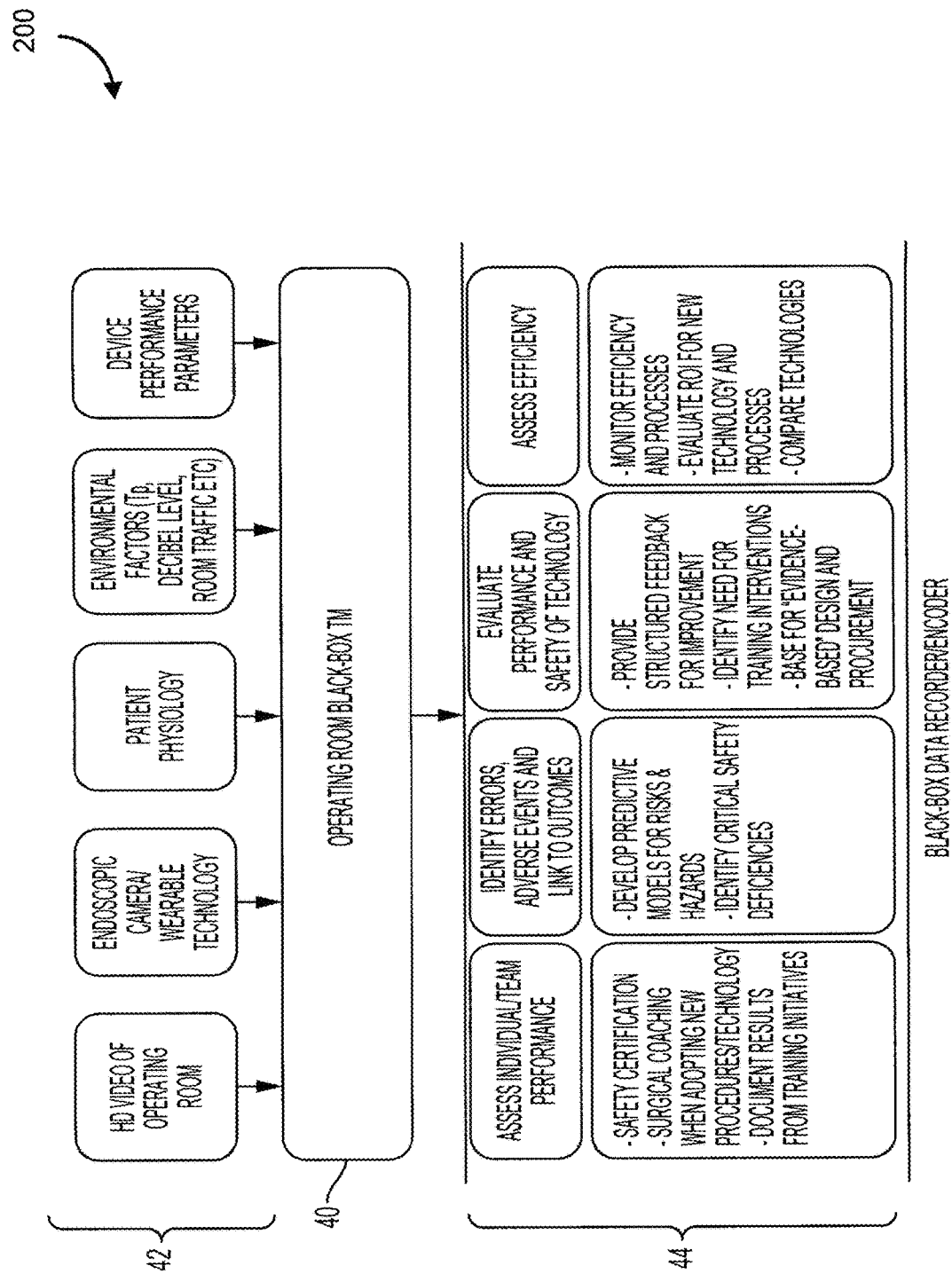
FIG. 2 illustrates a schematic of a multi-channel recording device or encoder according to some embodiments.

FIG. 2 illustrates a schematic diagram 200 of a multi-channel recording device 40 with input feeds 42 and output data 44. The recording device 40 may be referred to herein as an encoder. The multi-channel data recording device 40 of FIG. 2 may be the encoder 22 of FIG. 1 in some embodiments, or the encoder 1610 according to other embodiments The multi-channel recording device 40 may receive input feeds 42 from various data sources including, for example, feeds from cameras in the OR, feeds from wearable devices, feeds related to patient physiology from data stores, monitoring devices and sensors, feeds for environment factors from various sensors (temperature, decibel level, room traffic), feeds for device performance parameters, and so on. The multi-channel recording device 40 may synchronize and record the feeds to generate output data 44 (e.g., for export as a session file). The output data may include, for example, measurement values to assess individual and team performance, identify errors and adverse events and link to outcomes, evaluate performance and safety of technology, and assess efficiency.

There may have been a paucity of research on contributing factors and underlying mechanisms of error in surgery. The complex, dynamic, and/or data-dense environment of the OR may make it difficult to study root causes of error and/or patterns of events which may lead to adverse outcomes. A synchronized multi-channel recording device 40 according to some embodiments provides a comprehensive overview or data representation of the OR. Modeled after the aviation black-box, this multi-channel recording device 40 or "black-box encoder" may register multiple aspects of the intraoperative OR environment, including room and/or procedural video, audio, sensors, an anesthesia device, medical/surgical devices, implants, and hospital patient administrative systems (electronic patient records). The black-box recording device 40 may be installed in real-life ORs/patient intervention areas at hospitals, outpatient clinical facilities, emergency medical services vehicles, simulation/training centres, among other places.

The black-box recorder 40 may be for use in anesthesiology, general minimally invasive surgery (MIS) surgery, interventional radiology, neurosurgery, and clinical practice. The black-box recorder 40 may achieve synchronization, audio, video, data capture, data storage, data privacy, and analysis protocols, among other things.

According to some embodiments, a multi-channel data recording device 40 is provided for use in the clinical environment which simultaneously records multiple synchronized data feeds, including procedural views, room cameras, audio, environmental factors through multiple sensors, an anesthesia device, medical/surgical devices, implants, and hospital patient administrative systems (electronic patient records). A multi-perspective view of the operating theatre may allow for simultaneous analysis of technical and non-technical performance and identification of key events leading up to an adverse outcome. Implementation of the black-box platform according to embodiments in real-life ORs may reveal valuable insights into the interactions which occur within the OR/patient intervention area, as a tool to identify, analyze and/or prevent errors in the intraoperative environment.

The multi-channel "black-box" encoder 40 integrates and synchronizes audiovisual/digital data feeds and/or other quantitative, semi-quantitative, and qualitative data feeds from a live OR or other patient intervention areas onto a single interface.

Hardware Unit

The encoder connects to one or more data capture devices that may be grouped as a hardware unit 20 (FIG. 1) to monitor activities (and capture data representing the monitored activities) within the OR or other patient intervention area.

The hardware unit 20 may be located the OR or other patient intervention area. For example, several pieces of recording equipment may be installed in the OR/patient intervention area, e.g., as follows: wall-mounted wide-angle lens room cameras to allow visualization of the entire room, several cardioid microphones to capture details of all conversation/noise/alerts in a quality that allows analysis, a procedural video capture device (endoscopic camera, x-ray, MRI etc.), and a vital signs monitor device and sensors (environmental, acoustic, electrical, flow, angle/positional/displacement and other), medical/surgical devices, and implants. The hardware unit (e.g., grouping of data capture devices) interface with middleware hardware devices and an encoder to connect and synchronize device feeds. Integration of the platform 10 may be non-intrusive in the OR, with minimal equipment set-up. The anesthesia and laparoscopic feeds may be streamed in the OR, and the microphones and room cameras may be installed without altering the infrastructure of the room, for example.

Room Cameras

Figure 3:
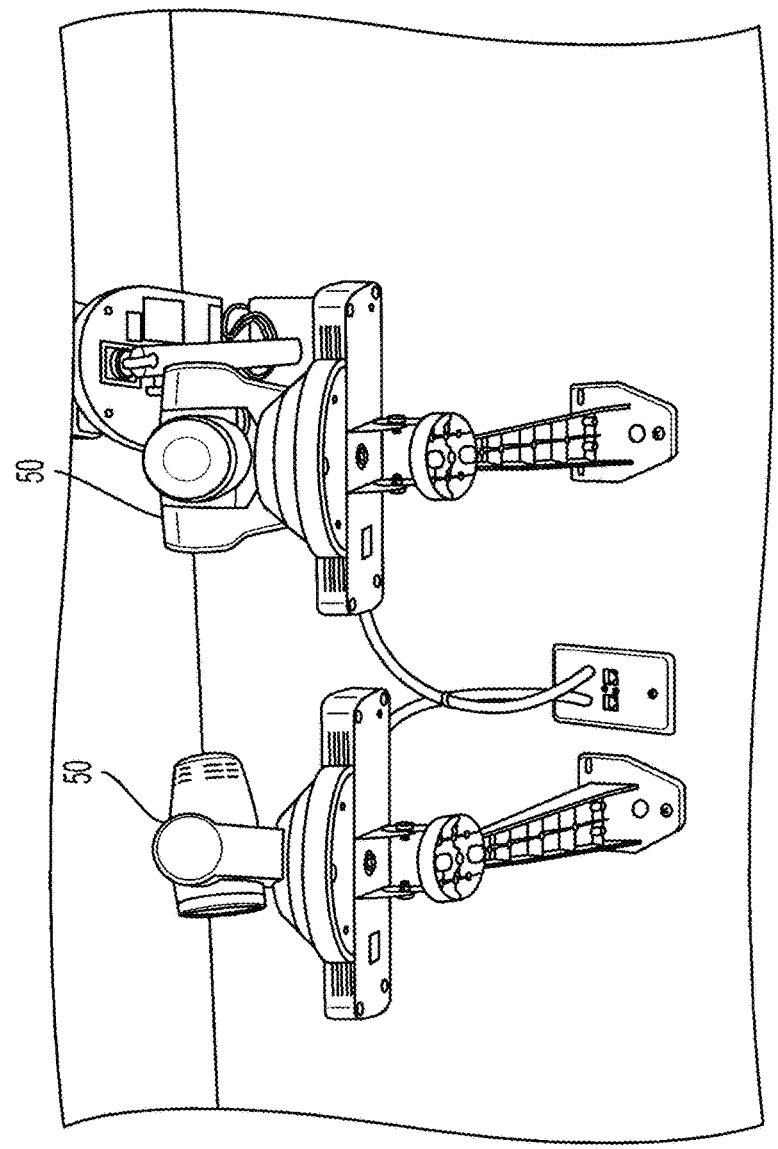
FIG. 3 illustrates a schematic of example wide-angled video cameras according to some embodiments.

According to some embodiments, hardware units 20 may have cameras 30 (FIG. 1). FIG. 3 shows a schematic of example wide-angled video cameras 50 according to some embodiments. For example, two wide-angle cameras 50 (EVI-HD1, SONY, Tokyo, Japan) may be installed to capture data representative of an entire view (e.g., 180 degrees or more) of the room. As an illustrative example, the room cameras 50 may be mounted above a nursing station and focused on the operating table, with the aim of capturing the surgical team in the field of view. Both entrances to the room may be in the field of view, which allows for measuring foot traffic by recording the opening and closing of doors and number of individuals present in the room.

Microphones

Figures 4A, 4B, 4C:
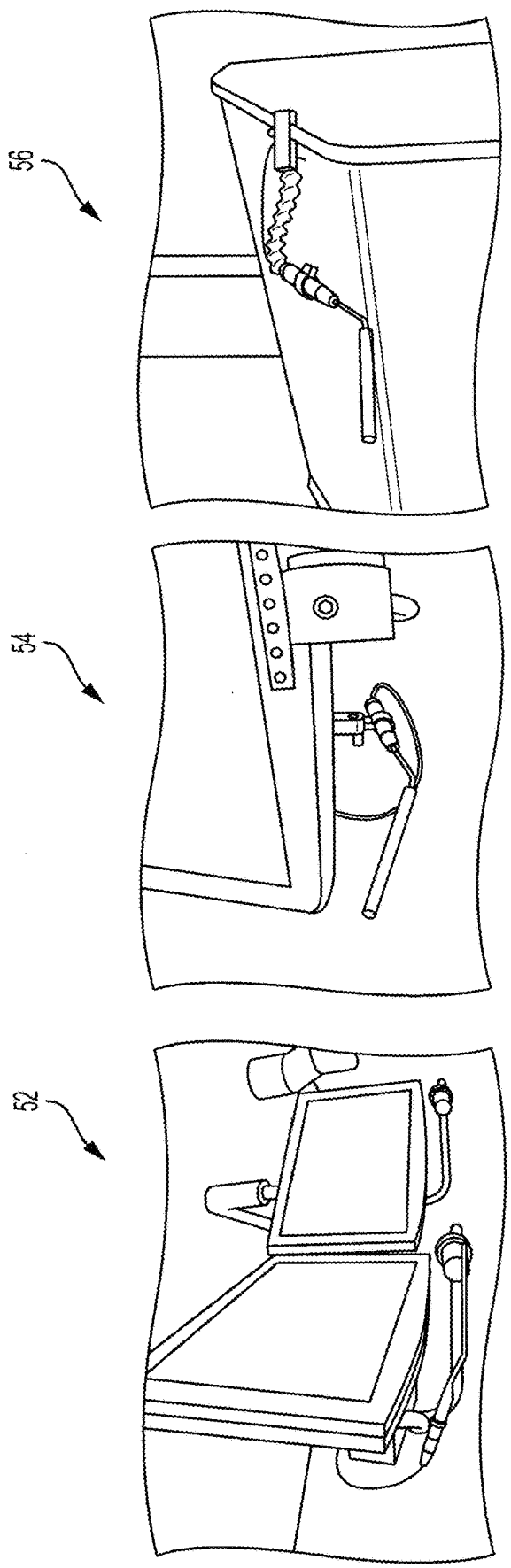
FIGS. 4A, 4B and 4C illustrate a schematic of example microphones according to some embodiments.

According to some embodiments, hardware units 20 may have audio capture devices 32 (FIG. 1). FIGS. 4A, 4B and 4C show a schematic of example audio capture devices as three directional microphones 52, 54, 56 (e.g., MicroLine® Condenser Gooseneck Microphone, ES935ML6™, Audio Technica™). The microphones 52, 54, 56 may be installed to capture audio communication within the OR or proximate thereto with the range of the microphones 52, 54, 56. Prior to installation, live surgical procedures may be observed in the OR or other patient intervention area to identify areas, locations or regions of high-frequency communication and to assess primary sources of ambient noise, such as alarms of medical equipment, periodic tones of the anesthesia machine, and/or noisy voices from intercom. The observation may be used to determine positioning or set-up of the microphones 52, 54, 56. Different microphone set-ups may be tested by simulating the noises of a surgical procedure in a vacant OR or other patient intervention area, and a set-up may be selected for audio quality. According to some embodiments, microphones 52, 54, 56 may be set up in two locations or more within the OR: (1) on the infield monitors (e.g., microphones 52, 54), directed towards the surgical field, and (2) above the nursing station (e.g., microphone 56), directed towards the scrub nurse and equipment cart. Each audio source may be recorded onto a separate independent feed, with the option of mixing audio feeds post-recording. They may be directional microphones mounted on infield laparoscopic monitors and above a nursing station, for example.

Procedural Camera View

Figure 5:
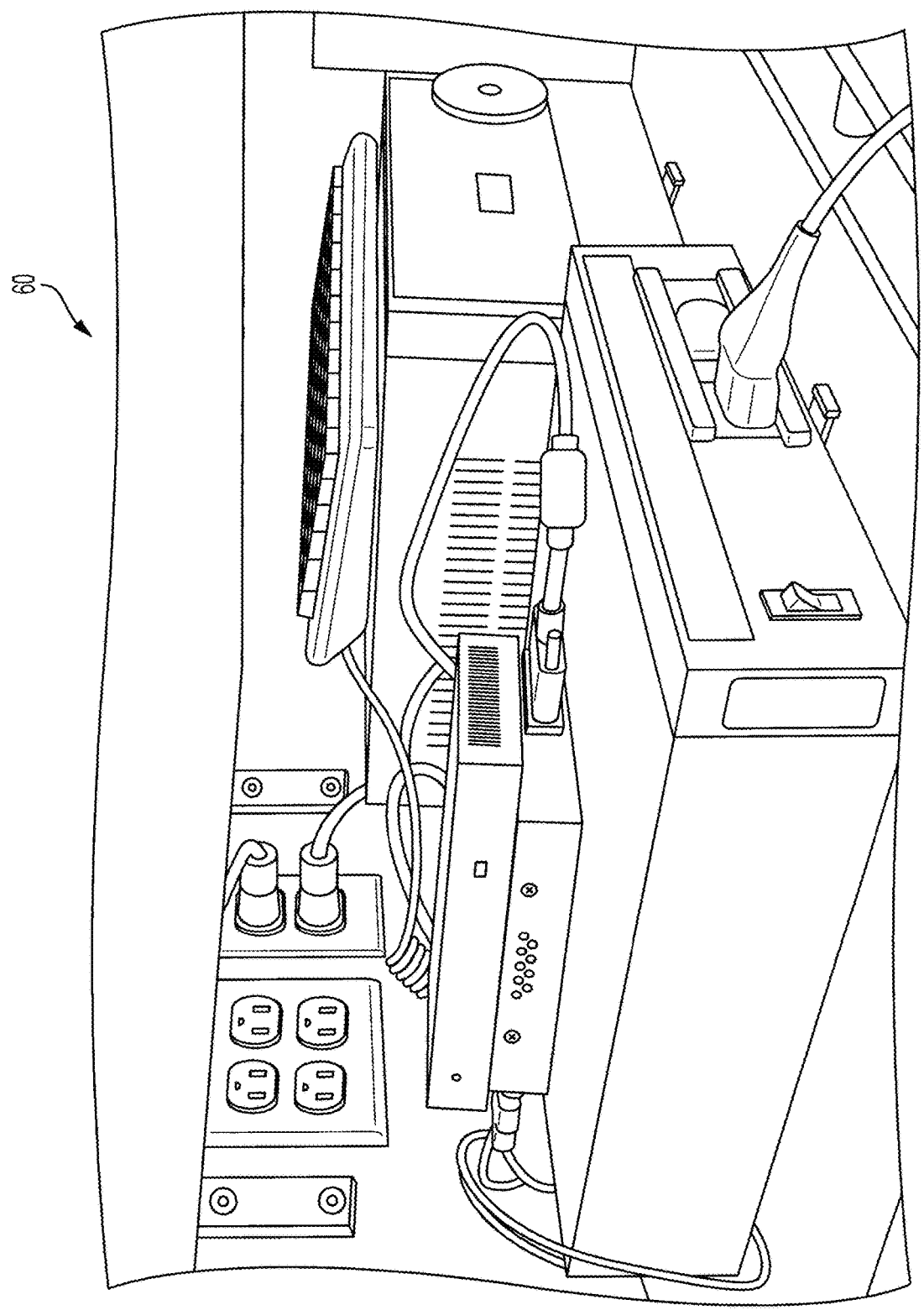
FIG. 5 illustrates a schematic of an example Distribution Amplifier and Converter according to some embodiments.

According to some embodiments, hardware units 20 may have cameras 30 (FIG. 1) that provide procedural camera views. The laparoscopic camera view may be recorded as part of diagnostic care in the OR on a separate stand-alone machine (AIDA™, Karl Storz™). To incorporate this video feed into the black-box recording device or encoder, a distribution amplifier (DA) may be used to split the video signal—allowing one signal to be displayed on the infield monitor during the operation and the other to be streamed into the black-box recording device or encoder. The DA may also ensure that the aspect ratio of the black-box laparoscopic recording corresponds to a 16:9 aspect ratio of the infield monitor, in some example embodiments. The video feed may be recorded in high-definition. FIG. 5 shows a schematic of example video hardware 60 including a DA used to split the video signal from a camera 30 used for diagnostic care and a converter used to convert the video signal to proper video format for the encoder.

Anesthesia Device

According to some embodiments, hardware units 20 may have patient monitor devices 36 (FIG. 1). For example, patient monitor devices 36 may include an anesthesia machine monitor that may be used to observe physiological data of the patient in real-time and to detect abnormal changes in patient vital signs. According to some embodiments, the vital sign display may be extracted from the anesthesia machine using a video card, which generates a secondary feed of VGA output. The vital sign video feed may be converted from VGA to HD-SDI format using a converter unit (VidBlox 3G-SL, PESA, Huntsville, Alabama, USA), prior to integration and synchronization with the other video feeds.

In some embodiments, there may be extraction of raw digital data from the anesthesia device directly for provision to encoder 22 which ingests it as metadata.

Additional Sensors

According to some embodiments, hardware units 20 may have sensors 30 (FIG. 1) installed or utilized in a surgical unit, ICU, emergency unit or clinical intervention units. Example sensors include but are not limited to: environmental sensors: i.e. temperature, moisture, humidity, etc.; acoustic sensors: i.e. ambient noise, decibel, etc.; electrical sensors: i.e. hall, magnetic, current, mems, capacitive, resistance, etc.; flow sensors: i.e. air, fluid, gas, etc.; angle/positional/displacement sensors: i.e., gyroscopes, attitude indicator, piezoelectric, photoelectric, etc.; other sensors: strain, level sensors, load cells, motion, pressure, etc.

Hardware Unit Integration into the Operating Room

Figure 6:
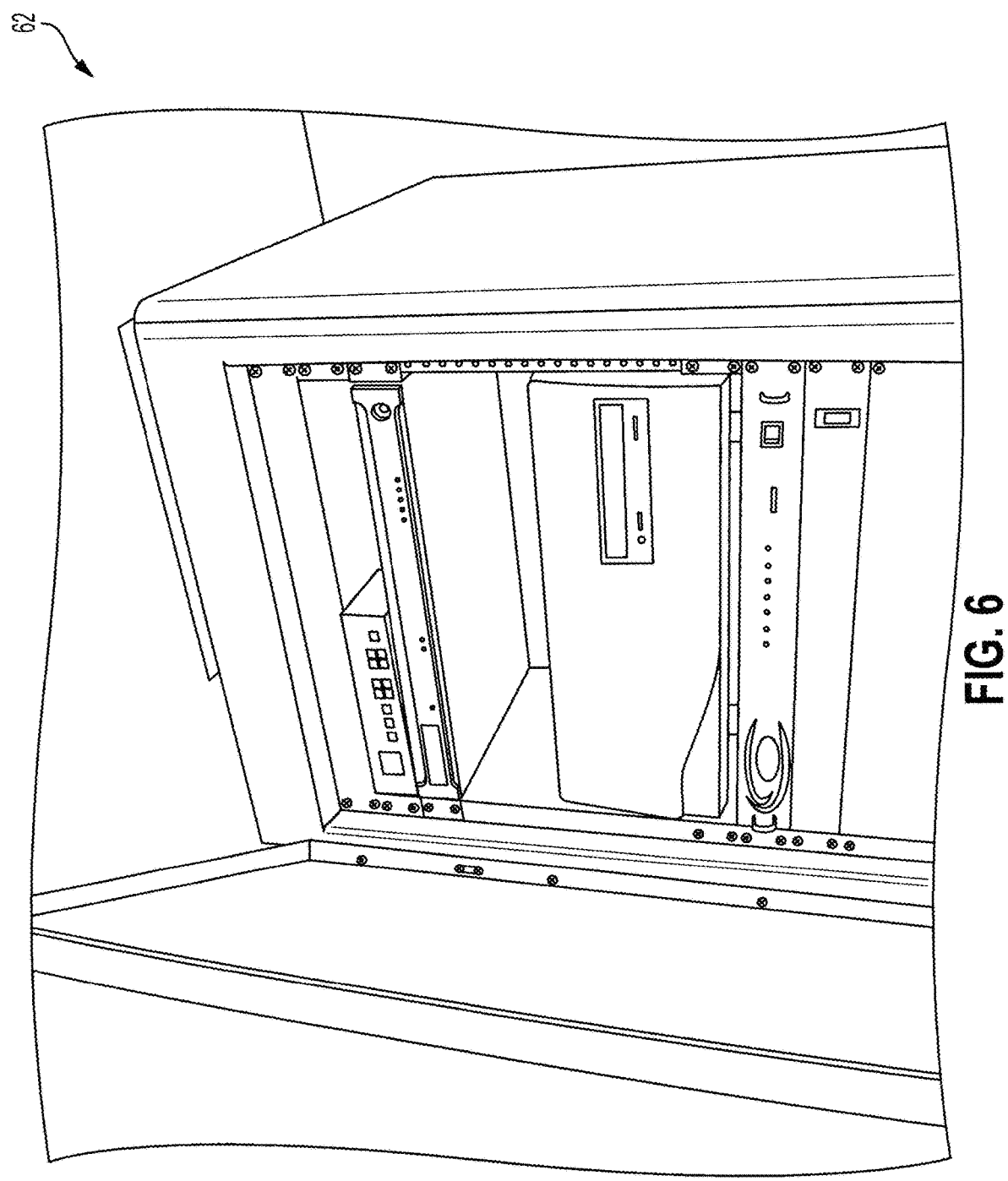
FIG. 6 illustrates a schematic of an example central signal processor according to some embodiments.

According to some embodiments, hardware units 20 may have a signal processor coupling data capture devices. FIG. 6 illustrates a schematic of a digital signal processor 62 according to some embodiments. According to some embodiments, video and audio data signals may be fed into a signal processor 62, which may be remotely located in a rack within the sterile core of the OR. The signal processor 62 may be able to support multiple video/audio signals and digital data ingested as metadata. The signal processor 62 may be responsible for collecting audio and video signals from multiple independent data feeds or streams, and encoding them to a compressed format.

Figure 10A:
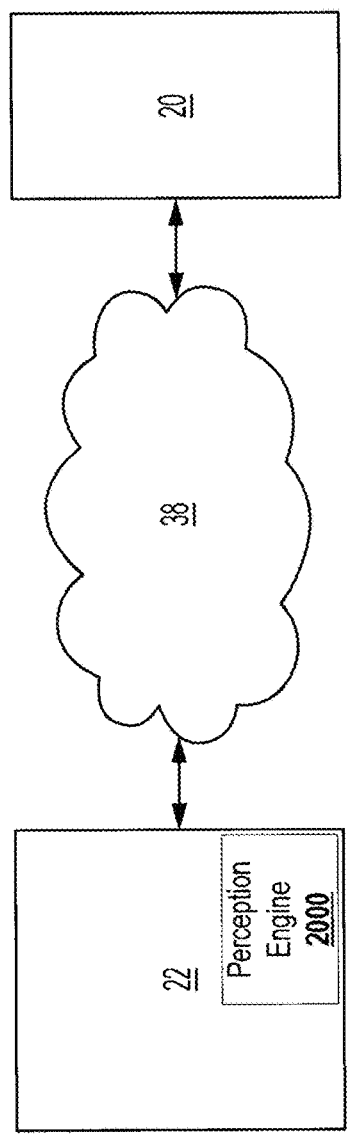
FIG. 10A illustrates a schematic of an example network according to some embodiments.

FIG. 10A illustrates a simplified architecture of encoder 22 coupling to hardware unit 20 via network infrastructure 38. This may be a direct or indirect network connection. In some embodiments, the encoder 22 includes a perception engine 2000 utilized for applying machine-learning and generate the interface indicator elements as described here. For example, the interface indicator elements may include a visual representation of a time line and indicators for different clinical events along the timeline, where the events may relate to predicted errors or events as described herein. The clinical events may be detected and extracted from the session container file.

Figure 10B:
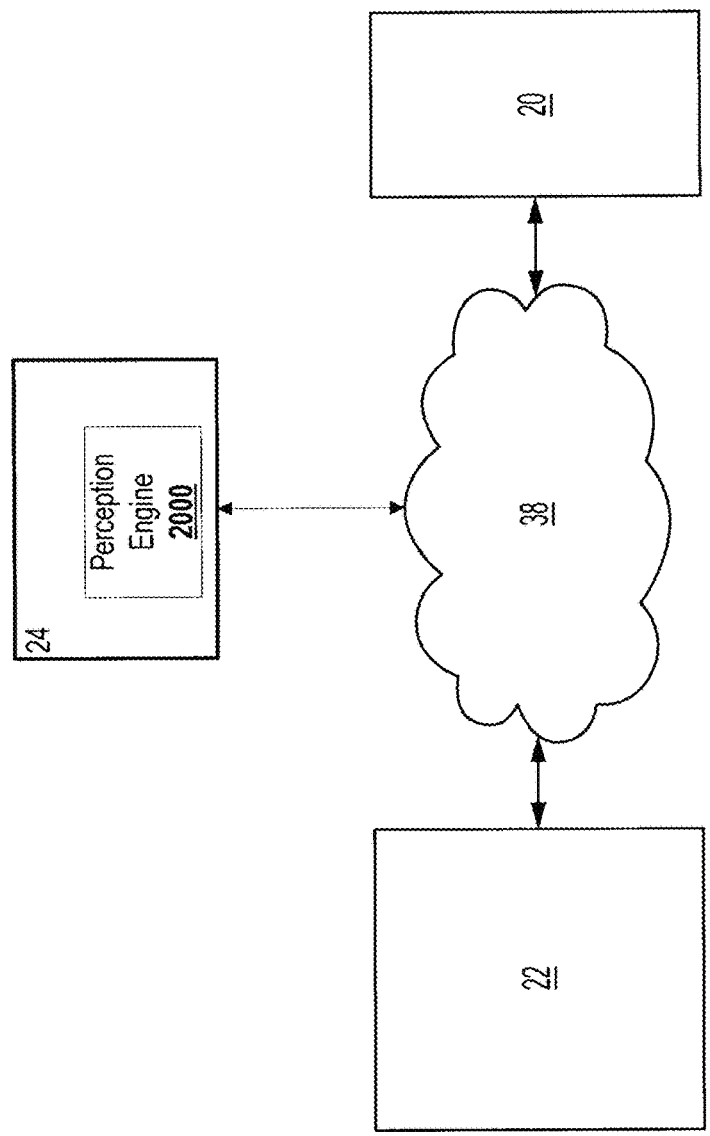
FIG. 10B illustrates an alternate schematic of an example network according to some embodiments.

FIG. 10B illustrates an alternate schematic of an example network according to some embodiments. In FIG. 10B, the perception engine 2000 is depicted to be included on a remote server 24, which may, in some embodiments, include servers provided through remote-networking communication links, distributed computing resources (e.g., "cloud computing"), etc. Advantages of the use of remote and/or distributed resources include greater availability of computing resources (e.g., memory, processing power), isolation from potential emergencies, secure storage of sensitive data, etc.

For larger application environments and to maximize efficiency and deliver increased fail-over and redundancy capabilities, a switching router may be used (e.g., router 16 of FIG. 1). Audio, video and data feeds may be connected by network infrastructure such as a cable or via connected wireless base station to a switching router 16 (FIG. 1). An example purpose of the router may be to route audio, video and data feeds to one of multiple encoders 22 available on the network. The use of multiple encoders coupled to a router 16 may provide for more cost effective implementation, greater spatial coverage and increased redundancy and fail-over for the system. Accordingly, the network infrastructure shown in FIG. 10 may include one or more switches or routers. Further, although only one encoder 22 is shown for simplicity there may be multiple encoders connecting to one or more hardware units 20 via network infrastructure 38. Although only one hardware unit 20 is shown for simplicity there may be multiple hardware units 20 connecting to one or more encoders 20 via network infrastructure 38.

Figure 11:
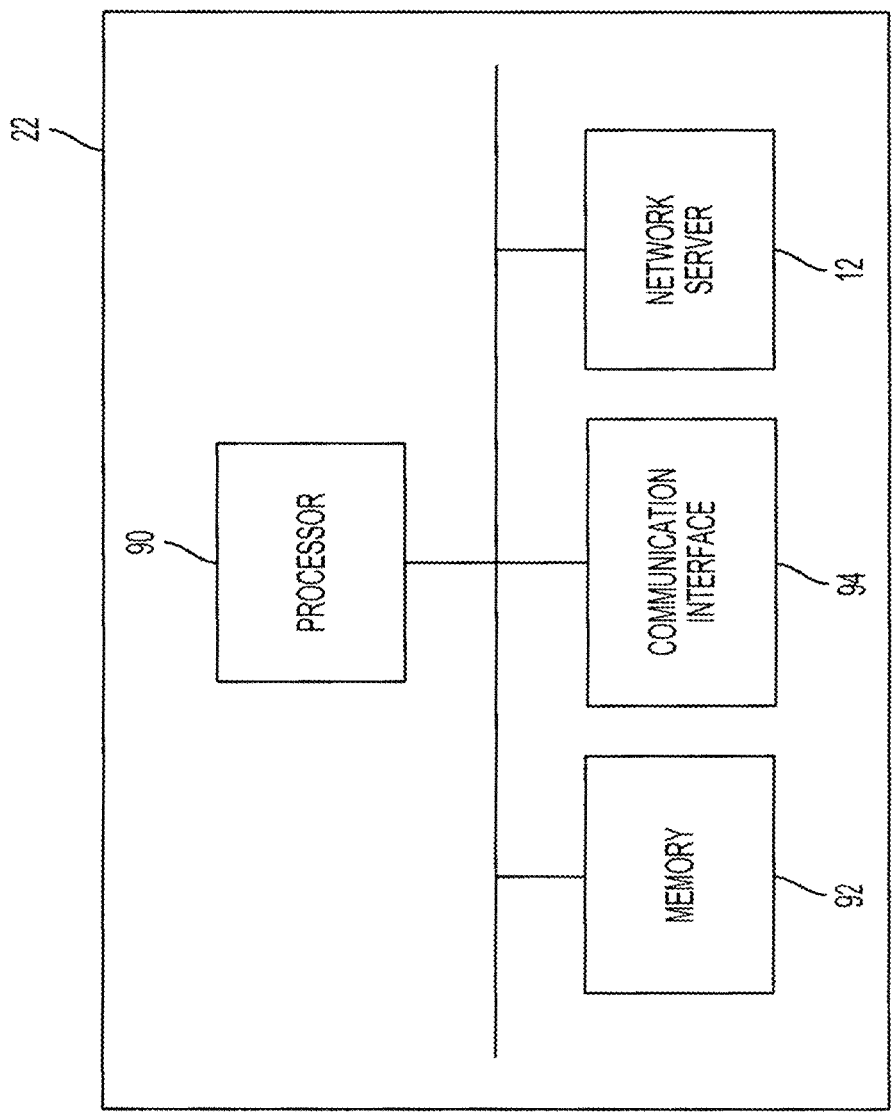
FIG. 11 illustrates a schematic of an example encoder according to some embodiments.

FIG. 11 illustrates a schematic diagram of an encoder 22 according to some embodiments.

For simplicity only one encoder 22 is shown but system may include more encoders 22 to collect feeds from local or remote data capture devices (of hardware unit 20) and exchange data. The encoders 22 may be the same or different types of computing hardware devices. The encoder 22 has at least one processor, a data storage device (including volatile memory or non-volatile memory or other data storage elements or a combination thereof), and at least one communication interface. The encoder 22 components may be connected in various ways including directly coupled, indirectly coupled via a network, and distributed over a wide geographic area and connected via a network (which may be referred to as "cloud computing").

For example, and without limitation, the encoder 22 may be a server, network appliance, embedded device, computer expansion unit, personal computer, laptop, mobile device, tablet, desktop, or any other computing device capable of being configured to carry out the methods described herein As depicted, encoder 22 includes at least one processor 90, memory 92, at least one communication interface 94, and at least one network server 12. In some embodiments, encoder 22 is configured for use as a perception engine 2000, among other uses and/or configurations.

Each processor 90 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. The processor 90 may be configured as described herein to synchronize the collected data fees to generate a container session file. The processor 90 may also implement anonymization and encryption operations, as described herein.

Memory 92 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

The communication interface 94 may include an I/O interface component to enable encoder 22 to interconnect with one or more input devices, such as a keyboard, mouse, camera, touch screen and a microphone, or with one or more output devices such as a display screen and a speaker. The communication interface 94 may include a network interface component to enable encoder 22 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, private network (including VPN 24), local area network, wide area network, and others, including any combination of these. These are examples of network infrastructure (e.g., network infrastructure 38 of FIG. 10)

Figure 12:
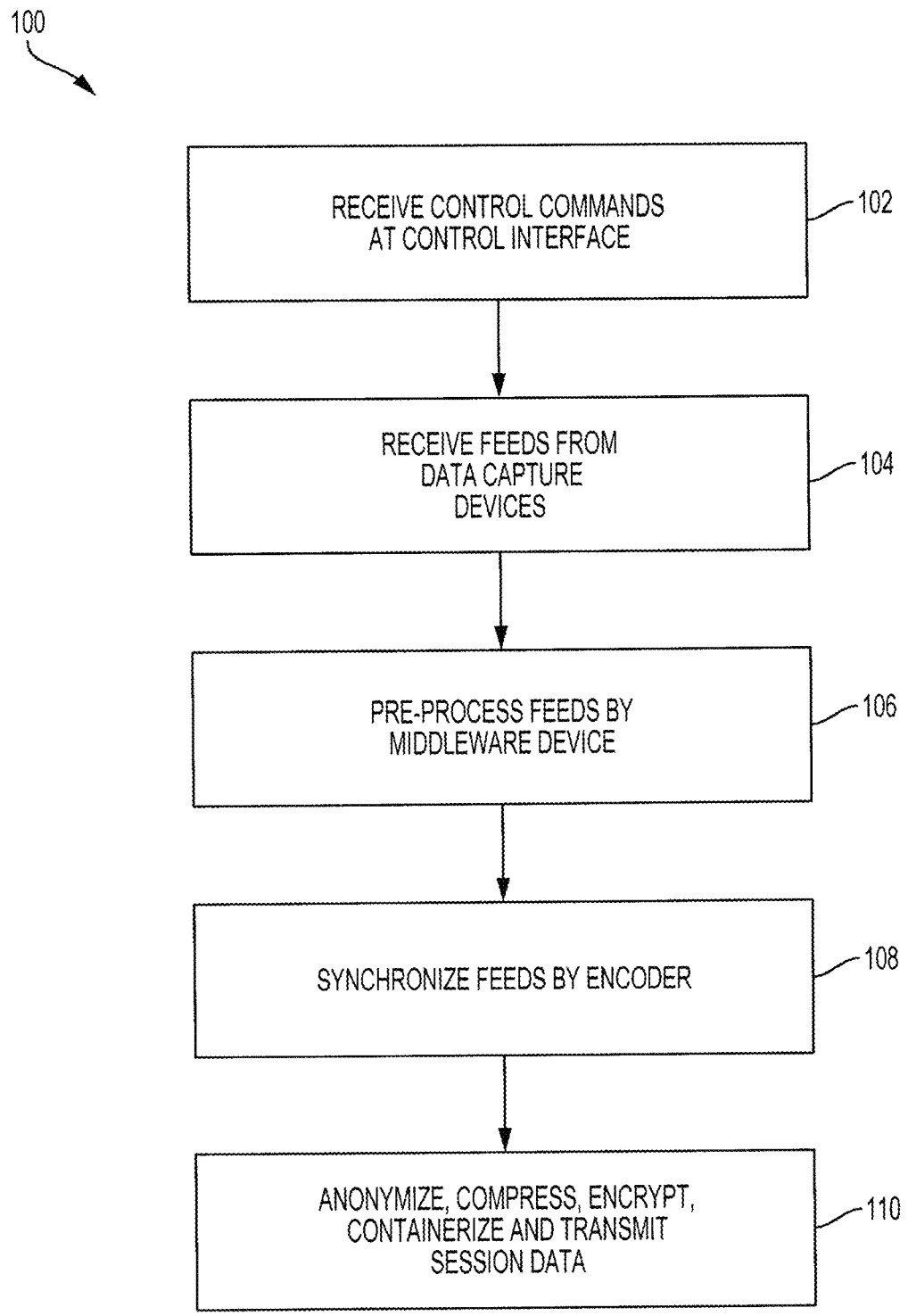
FIG. 12 illustrates a flow chart of an example method according to some embodiments.

FIG. 12 illustrates a flow chart diagram of a method 100 for collecting medical and surgical data according to some embodiments.

At 102, using the Customizable Control Interface 14 and GUI, a control command for activation of the system may commence recording, collection and streaming of all available audio, video and data feeds from data capture devices to one of multiple available encoders 22 via the switch router 16. The data capture devices may include a portion or all available cameras including both mounted and laparoscopic, all audio microphones and all available and implemented sensors and third-party devices (open or proprietary) used in a surgical unit, ICU, emergency or other clinical intervention unit. Pause/Stop/Play are additional control commands received at Control Interface 14 which may trigger transmission of corresponding commands to the encoder 22 to control recording.

At 104, in response to the control commands, data capture devices of hardware unit 20 capture data representing various aspects of the OR or other medical unit and generate feeds or data streams for provision to encoder 22. Various example data capture devices are described herein.

At 106, digital data may be formatted, translated and synchronized through middleware hardware and software and using networking protocols for clock synchronization across the network. Digital data will be ingested into the encoder 22 as Metadata.

At 108, the encoder 22 may be responsible for synchronizing all feeds to generate session recording, as described herein.

At 110, the encoder 22 may encode synchronized feeds into a signal transport file using lossless audio/video/data compression software. According to some embodiments, the encoder 22 may also be responsible for hosting (or storing) and operating anonymization and voice/vocabulary distortion software(s) for the purpose of protecting the identity of all medical professionals, patients, distinguishing objects or features in a medical, clinical or emergency environment. This may be done by encoder 22 either before compression, containerizing and encryption, or after decrypting in back office system.

Upon completion of the recording, at 110, the container file may be securely encrypted by encoder 22. Encrypt/decrypt keys may either be embedded in the master session container file and accessible through a master key, or have a separate key.

The encrypted file may either be stored on the encoder 22 (e.g., network server 16 of FIG. 1) or stored on a Storage area network until scheduled transmission. The communications or network server 16 on the private VLAN may be responsible for schedule management and the automated file and key transmission. This may be done through a private VLAN on the client environment and transmitted via Virtual Private Network (VPN) (e.g., VPN 24 of FIG. 1) on public data lines directed back to back end office. The communications server 16 may be responsible for backing up data including audio, video, data, encrypted files, etc utilizing backup software as part of the configuration. The communications server 16 may be responsible for hosting and directing all traffic between the private VLAN and back office.

According to some embodiments, the synchronized compressed encoded signals may be fed into a touchscreen monitor located inside the OR, which may be responsible for real-time visual display of feeds and direct recording onto an external hard-drive.

Control Interface

According to an embodiment, a user interface may be provided on a PC-based touchscreen monitor. The user interface may be referred herein as a Control Interface 14 (FIG. 1) and may serve as a "central control" station that records video and audio feeds in real-time, and transmits control commands to the encoder 22. The Graphical User Interface (GUI) and its parameters may incorporate principles of UI design to provide an interface is simple, user-friendly and functional.

According to an embodiment, the features of the Control Interface 14 providing the central control station (e.g., computer, tablet, PDA, hybrid, convertible) may be located in the clinical unit or another customer designated location. It contains a customizable graphical user interface (GUI) that provides a simple, user friendly and functional control of the system.

According to an embodiment, the Control Interface 14 may have a Play/Pause button. Some segments of the procedure may not need to be recorded. To skip these segments from the recording, the user interface may pause and restart the recordings when desired by way of control commands generated in response to activation of the play/pause button. The pause and play time-stamps may be recorded in a log file, indicating the exact times of the procedure that were extracted.

According to an embodiment, the Control Interface 14 may have a Stop session button. When the "stop session" button is selected, files may be closed and automatically transferred to the storage area network (SAN), encoder 22, and so on.

According to an embodiment, the Control Interface 14 may have split-screen quadrant display of video feeds. Visual displays of videos may be provided in real-time during recording.

According to an embodiment, the Control Interface 14 may have a visual indicator of recording. For example; a red, blinking dot may appear on screen to provide visual indication to the team that video and audio feeds are being recorded.

According to an embodiment, the Control Interface 14 may have a log file. At the end of the recording, a log file may be generated that indicates key time points, including start and end of the recording session, pauses and replays.

According to an embodiment, the Control Interface 14 may have password protection. The interface may be secured with several layers of password protection to ensure maintenance of patient confidentiality and privacy.

Figure 7B:
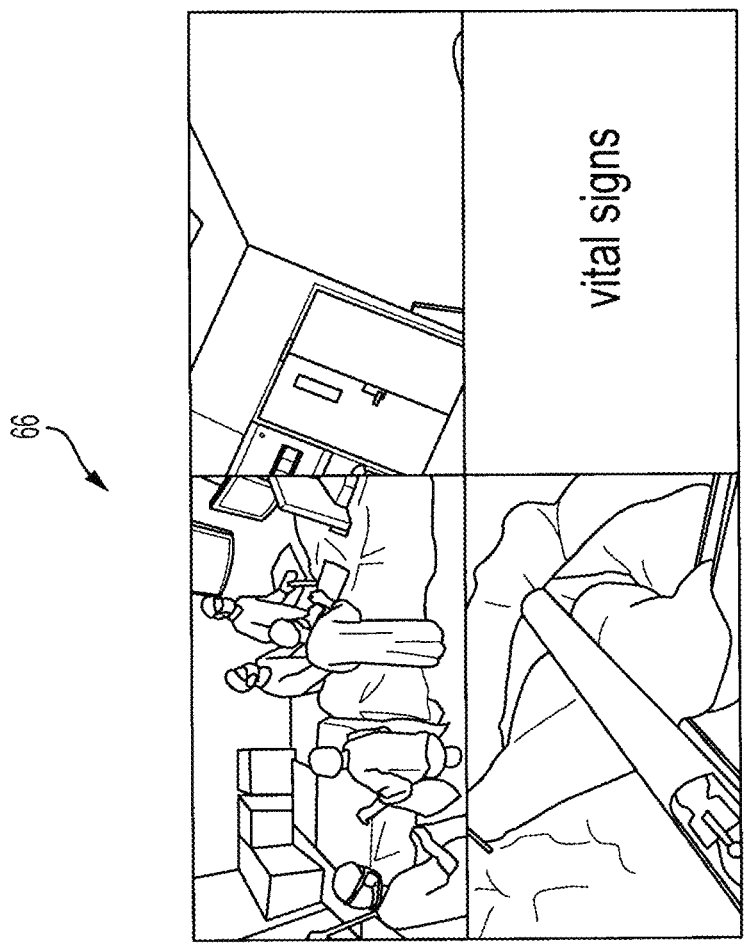
FIGS. 7A and 7B illustrate a schematic of an example touchscreen monitor according to some embodiments.
Figure 7A:
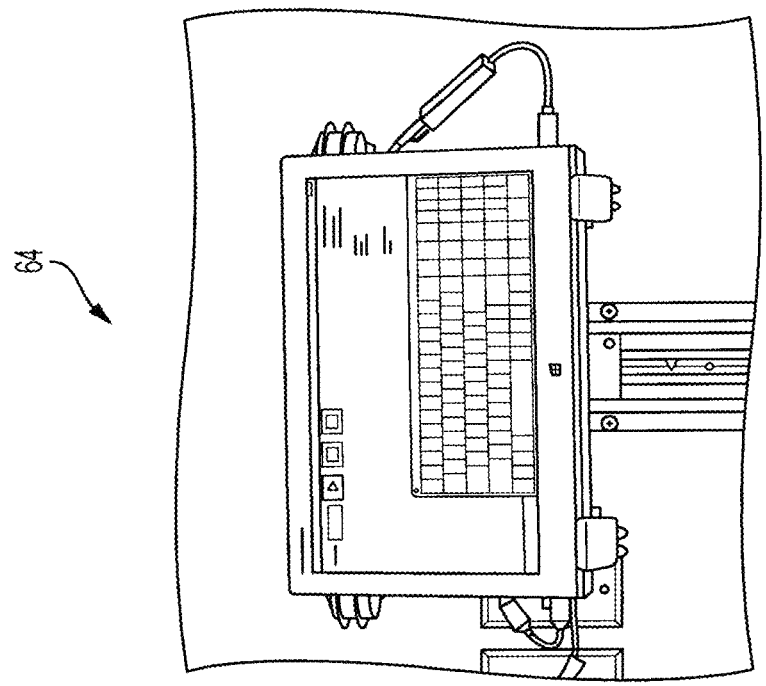

FIGS. 7A and 7B illustrate an example schematic of the Control Interface according to some embodiments. The Control Interface 14 may provide a control screen 64 for a touchscreen monitor (of a tablet device) with password protection. The Control Interface 14 may provide a display screen 66 with multiple views of the OR from multiple feeds from data capture devices located within the OR.

Figure 8:
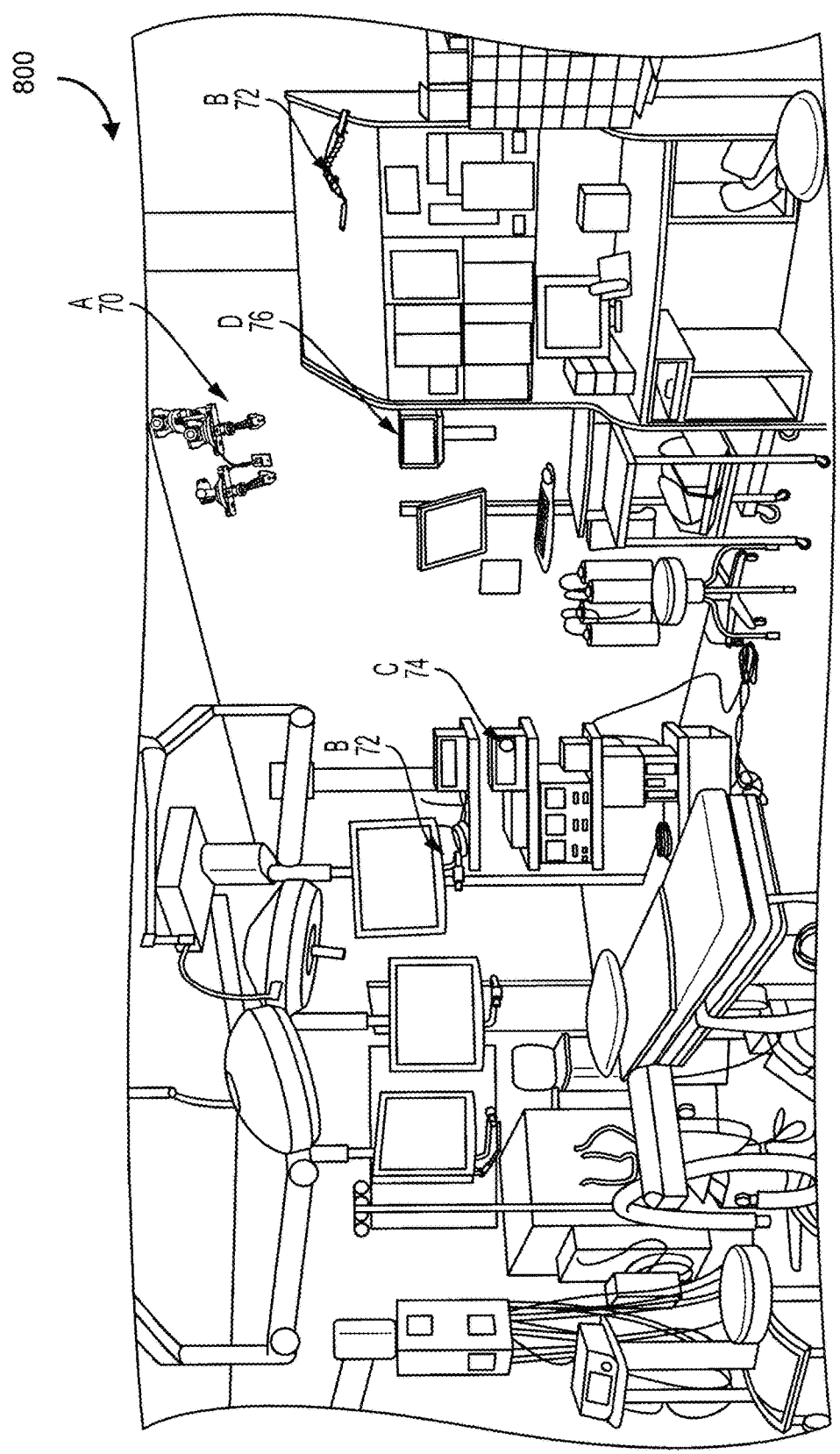
FIG. 8 illustrates a schematic of an example view according to some embodiments.

FIG. 8 illustrates an example schematic of an Operating Room (OR) 800 integrated with a hardware unit of data capture devices to capture data representative of different views of the OR 800. The data capture devices for this example illustration include room cameras 70, microphones 72 (located at infield monitors and above nursing station), distribution amplifiers and video convertor 74 used to process laparoscopic video signal, and touchscreen monitor 76 that controls recording via control commands.

Rich Content Analysis Unit (i.e. Video Analysis Software)

The Rich Content Analysis unit facilitates the ability to process, manage, review, analyze and tag multiple formats of rich content (for example, video, audio, real-time patient meta-data such as heart rate, and so on) in synchronization.

The Rich Content Analysis unit may provide, for the user (i.e. the medical professional, surgical expert or medical researcher), an intelligent dashboard which allows for the annotation and tagging of the rich content streams. That is intelligent dashboard may be an interview with playback viewing for reviewing content and interface controls for tagging content. The intelligent dashboard may be multi-dimensional in that the union of all dimension variables (i.e. case variables) may indicate a specific set of one or more applicable annotation dictionaries (i.e. coding templates). Some examples of the variables that may be used to determine the annotation and tagging dictionary may be: the type of medical procedure being performed (e.g., Laparoscopic Bypass), the aspect of the procedure that is being analyzed (e.g., technical skills, non-technical skills, and so on), the geographic area/region where the procedure is being performed (this may dictate a regional specific annotation dictionary that is mapped to a generalized globally accepted dictionary), and so on. These are example variables.

The Rich Content Analysis unit may implement a data model and cross reference between annotation dictionaries (i.e. coding templates) that span various medical procedures, country/regional interpretations, and so on. Each annotation dictionary may allow the entire rich content stream to be tagged (i.e. allows for the creation of descriptive content) in synchronization. For example, the content streams may be tagged with well-formed descriptors that are applicable to different objectives of analysis. For example, an annotation dictionary may allow for the tagging of Technical Skills (an example objective of the analysis) such as Suturing Error or Stapling Error (i.e. the tags) and tag every instance in the rich content stream where these types of errors may have occurred.

Rich content refers to multiple streams of content in various formats (audio, video, numeric data, etc.). The union of all Case Variables may require multiple annotation dictionaries—either custom made or based on previously validated rating tools—to assess different aspects of the procedure and recoding, including, but not limited too technical performance, non-technical performance, non-procedural errors and events, and human factors. Each annotation dictionary may be a well-formed relational dataset.

Another feature of the Rich Content Analysis unit is that the final aggregation of the entire rich content stream and the entire descriptive content (for example, the Technical Skills annotation/tagging, the Non-Technical skills annotation/tagging, and so on) can be reviewed in synchronization post aggregation.

The Rich Content Analysis unit may be disseminated with web technologies to ensure that the content is centrally hosted in a secure, healthcare institution approved environment. For each aspect of the procedure that is being analyzed, the Rich Content Analysis unit may ensure that only the applicable rich content streams are played simultaneously on a single user interface (for example, when rating the purely technical skills of the surgeon, the audio feed from the operating room would not be applicable). The Rich Content Analysis unit may provide numerous customizations that are again only made available depending on the aspect of the procedure being analyzed. These customizations include, but are not limited to: the ability to increase the granularity of any content stream (for example, enlarge or reduce the size of a video stream), control the playback speed of any content stream (e.g., increase or decrease the playback speed of a video), refine the quality of a content stream (e.g., apply filtration functions to increase the clarity of an audio stream).

Black Box Encoder Analytics Unit (i.e. the Black Box Database)

The Black Box Encoder Analytics unit may provide the second part in a two part handshake between the Rich Content Analysis unit. The Black Box Encoder Analytics unit may contain quantitative and qualitative analysis processes to facilitate reporting capabilities, including but not limited to, comparative analysis, benchmarking, negative trends, data mining, statistical reporting, failure analysis and key-performance indicators. The Black Box Encoder Analytics unit may also facilitate aspect based integration to statistical software research tools such as Matlab.

An example feature of the Black Box Encoder Analytics unit may be its relational database that captures and cross-references the entire dataset composition which includes, but is not limited to: the complete resultant annotated and tag content streams produced by the Rich Content Analysis software identified with structured meta-data such as the Technical Procedural Rating System for Laparoscopic Bypass, and so on; facility variables such as Department, Operating Room, and so on; procedure case variables such as urgency of the case, number of medical staff present and what their designation is, and so on; procedure case notes (in a structured well-formed relational data model) such as what kind of stapler was used, was hemostatic agent used, and so on; patient centric data such as blood work; and OSATS scores.

In addition to the example reporting capabilities listed, the Black Box Encoder Analytics unit may provide visual comparative analysis. The dataset can, in its entirety or a subset of, be displayed on a visual timeline that is distributed by relevant meta-data such as components of the annotation dictionary (e.g., Technical Errors) or Case Variables.

Visual comparative analysis may provide example benefits, including but not limited to: the ability to review errors and events and determine preceding and trailing actions and observations; the ability to define, execute and convert visual observations into programmatic algorithms that can be executed on large groups of annotated content. For example, identifying, programmatically where a cluster of technical errors leads to a more serious technical event; the ability to baseline, benchmark, and refine inter-rater (i.e. content stream analyzer/reviewer) reliability by comparing timelines of different observers; the ability for medical teams to assess the cause of a major adverse event in a specific case—e.g., human error, medical device malfunction, and so on.

Another example feature of the Black Box Encoder Analytics unit is its dual purpose ability to improve patient outcomes with continuous improvement using healthcare intelligence analytics defined in the Black Box Analytics software. For example, the identification of small, unnoticed, possibly minor actions which may have led to a serious outcome; and support continuous improvement through additional research initiatives by integrating with research related software tools such as Matlab™ and providing research driven comparative analysis—for example, comparing a specific outcome using "Year 1" vs. "Year 2" research model.

Illustrative Example Applications

An illustrative example embodiment of the black-box recording device may involve: two wall-mounted high-definition wide-angled cameras; two omnidirectional microphones; a laparoscopic camera view; and a vital signs display. These are example data capture devices of a hardware unit. This example application may use an Internet Protocol ("IP") network in which each data signal may be fed into an Ethernet switch ("ES"). The purpose of the ES may be to create a local area network (LAN) that establishes a central connection point for all sources. Before connecting to the ES, each data feed may be assigned its own Internet Protocol (IP) address. The video cameras and corresponding microphones may be IP-based with built-in encoders, while the laparoscope and anesthesia feeds may first run through an additional encoder device that converts the analog or digital video signals into a real-time streaming protocol (RTSP) video stream. The data signals may be bundled at the ES and directed to a touchscreen user interface on a PC-based platform (Patient Observation System, "POS"). The POS may be responsible for decoding the data into a readable signal, and synchronizing data feeds.

In some IP networks, video and/or audio feeds may be streamed separately through the network, from endpoint to endpoint, which may create opportunities for network delays along the streaming path. Over time, delays between video and audio feeds may accumulate, and/or each feed may experience different network delays. Delays may be unknown and/or constantly changing over time, and/or it may be difficult to quantify and/or account for delay and/or results in an effect called "drifting". Another example embodiment of the black-box platform may be provided without the same IP-networking functionality of the example discussed above. Another example embodiment may use a self-clocking signal processor with synchronized micro-encoders. According to the example embodiment, the self-clocking signal processor may ensure that the audio and video streams are "locked" without drifting, and thus allowed the feeds to be shifted post-recording to achieve synchronization.

A further example embodiment of the black-box system may use omni-directional microphones, placed above the operating table and at the equipment boom, in an attempt to capture audio surrounding the surgical field. However, omni-directional microphones may have equal output/input at all angles, and/or may detect sound from all directions. These microphones may have resulted in suboptimal and/or inferior audio quality, with excessive background noise and poor detection of team communication.

In another example embodiment of the black-box system, directional cardioid microphones may be used which are sensitive at the front and isolated from ambient sound. These microphones may be placed on the infield monitor, directed towards the surgical field, where communication exchange may be likely to occur among the surgical team. This set-up may result in superior audio quality with clear detection of voices and sounds.

Figures 9A, 9B:
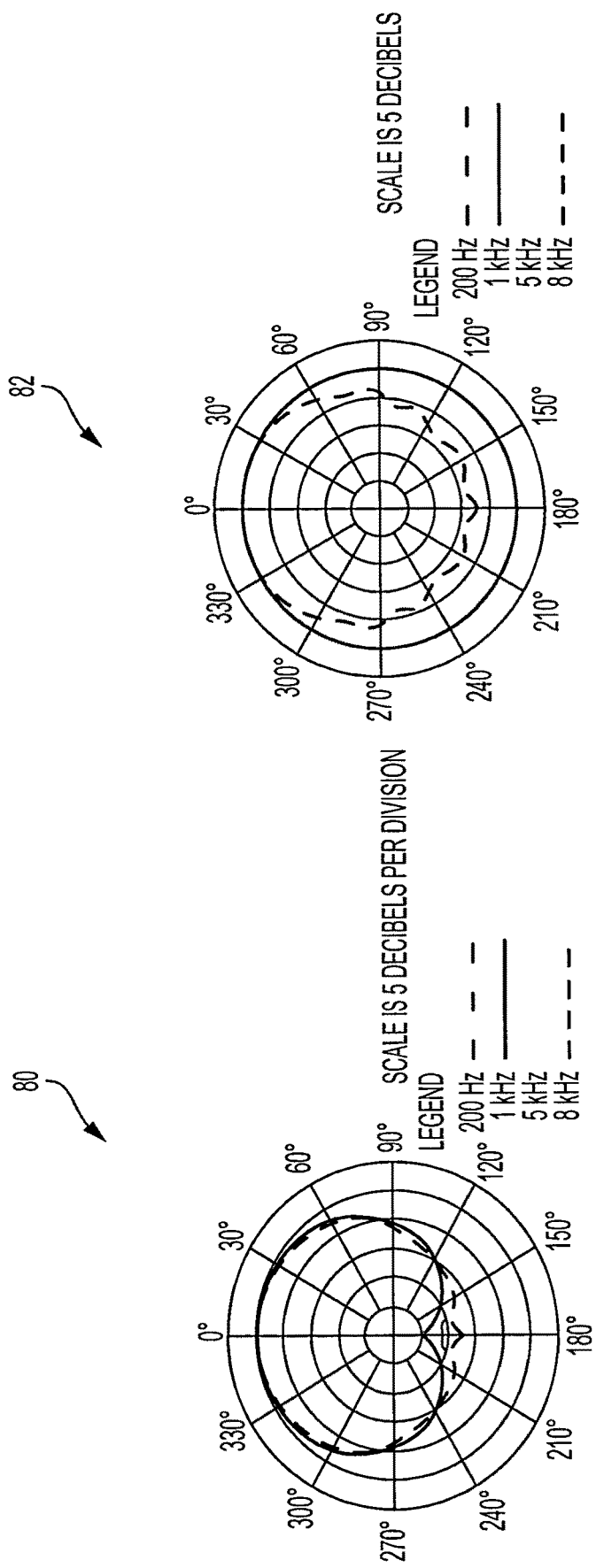
FIGS. 9A and 9B illustrate a schematic graph for polar patterns according to some embodiments.

FIGS. 9A and 9B illustrate an example schematic graph 82 of polar patterns of omni-directional and an example schematic graph 80 of polar patterns of cardiod microphones. As shown in graph 82, omni-directional microphones may have equal sensitivity at all angles. As shown in graph 80, cardioid microphones may be directional with more sensitivity at the front and less at the back.

According to embodiments described herein, a synchronized multi-channel video/audio/metadata recording platform may be for use in the intraoperative environment. Development and installation of the black-box platform may be an iterative process that may involve both minor and major changes to the system.

While other industries such as television broadcasting may have equipment to capture video and/or audio, according to some embodiments, the "black box" platform for medical use may be cost-effective, ensure privacy of the patient and healthcare professionals, compact for storage in the OR, adapted for non-intrusive installation with existing equipment in the OR, designed to meet infection control standards of hospitals, and so on. Furthermore, the platform may integrate multiple feeds from multiple sources with multiple formats onto a single system, and may ensure that recordings are encoded to a common format that is compatible for subsequent data analysis.

The black-box recording equipment may have included one or more of the following: audio capture and synchronization and digital data capture. Integration of all these data streams may provide complete reconstruction of the clinical encounter. Communication may be a component of non-technical and human factors performance analysis. For example, communication failure may be a contributing factor to adverse events in the OR. Furthermore, team interactions in the OR may rely on verbal communication, which may not be properly evaluated without adequate audio quality. For example, for standalone video files, components of non-technical performance, including teamwork, leadership and decision-making, may not have been evaluated without an audio component. Audio may have been difficult to capture in the OR due to the multiple sources of noise within the room. Primary noise sources in the OR may include the following: preparing for operation (prior to incision), moving trolleys and equipment, doors opening and slamming, moving and dropping metal tools, suction, anesthesia monitors, alarms from anesthetic and surgical equipment, and/or conversation among staff and/or on the intercom. Microphone systems may be designed to capture all audio in the OR, for example: omnidirectional microphones to capture ambient sound, super-cardioid microphones to capture immediate surroundings of anesthetists, cardioid microphones to pick up conversations of clinicians in the surrounding area, and wireless microphones worn by anesthetists to capture their voices. While such a microphone set-up may be able to capture multiple noise sources, its intrusive nature in the OR may introduce a Hawthorne effect. Furthermore, mixing multiple audio feeds can result in poor audio quality, and analyzing each feed separately may be time-consuming.

According to some example embodiments, the platform may include an audio system with minimal microphones which produces optimal audio quality. For analysis of non-technical skills and human factors performance, team communication may be an audio source of interest. Since communication may occur at the surgical field, around the operating table, two cardioid microphones may be mounted on the infield monitors and directed towards the surgical team. An additional microphone may be set-up at the nursing station and directed towards the scrub nurse and equipment cart. A testing and validation phase may help microphone set-up. The testing may recreate noises of a surgical procedure in a real-life OR in order to identify a set-up that may result in a desirable and/or optimal audio quality.

According to some example embodiments, the black-box recording device also may provide both audio-video and multi-feed synchronization for proper data analysis. Audio and video feeds may be synchronized, as even a delay of one-thirtieth of a second, for example, between the two signals may create a detectable echo. Delay lags may increase exponentially over time. Example embodiments of the black-box recording device may have latency of less than one-thirtieth of a second, resulting in synchronization for proper data analysis. Multi-feed synchronization may be provided for multi-perspective analysis of a surgical case. The black-box device may enable the analysis of an event in the OR from multiple perspectives, such as for example, room view, procedural camera view, vital signs and digital data from various sensors. Latency between video/audio/data feeds may decrease the value of multi-channel video recording. In example embodiments of the black-box recording device, the digital data may be formatted, translated and synchronized through middleware hardware and software and using networking protocols for dock synchronization across the network. Digital data may be ingested into the encoder as Metadata. The encoder may be responsible for synchronizing all feeds, encoding them into a signal transport file using lossless audio/video/data compression software For the design of recording equipment, the recording device may have a user-friendly interface which meets privacy concerns. The recording system interface may have a visual display of recorded feeds, among other things, to afford participants an awareness of the content of the recordings, and when recordings were happening. Furthermore, in some example embodiments, the recording equipment may be designed to maximize confidentiality and privacy of both patient and staff participants. Room cameras may be positioned to keep a patient's identity out of the field of view. Microphones may be placed to only capture communication around the surgical field, rather than off-the-record casual communication in the periphery. Some embodiments of the system may have a pause-feature which allows recordings to be easily and seamlessly paused during parts of procedures that are not meant to be recorded (e.g., intubation or extubation phases). Multiple layers of password protection may ensure that the recording system can only be accessed by authorized individuals from the research team.

The black-box may be built on the basis of a modular design—the recording system may be modified, feeds (and associated data capture devices) may be removed or added, without altering the primary/overall functionality of the system. This approach to design may allow for the black-box recording device or encoder to incorporate other data feeds and/or adapt to different clinical settings (e.g., ER department, ICU, endoscopy suites, obstetrical suites, trauma rooms, surgical/medical wards, etc.). The system may be modular, and may be expanded to accommodate for modifications and larger applications. The system may be able to incorporate additional video, audio and/or time-series data feeds (e.g., heart rate monitor, force-torque sensor) in other examples depending on the nature of the medical procedure and the available data capture devices.

"Black-Box" Data Recording Device in the Operating Room

The OR is a high-risk work environment in which complications can occur. Root-cause analyses may reveal that most complications result from multiple events rather than a single cause. However, previous efforts to identify these root-causes may have been limited to retrospective analyses and/or self-reporting. Example embodiments of the platform may implement a multi-channel data recording system for analysis of audio-visual and patient-related data in real-life ORs.

The "black-box" data recording device or encoder which, according to one or more embodiments, may capture multiple synchronized feeds in the OR/patient intervention areas: e.g., room and procedural view, audio, patient physiology data from the anesthesia device, and digital data from various sensors or other data capture devices. These feeds may be displayed on a single interface (e.g., control interface 14) providing a comprehensive overview of the operation. Data may be analyzed for technical skills, error/event rates, and non-technical skills. Post-procedure human factors questionnaires may, according to some embodiments, be completed by the operating team.

Figure 13:
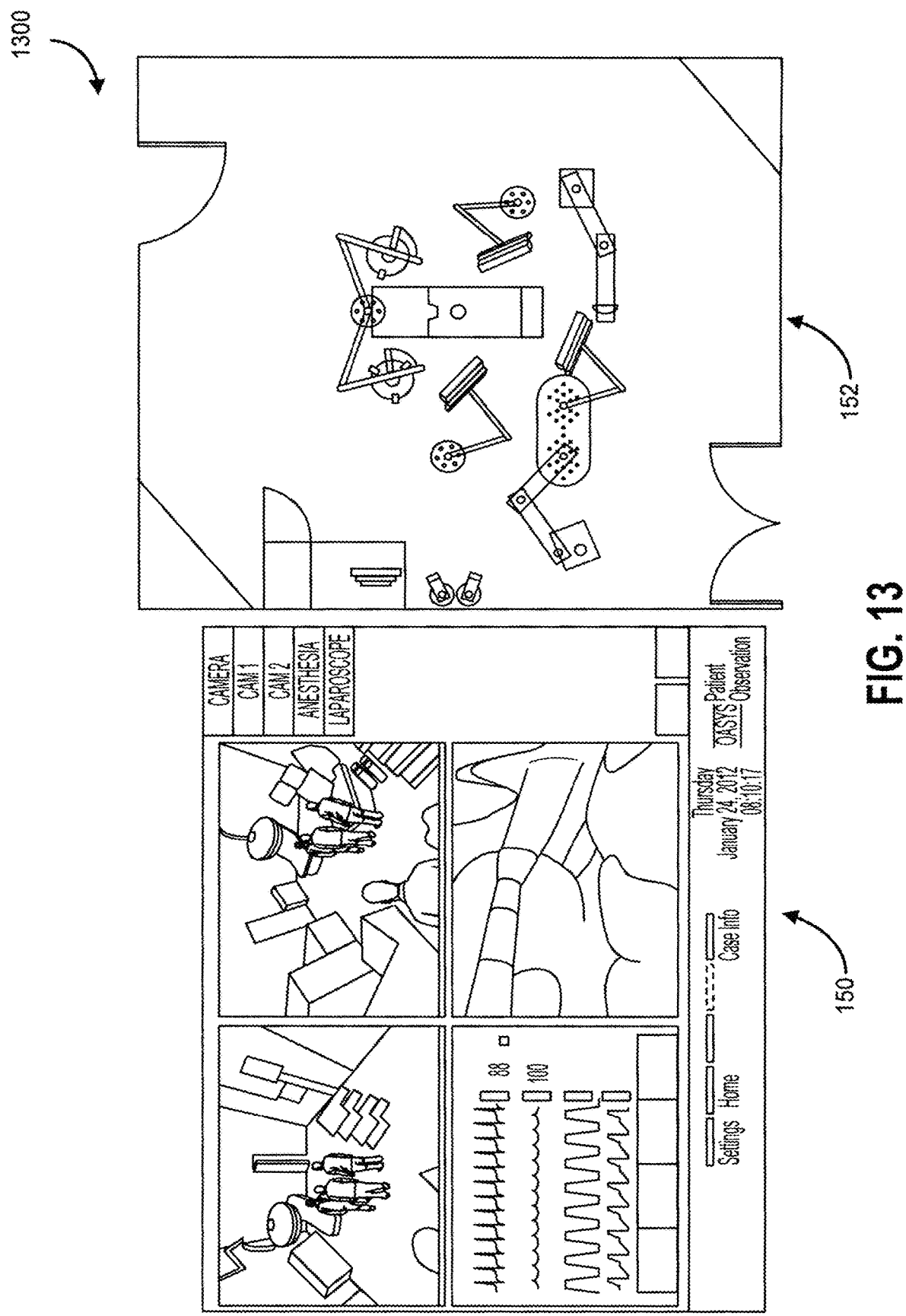
FIG. 13 illustrates a schematic of an example interface according to some embodiments.
Figure 14:
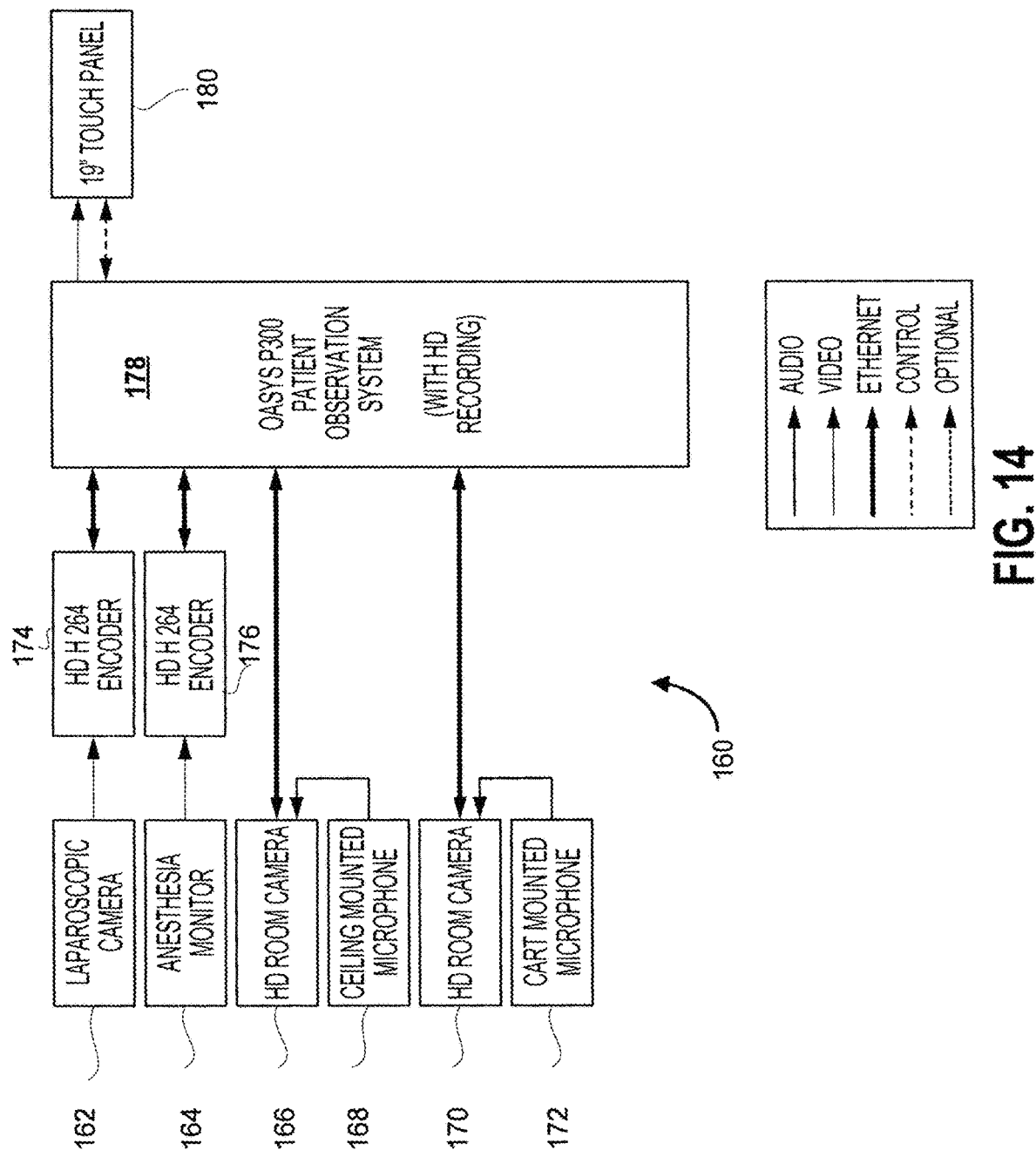
FIG. 14 illustrates a schematic of an example system according to some embodiments.
Figure 15:
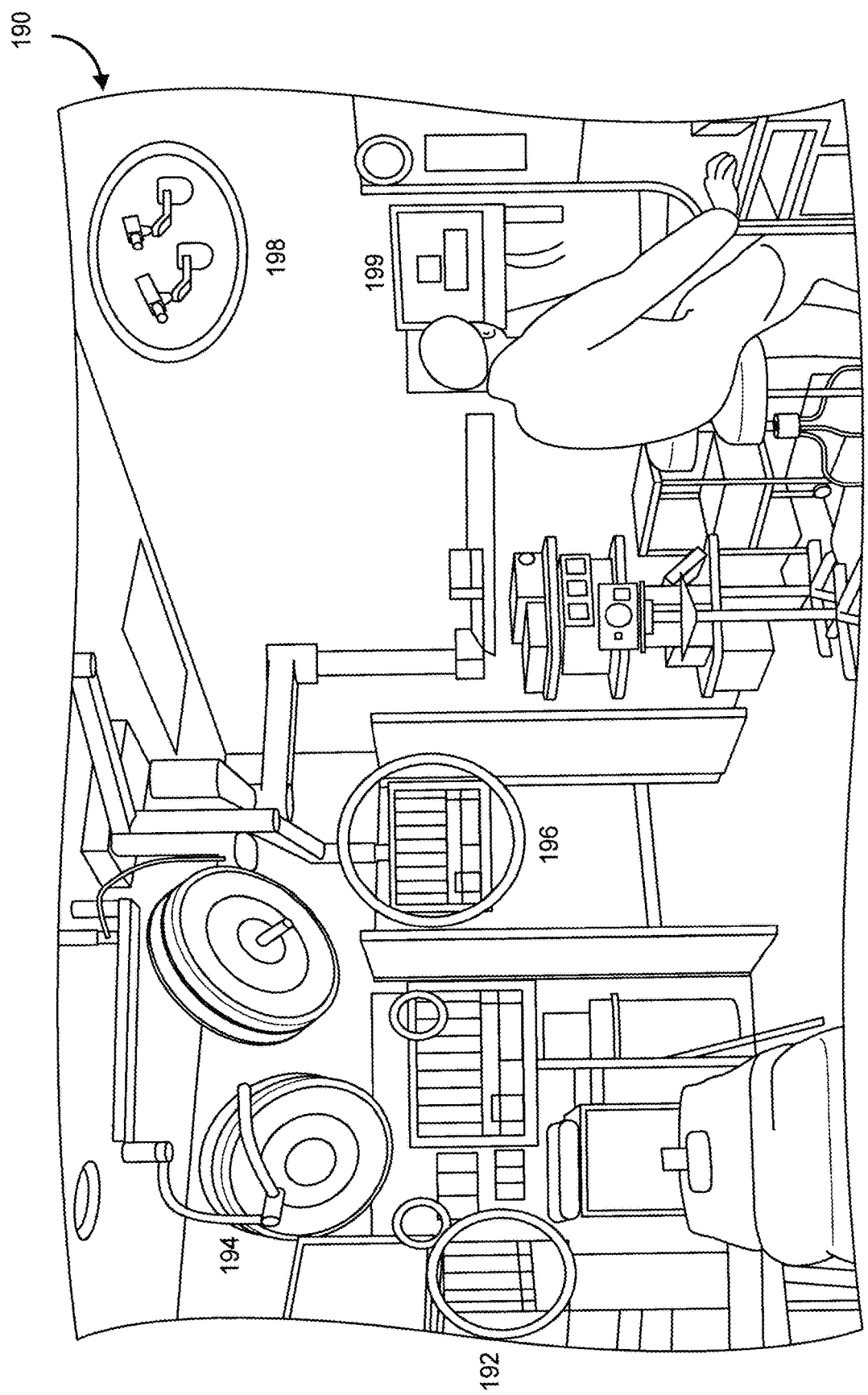
FIG. 15 illustrates a schematic of an example view according to some embodiments.

FIGS. 13 to 15 illustrate schematics of various example views according to some embodiments. For example, FIG. 13 illustrates a schematic interface 1300 with a graphical indicator 150 of display data feeds and a graphical indicator 152 of an OR layout with example positioning of various data capture devices.

FIG. 14 illustrates a schematic of data flow 160 between different system components. Difference data capture devices are shown including cameras 162, 166, 170, patient monitors 164, microphones 168, 172, and so on. The data capture devices may provide output data feeds to encoders 174, 176, other data capture devices or a patient observation system 178. The medical or surgical data may be provided to display device 180 for display or to receive interaction commands via touch screen interface to control one or more components of the system (e.g., view change on camera, start or stop recording). This is an example configuration and other flows and connections may be used by different embodiments.

FIG. 15 illustrates an example OR view 190 with different data capture devices such as a patient monitor 192, microphones 194, laparoscopic camera 196, room mounted cameras 198 and touchscreen display device 199 to provide visual representation of the collected real-time medical data feeds as output data and receive control commands to start or stop capture process, for example, as input data.

The black-box recording device or encoder may provide for analysis of technical and non-technical individual and team performance, errors, event patterns, risks and performance of medical/surgical devices in the OR/patient intervention areas. The black-box recording device or encoder may open opportunities for further studies to identify root-causes of adverse outcomes, and to develop specific training curricula to improve clinical organizational processes, and surgical/device performance, efficiency and safety.

Cloud Platform

Embodiments of the black-box recording device may address technical considerations improving synchronization, reducing latency exposure, providing extended and multi-zone modality and reducing over platform cost. A cloud platform may include the development of intelligent devices and generated time-stamps for the collected data for synchronization of devices and data.

Figure 16:
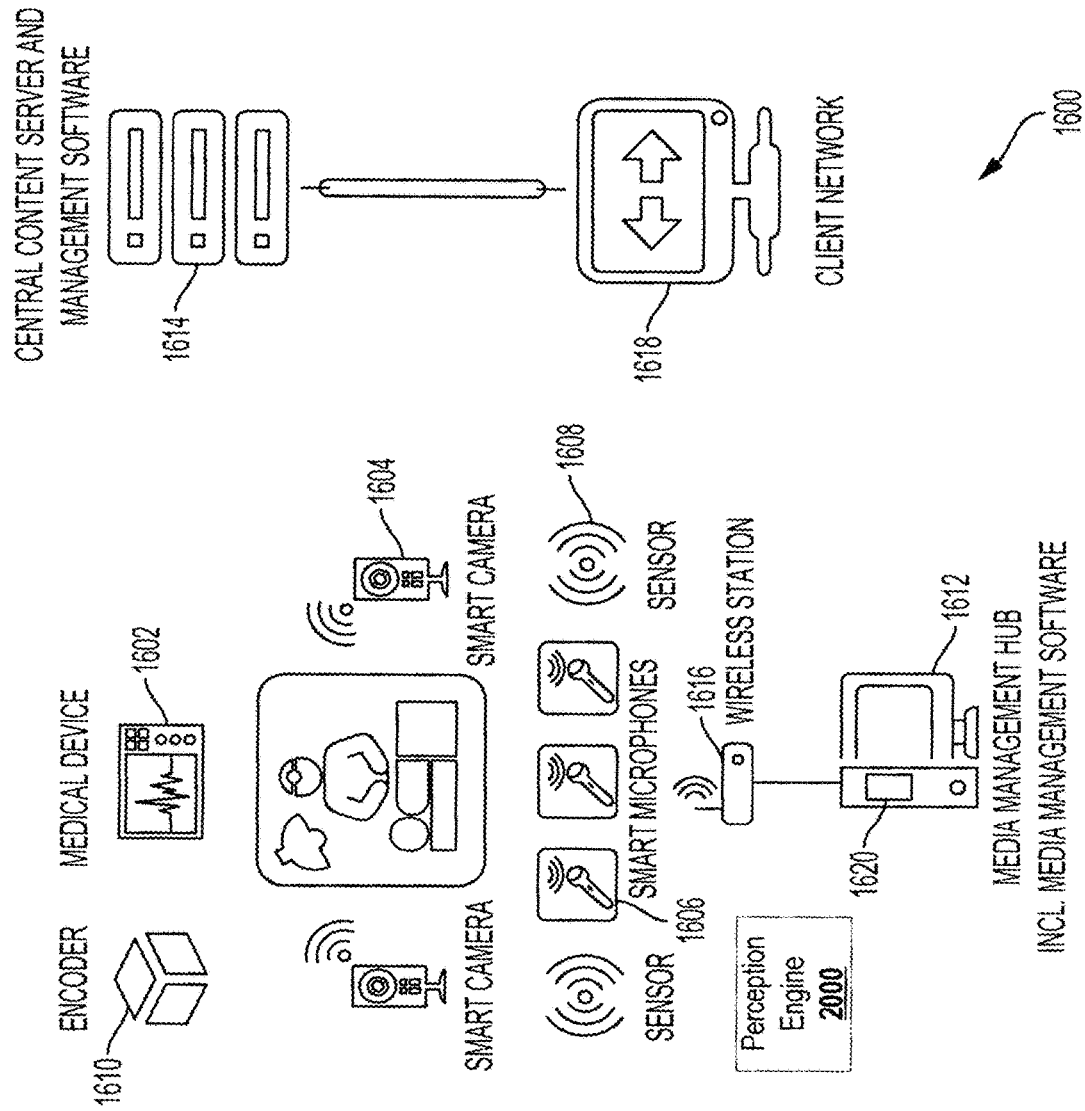
FIG. 16 illustrates a schematic of a black-box recording device according to some embodiments.

FIG. 16 shows an example schematic diagram of a black-box recording device 1600 that may provide a cloud based platform according to some embodiments. Example platform components to provide this capability include autonomous and semi-autonomous smart-enabled devices and adaptors such as medical devices 1602, cameras 1604, microphones 1606, sensors 1608 and so on. In some embodiments, the black-box recording device 1600 may be provided by an encoder 1610 that connects via a wireless station 1616 to a media management hub (MMH) 1612 storing Client Media Management Software instruction code (CMMS) 1620. This connects to a Central Content Server and management software (CCS) 1614 via client network infrastructure 1618 configured for adoption and utilization of high performance wireless communication standards. The black-box recording device 1600 may include perception engine 2000, or a connection (e.g., an established network link) to perception engine 2000 (e.g., where the perception engine 2000 is provided in the form of remote resources).

The smart enabled devices and adaptors may autonomous or semi-autonomous intelligent devices including but not limited to smart cameras 1604, microphones 1606, data and media converters 1612, encoders 1610, adaptors and sensors 1608. In this illustrative embodiment, the smart enabled device or adaptor may incorporate and utilize a SOC device (system-on-chip) or FPGA device (Field Programmable Gate Array) in conjunction with on-board storage, power management and wireless radio(s). It may manage device requirements, device-to-device authentication, storage, communications, content processing, clock synchronization, and time stamping. Depending on factors, the technology may be integrated directly into the device or as an attached adaptor. In some example embodiments, the smart enabled devices and adaptors may connect directly to the CCS 1614 to provide data from the operating site via secure client network infrastructure 1618 and may receive data, commands, and configuration controls from CCS 1624 directly or via MMH 1612.

The black box encoder 1610 may be a composed of one ore more computing devices, tablets and/or laptops which may run a secure user interface for the surgical staff to operate the black box platform. It may be resident on the client network connected via Ethernet or wireless (e.g., via station 1616) and may comply with the network security and IT policies. In some example embodiments, the black box encoder 1610 may connect directly to the CCS 1614 to provide data from the operating site via secure client network infrastructure 1618 and may receive data, commands, and configuration controls from CCS 1624 directly or via MMH 1612.

The Media Management Hub (MMH) 1612 may be a computing machine or server responsible for running the client media management software and its associated services. As an illustrative example it may run on Unix, Linux or Windows Server. The Media Management hub may be resident on the clients network and in addition to the necessary compute, IO and storage requirements, must be compliant to the client network security and IT policies.

Client Media Management Software (CMMS) 1620 may be an application running on the Media Management Hub 1612 that acts as an intermediate conduit between the back office central server and the smart enabled capture devices and adaptors. It may be responsible for the management and control of the black box platform resident on the client network. The CMMS 1620 may aggregate, package, compress and encrypt captured audio, video, medical device data, sensor data, logs, and so on. The CMMS 1620 may organize output files and categorizing by event using standardized file-naming conventions, keywords, file folders, and so on. The CMMS 1620 may provide device management including passing commands from the console, device authentication, security, file transfer hand-shakes, and so on. The CMMS 1620 has a device status dashboard with log file management and error reporting. The CMMS 1620 provides workflow automation, file management and transfer between the client site and the central server. The CMMS 1620 provides additional computing solutions with adherence to the client network security and policies. The CMMS 1620 provides processing and data transformation for clock broadcast for device synchronization.

Central Content Server and management software (CCS) Server 1614 may be located at a main site and act as two-way interface communicating with satellite or client site hubs. The CCS Server 1614 supports remote management, automation and file transfer hand-shakes for the delivery of packaged, compressed and encrypted content from client sites. The CCS Server 1614 acts as conduit to black box analytics software and databases as described herein.

High Performance Wireless Communications (HPWC) may be provided by one or more wireless stations 1616. For example, HPWC may be implemented using multi-gigabit speed wireless communications technology leveraging 802.11ad WiGig, HD wireless, or prevailing standards in support of high-bandwidth digital content transmission.

A workflow is provided as an illustrative example of functionality. Upon receiving a command from a platform console located in the operating or surgical suite, the smart enabled device(s) will commence capture of the appropriate content (audio, video, digital data) to provide digital representations of the operating or surgical suite and people and objects therein. Smart devices or smart adaptors will process (e.g., record, store, generate, manipulate, transform, convert, and reproduce) the captured media and data, and embed a timestamp marker at precise timeline intervals in the output file.

The output files are transferred from the smart enabled device(s) to the MMH 1612 via Ethernet or High Performance Wireless Communication routers and/or devices, shown as wireless station 1616. Wireless routers may be multi-band wireless stations using 802.11ad or the prevailing multi-gigabit speed standards.

The CMMS 1620 may aggregate all media and data (audio, video, device data, sensor data, logs, and so on) and package, compress and encrypt to generate output files. Output files will be organized on network accessible storage devices using standardized file-naming conventions, keywords, file folders, and so on.

At scheduled intervals, files may be transferred over VPN tunnel (e.g., secure network infrastructure shown as client network 1618) from the client site to the processing facility or back office. The CCS 1614 at the receiving facility will manage file transfer and the distribution of content files, media and data to the black box analytics database.

The system 1600 implements synchronization techniques. For example, hardware-based encoding and synchronization may be implemented in part using software methodology. Data synchronization is conducted on the smart enabled device through the embedding of time stamps from the device clock. Device clocks are synchronized across the network via broadcast from the MMH 1612 over high speed wireless network (shown as client network 1618, wireless stations 1616, and so on). As synchronization is done at source by software, media and data may have near-zero levels of latency and the highest level of accuracy The system 1600 implements device management techniques. Devices and coverage zones may be managed under administrative privilege on central console or remotely via the CCS 1614. Controls may be in place to prevent device scheduling conflict. The user may be presented optional capture configurations based on location, zone requirements or procedural type.

The system 1600 implements zone management techniques. As current hardware-based encoding and synchronization solutions are limited by the number of IO ports available on the encoding device. Software synchronization and smart enabled devices may allow for greater scale and ease of deployment. Extended zone and multi-zone captures can be attained thereby allowing for richer content and longer visibility to chain-of-events in support of the data analysis.

The system 1600 implements device status techniques. For example, smart enabled device or adaptor operating status will be broadcast from authenticated devices back to the CMMS 1620. Administrators at client site and/or remotely through the CCS 1614 may be able to access a device dashboard interface that automatically generates visual representations of data reporting key operating metrics and statuses on all authenticated smart enabled devices (e.g., on-line, off-line, running capture, on-board storage, and so on). Where a smart enabled device or adaptor is operating outside of normal conditions (e.g., storage full, off-line) then an alert (email, SMS) will be transmitted to the administrator and appropriately logged.

The system 1600 implements file management techniques. Upon completion of capture and processing on the smart enabled device or adaptor, processed files will be transferred to the MMH 1612. The CMMS 1614 will communicate with the device and transfer will be confirmed via hand-shake. Each device or adaptor may have on-board storage which will serve as short-term file redundancy and recovery across the platform.

The system 1600 may provide reduced cost, lower latency, and higher flexibility. Multi-core encoders and copper cabling in restricted workspace may translate to high costs and commissioning complexity. Cable routing has to be pulled through conduit in sterile core. Cable lengths impact latency of signal. Hardwired connections may restrict device placement and impact capture quality. Example embodiments described herein may be based on a software solution (at least in part to configure various hardware components), over wireless, and using smart enabled devices may reduce overall hardware cost, yield higher accuracy and capture quality, greater flexibility, and ease of commissioning.

Motion Tracking

Embodiments described herein may implement motion tracking using 3D cameras or IR devices. For example, the black box platform may collect and ingest motion tracking data for people and objects at the surgical site. To maintain complete freedom in a clinical environment, markerless motion tracking may be required. Data may be collected from 3D cameras or time-of-flight cameras/sensors.

The platform may implement motion tracking techniques using various components and data transformations. For example, the platform may include one or more autonomous or semi-autonomous 3D depth cameras or Time-of-Flight (TOF) sensors using laser and/or infra-red (IR) devices. As another example, the platform may generate distance and/or position information from the output signal of the TOF sensor and that it converts into a 3D depth map or point cloud. Embodiments described herein may include a computing device for processing output data from 3D camera or TOF sensor. Embodiments described herein may provide customized data processes to distinguish motion resulting from changes in captured depth maps. Embodiments described herein may provide media management hardware and software to aggregate, package, compress, encrypt and synchronize captured point clouds as motion data with other collected media. Embodiments described herein may provide a Central Console for device and capture management and processing software to convert motion data into analyzable information to be used in study of human factors, workflow design and analysis of chain-of-events.

A workflow is described to provide an illustrative example of functionality provided by the platform. In some examples, 3D depth cameras or TOF sensors are fix-mounted in the operating or surgical suite. On receiving a command from the platform, the cameras capture and generate distance and position information of the viewable capture area. Output data will be passed to a computing device running a custom process that creates and establishes a baseline measurement (static field map) and provides summarized motion data by comparing and measuring changes in position information between adjacent 3D depth maps and point clouds. The collective baseline and frame measurement data may be passed to the Media Management Software (e.g., software 1620 on MMH 1612) which may aggregate, package, compress, encrypt and synchronize motion data with the other collected media.

At scheduled intervals, files will be transferred over VPN tunnel from the client site to the processing facility or back office where the motion data will be processed into analyzable information to be used in study of human factors, workflow design and analysis of chain-of-events.

An example process may involve different operations, including for example, a compute operation to receive 3D depth maps or point clouds formatted and structured to be able to conduct point-to-point measurements of change. The compute operation may then create and establish a baseline measurement (static field map), and analyze and record changes in adjacent depth maps or point clouds. The compute operation may map changes to a common timeline and summarize change data on a time continuum basis for purposes of comparison to the reference static field map.

Embodiments described herein may provide synchronization of devices and collected data. For example, the platform may implement synchronization of various media streams to a common timeline as a factor in the determination of the quality of analytics. The following is an example of requirements to maintain accuracy in synchronization: direct connection between all source devices into a general purpose computer; sufficient IO and compute power to compress, encrypt, encode and organize multiple streams of audio, video and data files; an assessment, determination and understanding of latency for all incoming feeds; utilities or algorithms to tune and calibrate infeed's of data to insure synchronization (example introduce offsets); and calibration of time stamps in file headers to a common standard for playback.

Embodiments described herein may provide analytics tools. In future embodiments, process operations may translate point cloud and/or depth mapping position, distance and change measurements into real-world distance measurements. These measurements may permit the creation of the key performance indicators (KPI's), in a semi-autonomous fashion. KPI's can be used to further analysis and/or provide recommendations on workflow and human factors impacting timeline and chain of events. These may include: steps taken, distance travelled, pathway taken vs optimal pathway, impacts of unintended collisions or clustering, impacts of spatial design, impact of arrangements and orientation of staffing, equipment, devices, and so on.

Analytics Applied to the Black Box Data Set

Embodiments described herein may implement data-driven surgical error analysis tools to investigate mechanisms of errors, and to assess error and event patterns. Embodiments described herein may implement process operations for formative feedback, self-assessment, learning and quality control, and to identify patterns, correlations, dependencies and signatures from data collected.

Embodiments described herein may provide an application of data-driven modeling to identify, and extract features, correlations and signatures from data collected and analyzed from the OR black box encoder. Data-driven modeling offers a sound perspective to describe and analyze all those systems for which closed-form analytical expressions may be difficult to determine. Using datasets of input-output pairs of samples related to the problem, the objective is to use Computational Intelligence (CI) to reconstruct a mathematical model that recognizes key factors and predicts clinical outcomes, costs and safety hazards. CI tools may include neural networks, support vector machines, fuzzy inference systems, and several techniques from time-series analysis and dynamical complex systems. Using CI-based approaches, both offline and online solutions could be built for analyzing errors, adverse events and adverse outcomes in surgery. The term offline refers to solutions that may be used to automatically infer knowledge (e.g., rules of causations, correlations) from examples describing past events recorded in the OR. The online approach may provide a real-time tool to assist surgeons and OR teams intra-operatively. Such an instrument may operate by monitoring the current conditions in the OR, reporting events that may lead to conditions of potential errors (e.g., the noise level, temperature, number of individuals in the room, and so on).

The following provides an overview of computational intelligence methodologies applied in the OR black box encoder solution. Computational intelligence methodologies may be used to design networks capable of extracting features, correlation and the behavior of events that involve complex, multi-variable processes with time-variant parameters. For the present application, methods may include artificial neural networks (ANN), both feed forward and recurrent, radial basis function networks (RBFN), fuzzy logic systems (FLS), and support vector machines (SVM). Applied to the data generated by the OR black box, these systems will be capable of implementing various functionality, including for example, finding complex, nonlinear and hidden relationships among the data representing human performance, patient physiology, sensors, clinical outcomes and clinical costs, and predicting outcomes and behaviors. Further example functionality includes a functional generalization and, as such, acceptably responding to situations to which the OR black box encoder solution has not been exposed before, and offering alternative solutions when the system cannot be expressed in terms of equations, or when a mathematical model does not exist or is ill-defined.

Example advantages of FLSs are the capability to express nonlinear input/output relationships by a set of qualitative if-then rules, and to handle both numerical data and linguistic knowledge, especially the latter, which may be difficult to quantify by means of traditional mathematics. The main advantage of ANNs, RBFNs and SVM, on the other hand, is the inherent learning capability, which enables the networks to adaptively improve their performance. The present solution may apply CI methodologies, including ANN, RBFN and SVM, to develop robust networks and models that will extract features, detect correlations, and identify patterns of events from the OR black box dataset.

As noted, embodiments described herein may implement data analytic techniques using artificial neural networks. For example, time-series modeling may include applications of time delayed ANNs and feedforward multi-layer perceptron networks to model nonlinear dynamical systems. As another example, hybrid stochastic and feedforward neural networks may be used to predict nonlinear and non-stationary time series by incorporating a priori knowledge from stochastic modeling into neural network-based predictor. As a further example, two-layer neural networks consisting of a series of nonlinear predictor units together with a Bayesian based decision unit for time series classification. As another example, ANNs for time-series prediction and the impact of the use of the heuristics to select the optimum size of the sampling window. Other neural network topology may be used, such as a recurrent architecture whereby temporal relations can be built into the network via feedback connections. Recurrent neural networks have been extensively investigated for periodic and chaotic time-series prediction. A few additional examples include applications of robust learning operations for recurrent neural networks based on filtering outliers from input/output space suitable for time series prediction; various selection methodologies for optimal parameter adjustment in pipelined recurrent neural networks used for prediction of nonlinear signals; complex-valued pipelined recurrent neural networks for modeling/prediction of nonlinear and non-stationary signals; recurrent predictor neural networks in combination with self-adaptive back-propagation through time learning algorithm for prediction of chaotic time series; and self-organizing map and recurrent neural networks to model non-stationary, nonlinear and noisy time series.

Some example embodiments may use radial basis function networks where feedforward and recurrent RBFNs may be examined for time-series modeling of the black box data sets.

Some example embodiments may use neuro-fuzzy networks. Different adaptive neuro-fuzzy inference system (ANFIS), alternate neuro-fuzzy architecture (ANFA), dynamic evolving neural-fuzzy inference system (DENFIS) to chaotic time series prediction may be utilized. Examples of such application include: (1) real-time neuro-fuzzy based predictors for dynamical system forecasting; and (2) hybrid recurrent neuro fuzzy networks using non-orthogonal based wavelet, recurrent compensatory neuro-fuzzy systems, and weighted recurrent neuro-fuzzy networks for modeling of nonlinear dynamic systems.

Further example embodiments may use support vector machines. The SVMs may be used for time-series forecasting of clinically-relevant performance outcomes, adverse events, complications and costs/return on investment.

Some example embodiments may use nonlinear Black Box data modeling techniques. In cases of an absence of a priori information, embodiments described herein may use a model that describes the dynamic behavior (features/signatures) of the system on the basis of a finite set of measured input-output pairs. Various nonlinear black-box modeling problems can be realized as that of selecting the best mapping mechanism using the input-output data and then trying to minimize the error between the output of the model and the measured output.

In some embodiments, smart data analytics techniques may be applied to transform unstructured data into structured and meaningful information. The framework to analyze the black box data may be focused on data-driven analytics and data modeling. The OR black box may be provided to develop medical domain expertise that may be used to customize the data analytics tools to the specific healthcare needs.

A framework is established to assess performance and medical errors and adverse events that are observed in the black box data (e.g., data obtained by encoder 22). This assessment framework has been developed by leading global healthcare practitioners and follows leading practices in the field.

The technical performance of the surgeon is assessed by using an error-rating tool and a global rating scale. In addition, the intraoperative team performance of the surgical, anesthesia and nursing team are assessed using standardized (e.g., normalized) rating tools.

A step includes the provisioning of a robust protocol for data extraction into a relational database management system (RDBMS) with a well-defined entity-relationship diagram. The black box data (e.g., data provided to encoder 22 in the form of various data stream feeds) may include video data (in-room videos and the procedural video), audio data (directional microphones and decibel level in room), physiological patient data, signal output data from surgical instruments, room temperature data, and foot traffic data from motion sensing input devices, etc., among others. These feeds may be provided at different times and may require synchronization by endoder 22 prior to extraction. In some embodiments, the feeds already have features extracted and provided in the form of machine-readable and/or interpretable formats, in other embodiments, the feeds may first require processing or pre-processing to extract feature sets.

The volume, velocity and variety may be similar to "big data" and "big data" techniques may be applicable. The metadata may be stored in various formats, such as in records stored in MySQL. In some embodiments, more advanced storage systems such as the Hadoop Distributed File System (HDFS) may be used to store the video data.

To extract the data in a meaningful and structured way, time stamping may be used to provide temporal order among a set of events. Time-stamped events may be displayed on a timeline, and summarized in a matrix that indicates the duration and frequency of each event. The timeline provides a visual representation of time-stamped events to facilitate data analysis and the development of predictive algorithms.

Another step may include the exploratory analysis of the data. There may be various features collected in the data, and exploratory analysis may include utilizing data statistical analysis to identify and extract features. The temporal nature of the data may lead to the data being particularly well suited for time series analysis to extract meaningful statistics and insights. Time chart, distribution, autocorrelation, cross-correlation and spectral analysis may be used to investigate the temporal nature of the data.

The exploratory analysis of the data holds the opportunity for pioneering work in the field of data analytics of Black box data. By combining data analytics with domain expertise, questions such as "What are root causes of negative outcomes?" may be answered.

Root cause analysis (RCA) is a framework that may provide a proven method of problem solving used to identify the root causes of errors. Hierarchical clustering models in data mining may be used for root cause analysis to determine cluster groups and events. The output of the hierarchical clustering models may be a dendrogram. The 5 'whys' may be asked to identify the causes associated with each sequential step towards the outcome. Causes may be classified into two (or more) categories: causal factors and root causes. The root cause category has the defining characteristics that it interrupts the sequence chain when eliminated, and the outcome of the root cause analysis may provide invaluable insights to complement medical insights in understanding the cause of negative and positive outcomes.

Data-driven modeling may be used to describe and analyze systems, even when a closed-form analytical expression is difficult to determine. An objective of data modeling is recognition and prediction of the relevant patterns that cause negative outcomes. This is where cognitive computing and smart analytics may be utilized.

The data modeling toolbox leverages the machine learning capabilities. While the use of hierarchical clustering for root cause analysis (RCA) is previously discussed, there may be other supervised learning techniques that some embodiments may utilize, such as support vector machines (SVM) as well as artificial neural networks (ANN).

Support vector machine (SVM) approaches offer a robust approach to classification originally developed as a linear classifiers and later expanded into a nonlinear classifier using the kernel trick. Artificial neural networks (ANN) may also offer a powerful approach for relevant applications that include time series prediction, clustering, classification and pattern recognition. The approaches may be used individually or in combination, according to various embodiments.

SVM and ANN excel at finding hidden relationships in data-rich content as well as providing predictive behaviour of the system. The ability to model, recognize and predict the relevant patterns has tremendous potential not only for historical data but also for real-time data analytics. In some embodiments, domain expertise, data modeling and machine learning techniques are applied to the black box data (e.g., stored in encoder 22).

This may lead to: identification of frequent temporal patterns leading to errors/adverse events in the timelines, and development of predictive algorithms that can identify critical events during surgical procedures.

The timeline data collected in parallel may, in some embodiments, contain time-stamped temporal events.

The time-stamped series of technical and non-technical events may be recorded and categorized depending on: if the events were caused by nurses or surgeons, or other factors. Data analytics tools on the timeline analyzed by the medical team such as N-gram pattern extraction algorithm may be used, in some embodiments.

In some embodiments, MinEPI pattern extraction algorithm(s) may be used for identification of parallel and hybrid patterns. Patterns of events and their relationships with errors may then be validated and incorrect patterns may be filtered out.

This temporal pattern recognition may be useful in automating the process of determining the events and errors commonly leading to adverse events/adverse outcomes.

To support the data extraction the exploratory analysis and to exploit the advanced modeling and machine learning capabilities of the black box system, a platform may be provided for aggregation and capture of relevant and specific content used in the systematic analysis of operating and medical procedures. The extensive volume of varied data accompanied by its veracity may pose specific challenges to scale and efficient processing.

Therefore, any platform used must be scalable, robust, and provide the necessary capabilities to intelligently filter, annotate and correlate events and behaviors for use in the extraction and the analytics phases. In some embodiments, the black box system leverages a medical centric perception engine 2000, which, as noted in FIGS. 10A and 10B, may reside in various locations and in various repects relative to the encoder 22 (e.g., as part of encoder 22, in the form of distributed computing resources in a server farm, on a remote device).

Figure 17:
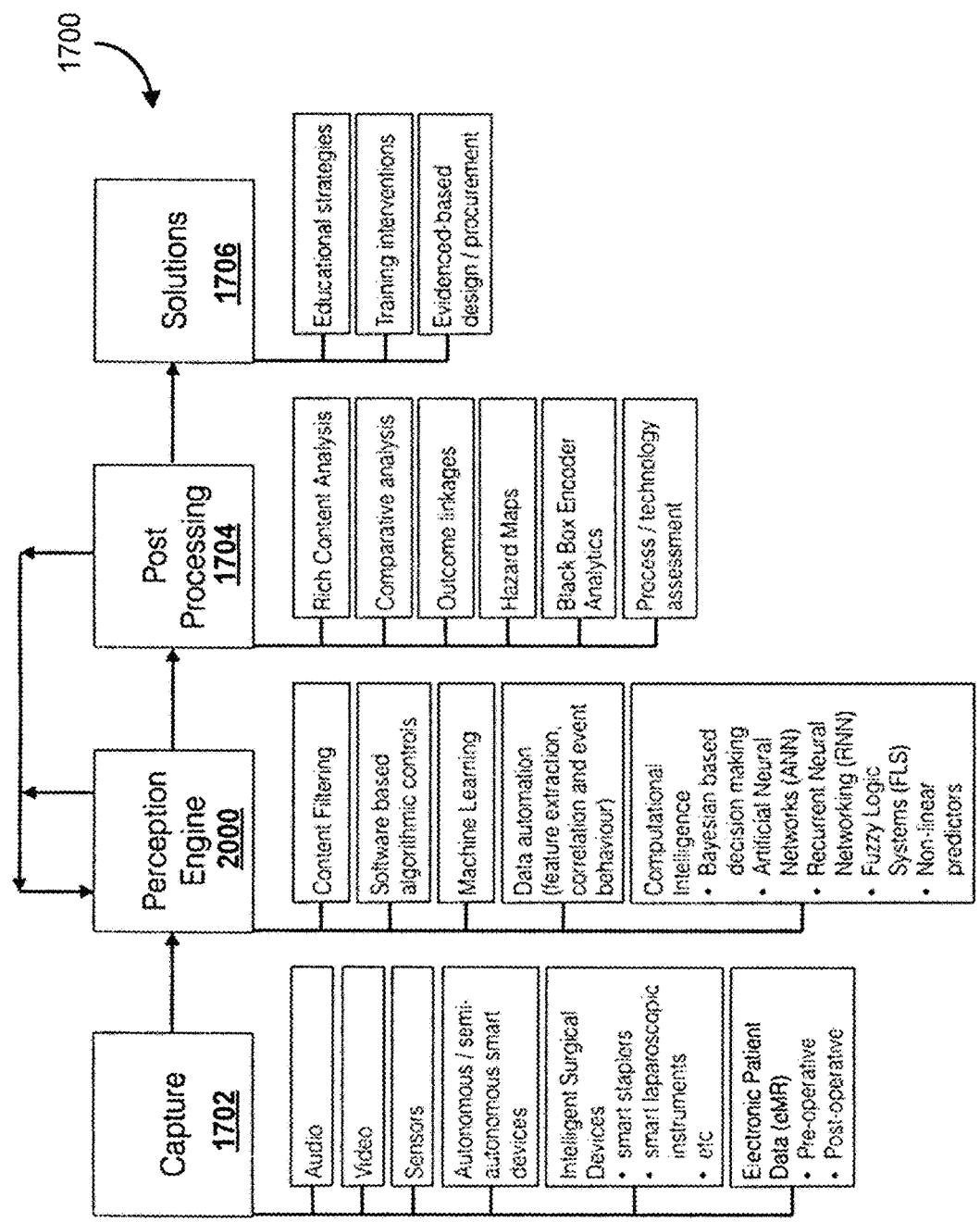
FIG. 17 is a chart illustrative of some features of a black box system, according to some embodiments.

FIG. 17 is a chart illustrative of some features of a black box system, according to some embodiments. As indicated in FIG. 17, the chart presents a sample structured work flow from capture and aggregation (Capture 1702), data management, annotation, filtering and data correlation (Perception Engine 2000), analytics, linkages, predictive modelling and hazard mapping (Post Processing 1704) and finally solutions 1706.

Various types of content and data captured by the black box system across multiple sources, inputs and device types including but not limited to: cameras (optical, 3D depth, laser, stereo), microphones, sensors (examples include but not limited to acoustic, environmental, flow, positional, displacement, electrical, and other sensors), autonomous and semi-autonomous smart devices, intelligent surgical instruments (e.g., smart staplers, intelligent laparoscopic instruments, etc.), surgical equipment (e.g., anesthesia monitors, patient monitors, energy devices, $O_2$ saturation monitors, etc.), pre-operative monitoring systems, post-operative monitoring systems, patient record systems and databases, wearables. etc.

Interconnection of data sources may be provided through direct and indirect services, using wired, bluetooth, near field (NFC), Li-Fi, prevailing wireless protocols, etc. These services may act in a coordinated fashion as part of a device mesh and/or private client network.

Devices may use available on-board communication or for those devices without the necessary communication structure, through smart enabled adaptor modules which act as autonomous agents connecting the device to the network.

Smart enabled adaptors may provide network connectivity, security and processing capability (e.g., record, store, generate, manipulate, transform, convert and reproduce). Captured data may be time-stamped, geo-stamped, or otherwise classified, categorized or profiled at intervals. Security not only may also be designed to manage access and control, to block attacks and measure threats, but also to deliver advanced threat detection, response and counter-response.

A perception engine 2000 may be provided to address challenges faced in scale and data processing efficiency, adopting technologies and strategies from IOT (Internet of Things), IOE (Information of everything), adaptive technologies, advanced machine learning methodologies, and computational intelligence. Advanced algorithmic controls and software based decision-making may be deployed at targeted nodes and may act as a black box perception engine 2000. Nodes may be local, regional, or global and are otherwise characterized as locations where decisions and filters are made.

The perception engine 2000 may be configured to filter content, categorize, profile, extract features, uncover underlying data behaviors and provide evidence of correlation of events in complex multi-variable processes and timelines. In some embodiments, the perception engine 2000 is configured to prioritize and/or weight the various feeds and/or features for analysis, such that perception engine 2000 is tuned and/or biased towards feeds and/or features of particular importance. Such determination for biasing the perception engine 2000 may be based on statistical reviews of the accuracy (e.g., sensitivity, specificity) of the results of perception engine 2000. The perception engine 2000 is configured to generate predictions and/or determinations based on analyses of various extracted features, estimating when clinical events (e.g., technical errors, technical events) have occurred based on information obtained from the data sets. The specific approach taken by the perception engine 2000 is, in some embodiments, configured to modify itself over time (e.g., modifying rules, weightings, splitting criterion) and iterations with data sets such that perception engine 2000 becomes tuned in developing predictions. In some embodiments, a high (or baseline) specificity rate may be targeted as an outcome as the predictions iterate through incoming data sets.

In an embodiment of a two-node implementation, connected devices, sensors, record systems, equipment and machines, may be networked with a computing platform that operates software-based controls and algorithms utilizing some type of neuromorphic processor (e.g., IBM TrueNorth™ or similar neuromorphic device). The devices and computer may operate on a private network.

Incoming inputs from source may be fed to a computing platform where they are monitored. Onboard software in conjunction with a neural processor may be configured to conduct first level filtering, making criteria-based decisions, extract identifiable features, categorize events, make inferences on data sets, conduct classifications of data and data streams.

The software algorithms and actionable decision matrices used by a computing platform may be developed based on clinical science, advanced statistical analysis and evidentiary research, among others. The programming may be conducted in a language compatible with a neuromorphic processor, generating something similar to spikes, and relationships of input/output, cause/effect, decision making etc., may be mapped, weighted and transcribed in the form of a firmware or program. Some embodiments may operate as neurosynaptic core or array of cores like a TrueNorth™ neural processor and use their architecture of axons (inputs), synapses (connections) and neurons (computations/outputs).

Filtering of inputs and feeds from devices may be processed in real time. Classifiers and decision making may be conducted utilizing developed algorithmic libraries and computational intelligence. Accuracy and predictive capabilities may be improved through back propagating and machine learning techniques.

Network based software may manage filtered content including storage, routing, archival, local node and network security, and may be responsible to transmit data and filtered information to the next node over a secure private network. On receipt, filtered content may be added to the post-processing databases adding and increasing to the overall evidentiary knowledge base.

Additional content analytics, comparative analysis, hazard maps etc., may be conducted. Correlated linkages may be identified with this filtered content. Increased correlation, previously unidentified or underlying data behaviors across statistical datasets, and further refinements and predictors may be fed back into the perception engine 2000, thereby increasing the refinement of filtering algorithms moving forward.

Some examples and embodiments describe capabilities and logical flows of the platform, an ability to address scalability and processing efficiency and the exploitation of modelling and machine learning for advanced analysis. The embodiments may range from simple to complex multi-nodal applications.

Figure 18:
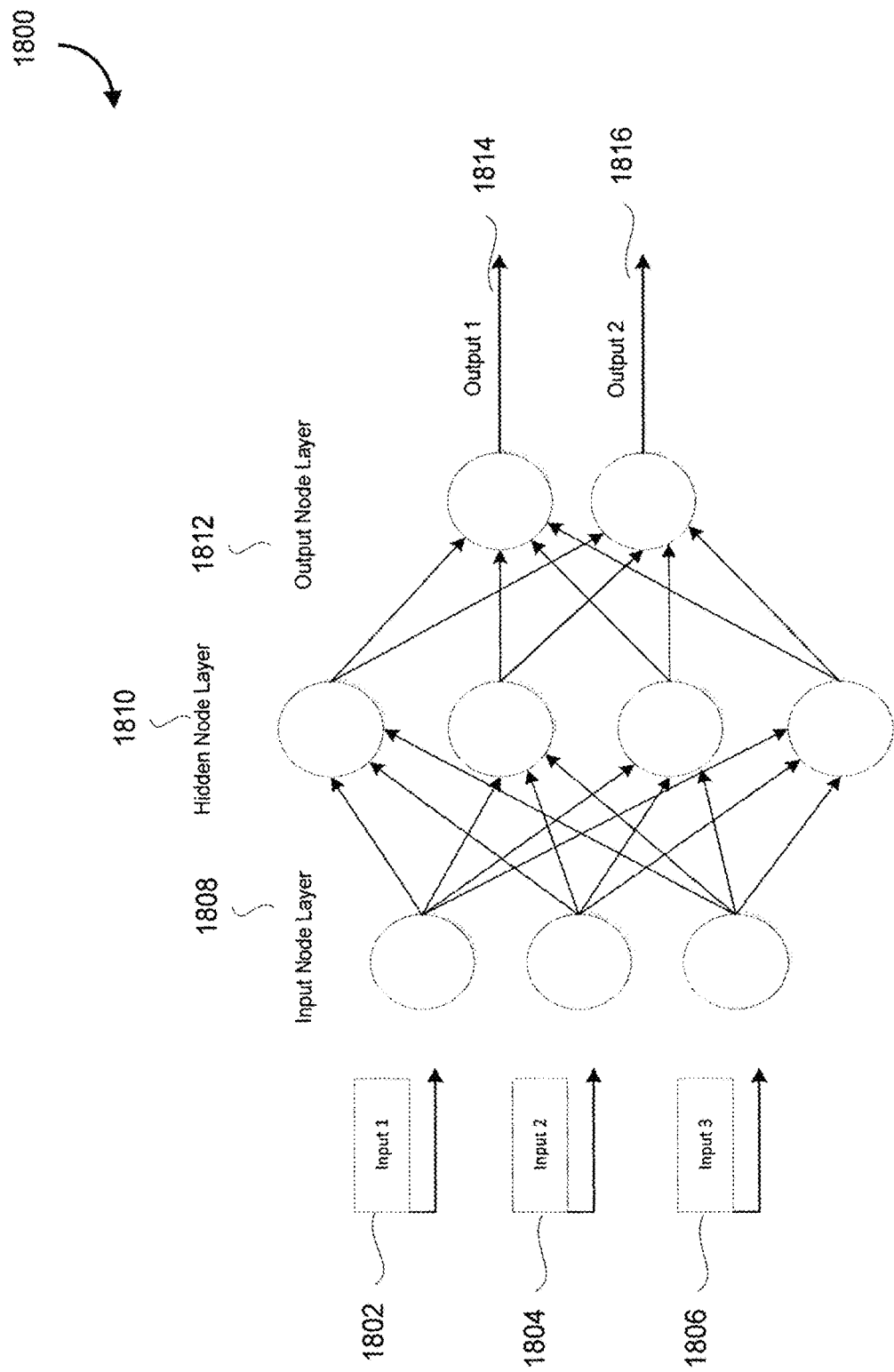
FIG. 18 is a graphical depiction of a simplified artificial neural net (ANN) logic diagram underlying the perception engine 2000, according to some embodiments.

FIG. 18 is a graphical depiction 1800 of a simplified artificial neural net (ANN) logic diagram underlying the perception engine 2000, according to some embodiments. Correlation data, inferences, and feature extraction may be established to discover underlying data behaviours of increasingly complex multi-variable process, timelines and events. FIG. 18 shows inputs 1802, 1804, 1806, input node layer 1808, hidden node layer 1810, output node layer 1812, and outputs 1814, 1816.

Steps in a process for providing machine learning using perception engine 2000 may include training the algorithm through a manual review of feeds, marking points in time where clinical events have occurred, and the manually flagged information may be provided into the perception engine 2000 for training purposes. The perception engine 2000 may then utilize machine-learning approaches to re-preocess the data feeds to generate predictions for additional errors based on the extracted features and patterns, generating outputs indicative of additional errors linked to timestamps stored on a common timeline. Accordingly, in some embodiments, the data set required for training may need to be a sufficiently large data set.

The perception engine 2000 may be tuned such that clinical events are flagged with a particular confidence level and/or confidence score. The confidence level and/or the confidence score may also be associated with a competence level or a competence score. While the perception engine 2000 itself can be modified in terms of which features to focus on and/or to weigh on, the perception engine 2000 results may also be filtered based on confidence level and/or confidence score. In some embodiments, the confidence level and/or confidence score associated with various clinical events is represented graphically on an output, such as an annotated timeline chart. In some embodiments, the confidence level and/or confidence score is stored in metadata and incorporated into instruction sets for notifications of when in a particular surgical procedure the data feeds should be reviewed to assess the presence and/or absence of technical errors and/or events.

In an embodiment, output layers of a one perception engine would be combined with other inputs or outputs from other perception engines to form a multi-node perception engine. Such a configuration could provide even higher order processing and richer content to be used in advanced analytics, statistical processing and problem identification and hazard mapping (e.g., heat maps, confidence levels, potential for clustering of events).

Figure 19:
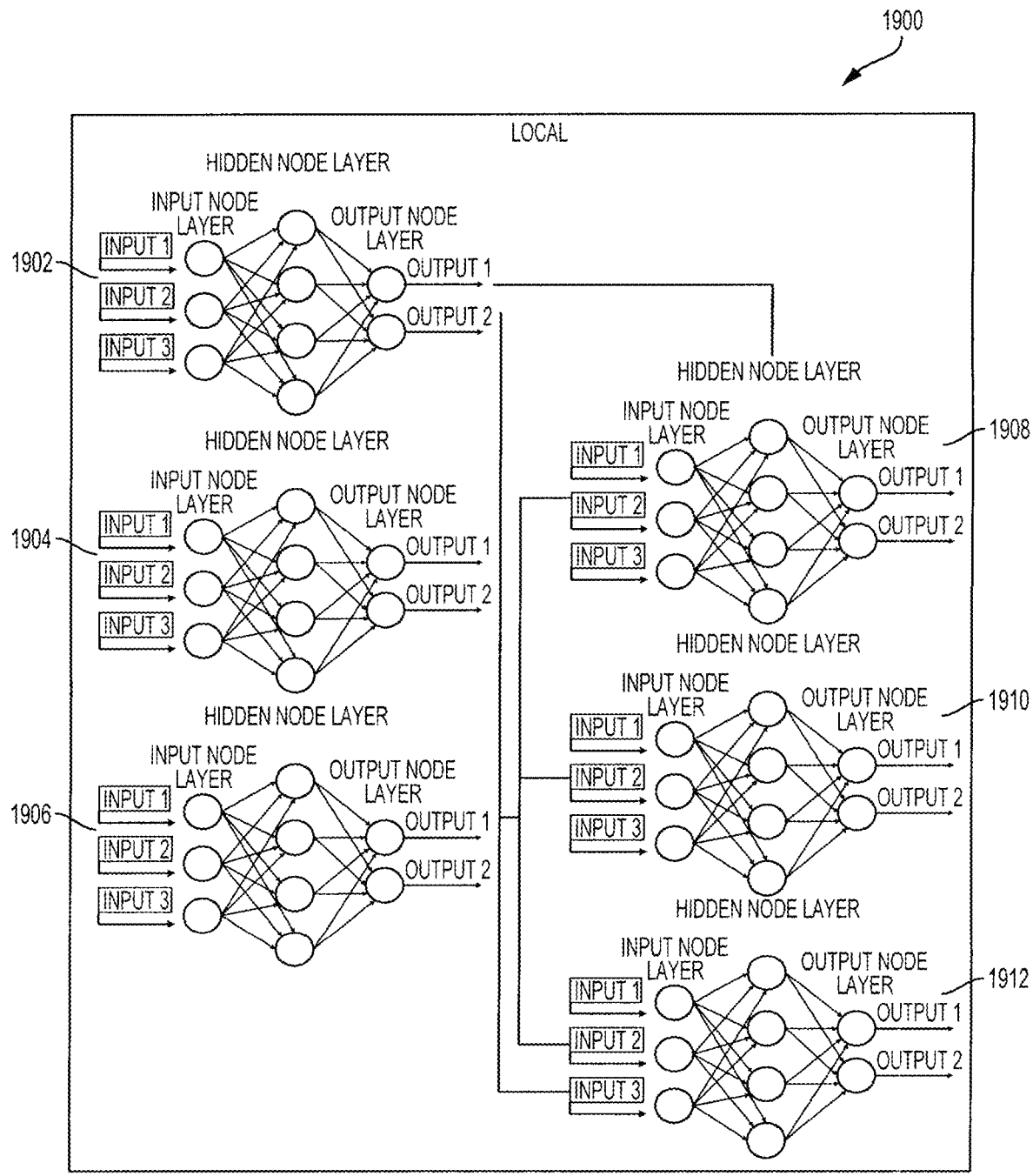
FIG. 19 depicts a multi-nodal perception engine configured on a localized network, according to some embodiments.

FIG. 19 is a schematic view 1900 of a multi-nodal perception engine configured on a localized network, according to some embodiments. As depicted in FIG. 19, there may be one or more machine-learning networks 1902, 1904, 1906, 1908, 1910, 1912 that are used at various locations, and the outputs and rules may be applied at a local, regional, or global level. For example, for ORs in facilities where a sufficiently large data set is not available, the OR may be able to benefit from other tracked rules and/or refined machine-learning approaches used in other facilities. In some embodiments, facilities may cross-validate tracked and predicted errors against data sets stored in other facilities such that a total available data set may be larger.

Another embodiment includes a wide area perception engine with aggregation across spatial or logical dimensions. Across high speed networks mapped use cases may allow for extraction of features and data relationships across spatial or logical dimensions thereby allowing for comparisons between different aggregation points.

Figure 20:
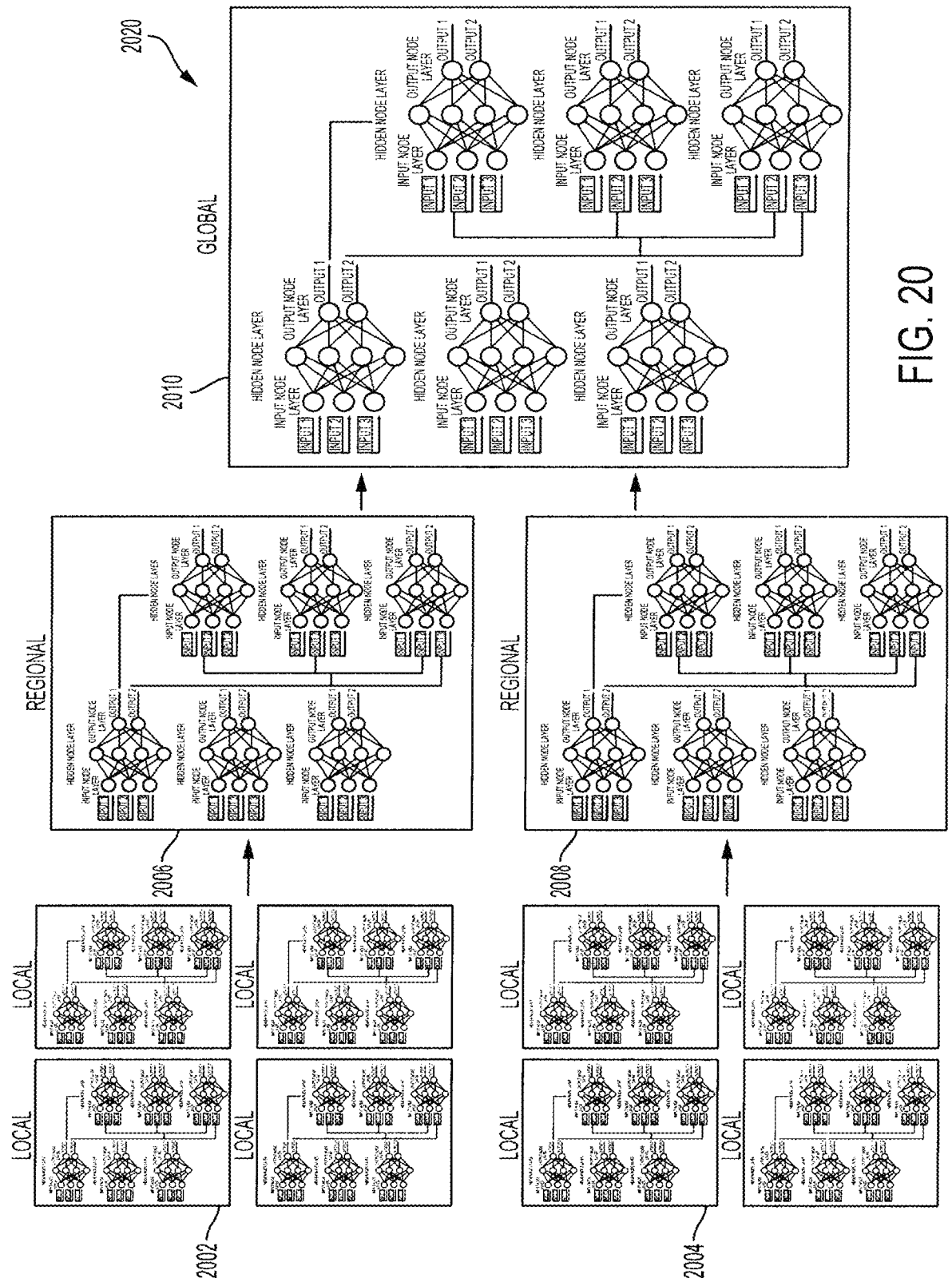
FIG. 20 depicts a multi-center perception engine, according to some embodiments.

Such a system may extend the black box system beyond local assessment and provide insight and evidence across healthcare system levels, between regions and benchmark against global standards for the exploitation of leading practices on a macro level. FIG. 20 is a schematic view 2020 of a multi-center perception engine network, according to some embodiments. As shown, outputs of local perception engines 2002, 2004 may be processed by regional perception engines 2006, 2008 to generate outputs that are further fed into global perception engine 2010.

The OR black box system may be designed to focus on developing targeted interventions based on the obtained data to address performance and organizational deficiencies, and the most frequent hazards to patient safety at an individual, team and institutional level.

Currently, the vast majority of safety regulations and training interventions are based on retrospective root-cause analyses, or have been derived from other high-risk industries that may or may not be relevant in health-care.

Some embodiments of the system may be adapted to target the development of evidence-based interventions using prospective data that has been generated at the point of care, and this concept has never been used in healthcare before.

The data obtained from the systematic analysis of operative procedures may provide insight into the complex processes within the healthcare system, allow assessment of performance on an individual and team level, and evaluate human interactions with modern technology.

Furthermore, the data can be used to determine specific individual and team weaknesses, hazard zones (e.g., through heat maps) within procedures as well as characterize the cascade of events that result in "near misses" or adverse patient outcomes. The information may deliver knowledge content useful to tailor effective educational interventions based on real life observations rather than hypothetical scenarios used in current training. The concept, in relation to experiential learning may be used to create educational strategies that can be disseminated to sites that do not have access to their own real-life data.

The Process May Include the Following Steps:

1. Identification of root-causes of adverse outcomes and design of training scenarios.

In many cases the cause of adverse patient outcomes remain elusive since they are frequently multifactorial and based on retrospective analysis. By analyzing all prospectively documented adverse outcomes using the OR black box system, patterns of recurrent problems will be identified, characterized and used to generate a set of training scenarios based on the real experiences. This knowledge may relevant to healthcare personnel (OR teams) involved in patient treatment in similar clinical contexts.

The educational content can be compiled to information sheets, textbooks, e-learning software and integrated into standard operating procedures (SOP) at an institutional level. Beyond summarizing common or significant root-causes of adverse outcomes, these scenarios may be used to generate software packages for full-scale simulations in virtual operating rooms. The variables may be programmed into the simulation software and thus be packaged, commercialized and exported to educational institutions.

2. Analysis to determine error frequencies, distribution and hazard zones within procedures to devise "error-focused" educational curricula.

Surgical errors are "symptomatic" and can be caused by different factors, only one of these being skill level of the surgeon. Errors may be the result of lack in technical skill (as observable in surgeons in training), lack of judgment and cognitive factors (as observed in procedures by surgeons in training/inexperience), and the complexity of the case or surgical step (observable in expert procedures). Experimental results indicate that errors occur in clusters. In order to eliminate confounders, procedures performed by expert surgeons may be examined where the error clusters would be indicative of "complex" steps and where educational interventions should be developed to improve performance.

Through the analysis of the data generated by the OR black box system, error distribution patterns for numerous procedures and surgeon training levels may be identified. These specific patterns may be used when designing curricula focused on creating "error awareness" and in conveying mitigation concepts.

Mapping procedure complexity and identifying potential hazard zones may be used to create educational strategies targeted directly at these steps. Instructional strategies such as but not limited to deliberate practice may then be used to train for these steps and thus minimize the risk of adverse events. Informing surgeons about complex or hazardous steps also enables the design of standard operating procedures, which is common in aviation (for example the "sterile" cockpit concept during takeoff and landing), to limit distractions during these sensitive steps (no procedure irrelevant conversation, minimize room traffic, reduce overall noise level).

3. Identification of beneficial and detrimental operating team interactions, and design and validation of simulated team training scenarios.

Recognition of specific behavior patterns within teams that are either beneficial or detrimental to patient outcome is a step that may be used to subsequently fashion specific team training interventions and debriefing sessions. The data generated through the OR black-box system 1600 observations may be used to identify specific patterns in non-technical performance of the teams. This information may serve as the basis for the design of specific team interventions using OR simulations, role-play and debriefing sessions. Recurrent themes that are identified as affecting team performance and processes on an organizational level may be addressed by policy recommendations and the design of standard operating procedures.

At an individual level, deficiencies in technical and non-technical performance may be addressed in targeted interventions utilizing evidence based instructional strategies and approaches such as but not limited to: behavior modeling, debriefing, warm-up training, deliberate practice and simulation.

At the level of the OR team, inter-professional teaching sessions and training interventions may be tailored to the most common observed team failure patterns and identified threats to patient safety. Evidence-based methods such as but not limited to crisis-simulations, in-situ simulations, role-play, and group debriefing may be employed.

At the organizational level, measures may include policy changes to address operation room ergonomics, OR processes, and environmental factors such as noise and OR traffic. In addition, the data may be used to design specific checklists and standard operating procedures for the most relevant or hazardous situations.

Machine Learning Example

Figure 21:
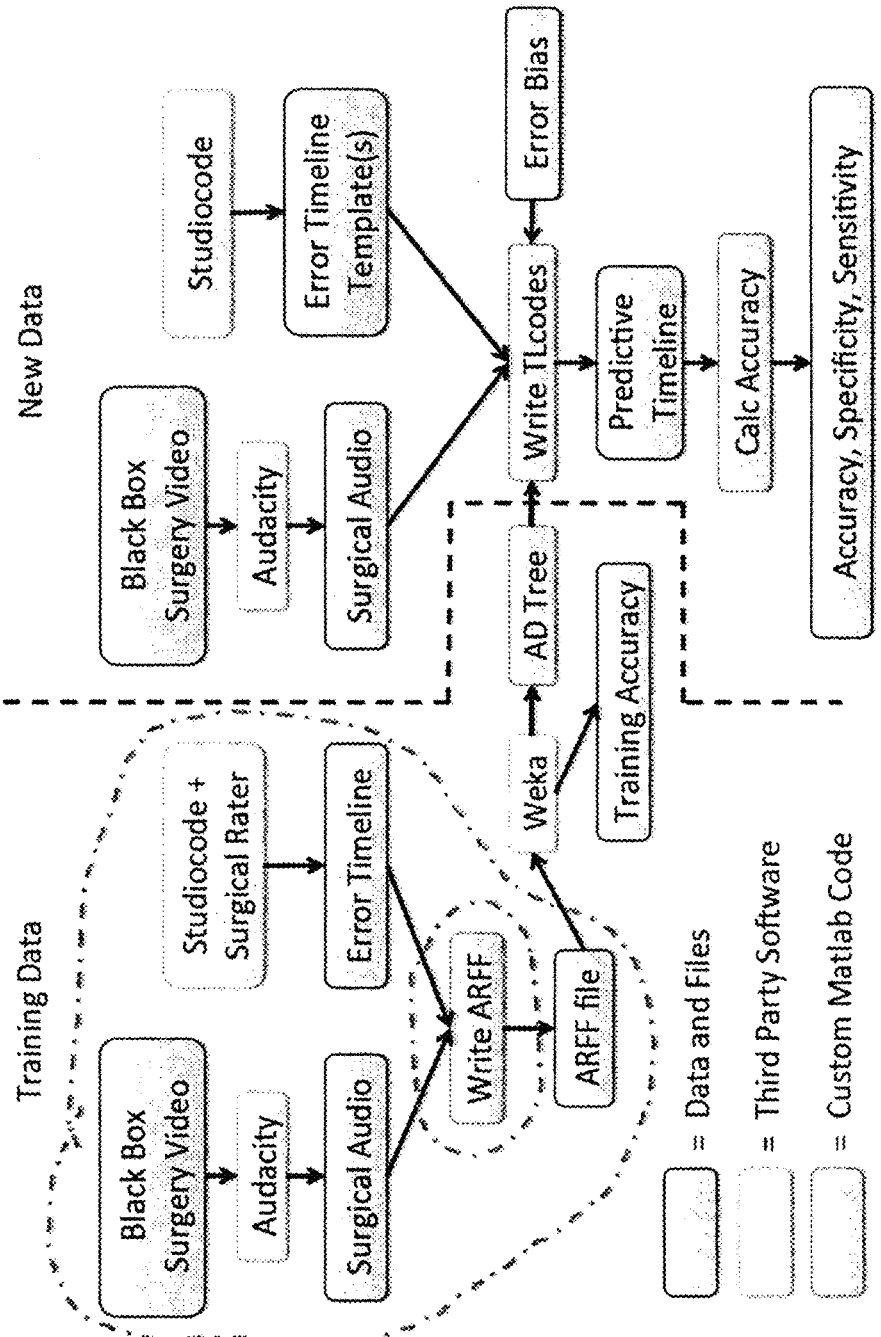
FIG. 21 is illustrative of a code workflow that may be utilized in conjunction with a perception engine 2000, according to some embodiments.

In some embodiments, the black box platform may be utilized in relation to tracked data in the context of an operating room. FIG. 21 is illustrative of a code workflow 2100 that may be utilized in conjunction with a perception engine 2000, according to some embodiments. Training data may be utilized to derive various templates that are used for automated decision making, and new data, as obtained from various sources, such as surgery videos, audio, sensory information, patient physiology information, etc. Various types of code, such as Matlab™ code, may be utilized iteratively to refine templates and hypothesized relationships between variables. Other types of programming languages and/or relational representations may be utilized.

For example, relationships may be stored in the form of attribute-relation file format files (ARFF), among others. Experimental data was recorded from 31 cases/surgeries that occurred between May 2015 and August 2015, and audio recordings were analyzed. 559 technical errors (e.g., where a surgeon made an error such as applying too much pressure to a patient's intestine) were tracked, where there were 207 technical events (e.g., where the pressure on a patient's intestine caused the intestine to rupture). Two lengths of recording clips were made, a first set at 30 seconds, and a second set at 30 seconds. Voice recordings were made 5 seconds before error and 25 seconds after error for 30 second recording clips, and made 10 seconds before the error and 50 seconds after the error for 60 second sound recording clips.

Features tracked in the sound recordings included: volume mean, standard deviation, volume dynamic range, average magnitude difference function (AMDF) mean/standard deviation, short time energy mean/standard deviation, spec centroid: mean and variance, spec roll: mean and variance, spec flux: mean and variance, zero crossings, and the first 5 Mel-frequency cepstral coefficients (MFCCs), 1 2 3 4 5.

Audio was extracted from multiple cases at once, and features were often extracted overnight. A software package was used for classification and attribute selection. Through experimentation, Applicants found that decision tree ensemble methods provided better accuracy and a 10-fold cross-validation. Table 1 is a table of audio info results:

|  | Audio Info | | | Training Accuracy (%) | |
|---|---|---|---|---|---|
| Tag | Pre Time | Post Time | AD Tree | Random Forest | Ensemble REP Tree |
| Errors | 5 | 25 | 56.0 | 58.8 | 59.4 |
|  | 10 | 50 | 58.1 | 63.1 | 62.0 |
|  | 20 | 40 | 59.3 | 65.1 | 61.4 |
|  | 30 | 60 | 62.3 | 67.3 | 64.2 |
|  | 30 | 30 | 59.6 | 65.1 | 62.8 |
| Events | 5 | 25 | 45.7 | 47.8 | 51.0 |
|  | 10 | 50 | 57.0 | 59.4 | 57.7 |

-continued

| | Audio Info | | | Training Accuracy (%) | |
|---|---|---|---|---|---|
| Tag | Pre Time | Post Time | AD Tree | Random Forest | Ensemble REP Tree |
| | 20 | 40 | 54.8 | 53.9 | 55.1 |
| | 30 | 60 | 50.5 | 57.5 | 56.0 |
| | 30 | 30 | 52.4 | 58.2 | 54.6 |

Features were removed, and experimental results indicated that for a removal of 7 features, a random forest approach yielded a rate of 63.059% to 64.9374% when 7 features were removed. An Alternating Decision (ADTree) approach yielded a rate of 58.05% to 58.67% when 8 features were removed.

As provided in the above results, Applicants noted that not all features were equally helpful in determining the presence of a clinical event. Accordingly, in some embodiments, the perception engine 2000 may be configured to remove various features from consideration, and in some further embodiments, the perception engine 2000 may be configured to automatically remove various features from consideration in view of an automated decision process wherein contributions are analyzed using statistical methods (e.g., p-test) and features below a particular contribution level are excluded. Such an approach may be advantageous especially where it is unclear as to which features are better or worse than others.

In an embodiment, tracked features include at least one of a volume standard deviation, a volume dynamic range, an AMDF mean, an AMDF standard deviation, a short time energy mean, a short time energy stand deviation, a spec centroid mean, a spec centroid variance, a spec roll variance, a spec flux mean, a spec flux variance, and a fifth mel-frequency cepstral coefficient.

In another embodiment, tracked features include at least one of a volume standard deviation, an AMDF mean, a short time energy mean, a spec centroid variance, a spec roll variance, and a spec flux variance. These specific features were found during experimentation to be particularly relevant.

The analysis may be re-run on various data sets to determine whether such removal was indeed beneficial from a perspective of increasing sensitivity and/or specificity. Applicants, through experimentation, found that some embodiments were particularly accurate in identifying clusters of clinical events (e.g., clusters of technical errors).

Figure 22:
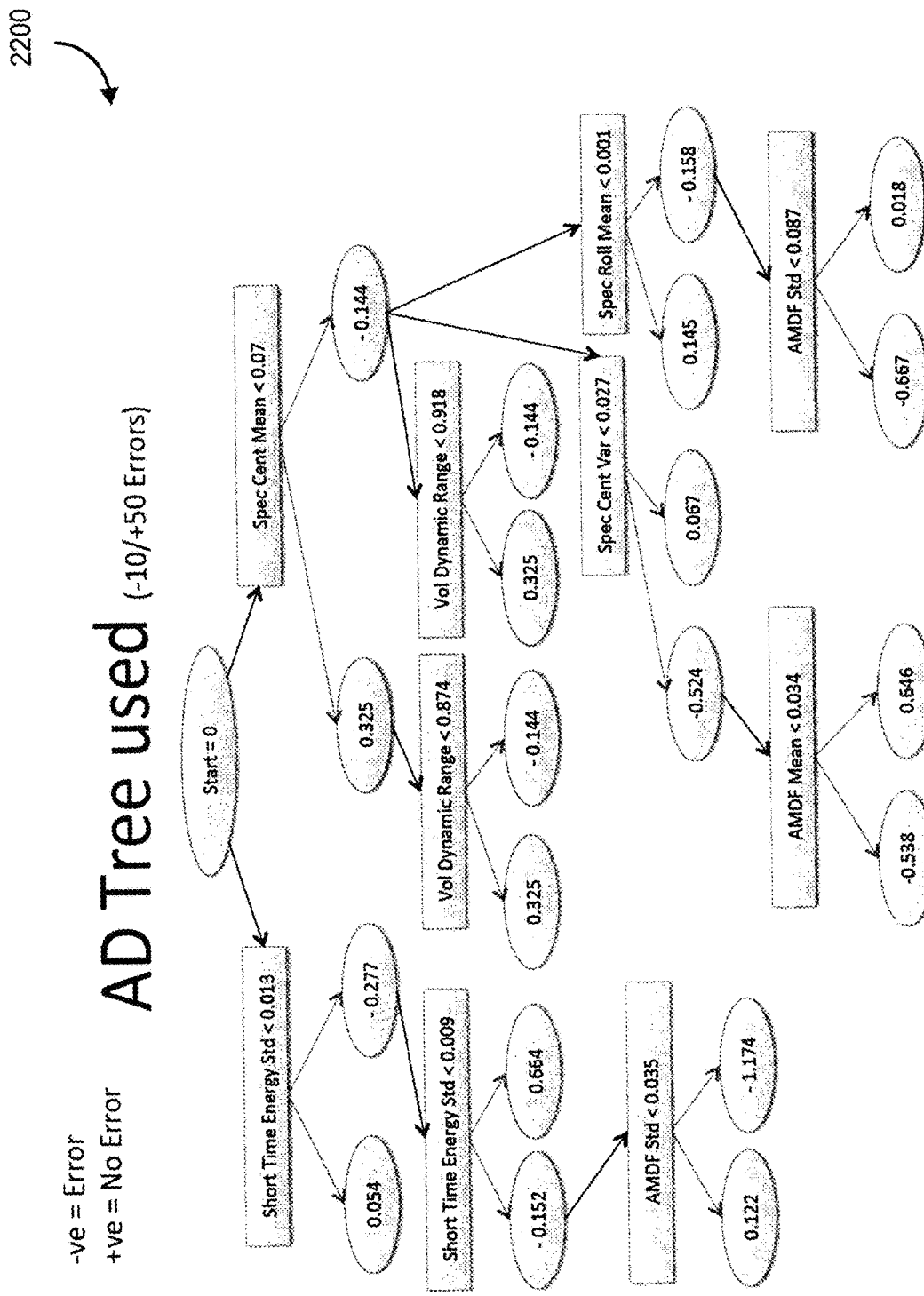
FIG. 22 is a sample AD tree, according to some embodiments.

An ADTree was found to have various benefits, such as being interpretable, easy to implement, providing an inherent way to 'control' sensitivity/specificity and being consistently one of the more accurate classifiers (e.g., it was found to be accurate in experimental iterations). FIG. 22 is a non-limiting example of an AD tree 2200, according to some embodiments.

In using an ADTree, the system is configured to find various conditions throughout an entire tree that minimizes a splitting criterion, for example, analyzing DKM instead of entropy, 2*sqrt(p(1−p)) instead of SUM (−p log 2p), concavity, among others.

Figure 23:
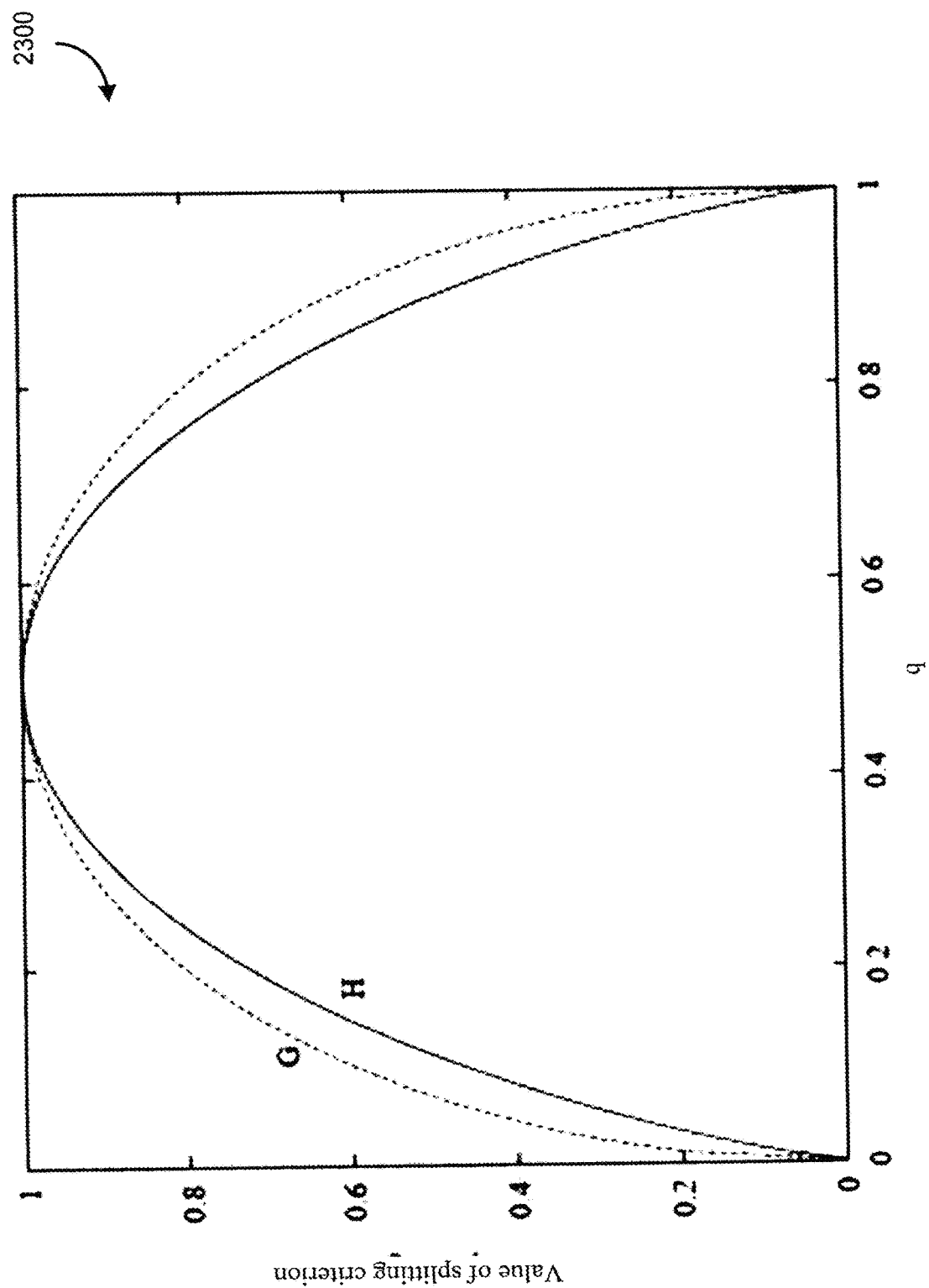
FIG. 23 is a comparison of G and H, according to some embodiments.

Scores may be found based on natural log of the ralo of +ve and −ve examples, for example, 0.5 In (positive/negative). Rules may be added to classifiers, and continued until an unspecified stopping criterion. FIG. 23 a graph 2300 of a comparison of G (DKM approach) and H (an information gain approach), according to some embodiments. As depicted in FIG. 23, there may be differing outcomes from using a DKM approach was compared to an information gain approach in determining which features to assess.

Prediction timelines were created with a ADTree algorithm and training data, and the process included extracting surgical audio, identifying features from specific cases' surgical audio, running features through an ADTree classifier, writing predicted times into a timeline, and copy and pasting a timeline into existing rated timeline to qualitatively compare results of prediction. In some embodiments, a ADTree threshold may be amended to modify and/or balance between sensitivity and/or specificity of the system. Table 2 is an example table illustrating some experimental results based on an embodiment.

| Case Number | ADTree Threshold | Accuracy (%) | Sensitivity (%) | Specificity (%) |
|---|---|---|---|---|
| 3103 | 0.0 | 76.0 | 12.0 | 86.6 |
| | 0.4 | 18.6 | 93.9 | 6.7 |
| 4070 | 0.0 | 79.2 | 0 | 95.2 |
| | 0.4 | 38.6 | 88.9 | 28.6 |
| 4245 | 0.0 | 88.0 | 33.3 | 96.7 |
| | 0.4 | 50.7 | 88.9 | 45.2 |
| 4977 | 0.0 | 81.8 | 24.3 | 96.0 |
| | 0.4 | 54.0 | 67.6 | 51.3 |
| 5443 | 0.0 | 78.9 | 0 | 88.5 |
| | 0.4 | 31.0 | 47.1 | 29.3 |

Figure 24:
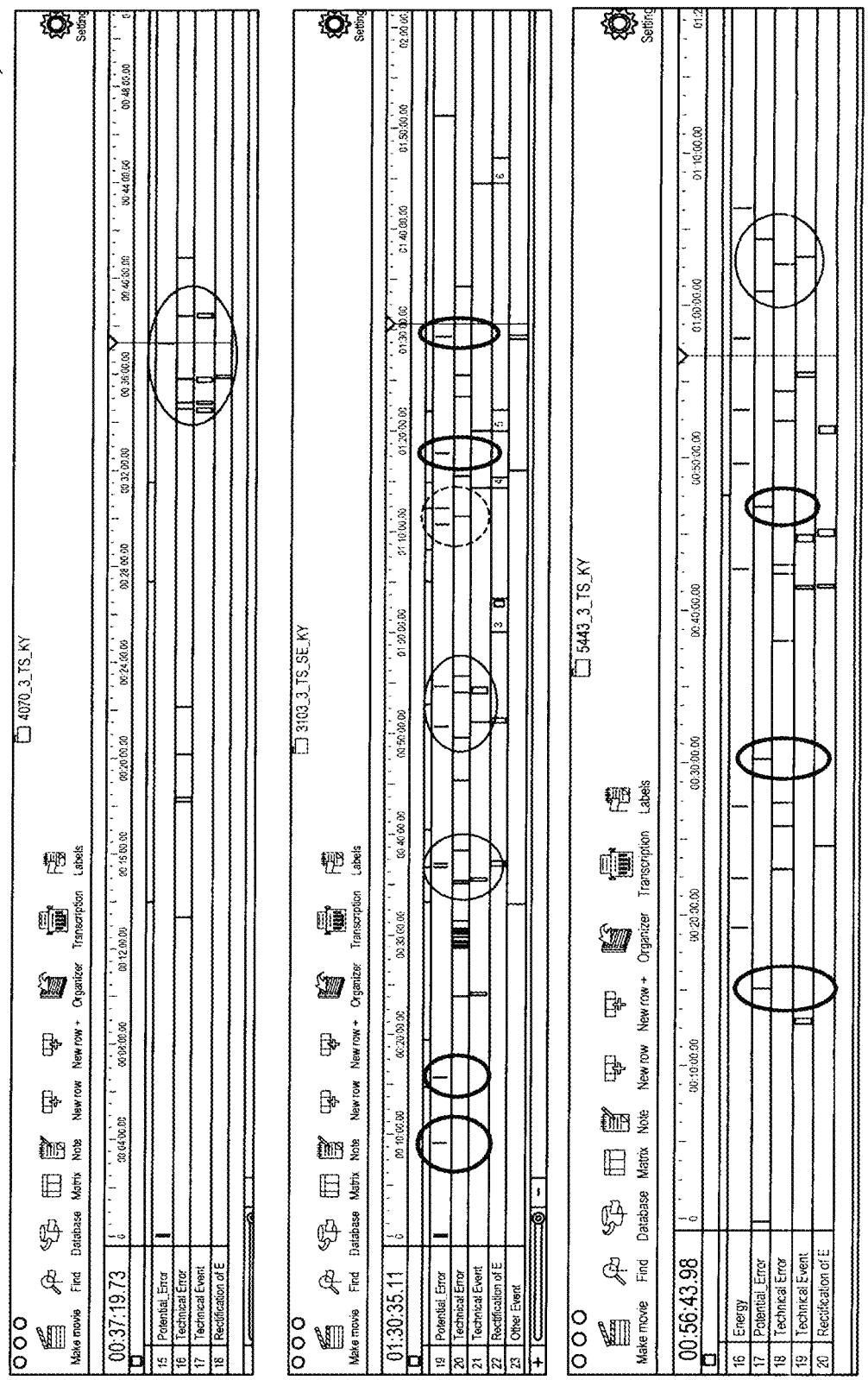
FIG. 24 is a timeline chart illustrative of some results where the system was unable to identify potential errors in relation to actual technical errors and/or technical events, according to some embodiments.

FIG. 24 is a timeline chart 2400 illustrative of some results where the system had difficulty identifying potential errors in relation to actual technical errors and/or technical events, according to some embodiments. The chart may be generated as part of a user interface with interface indicator elements for clinical events detected in the session container file.

Figure 25:
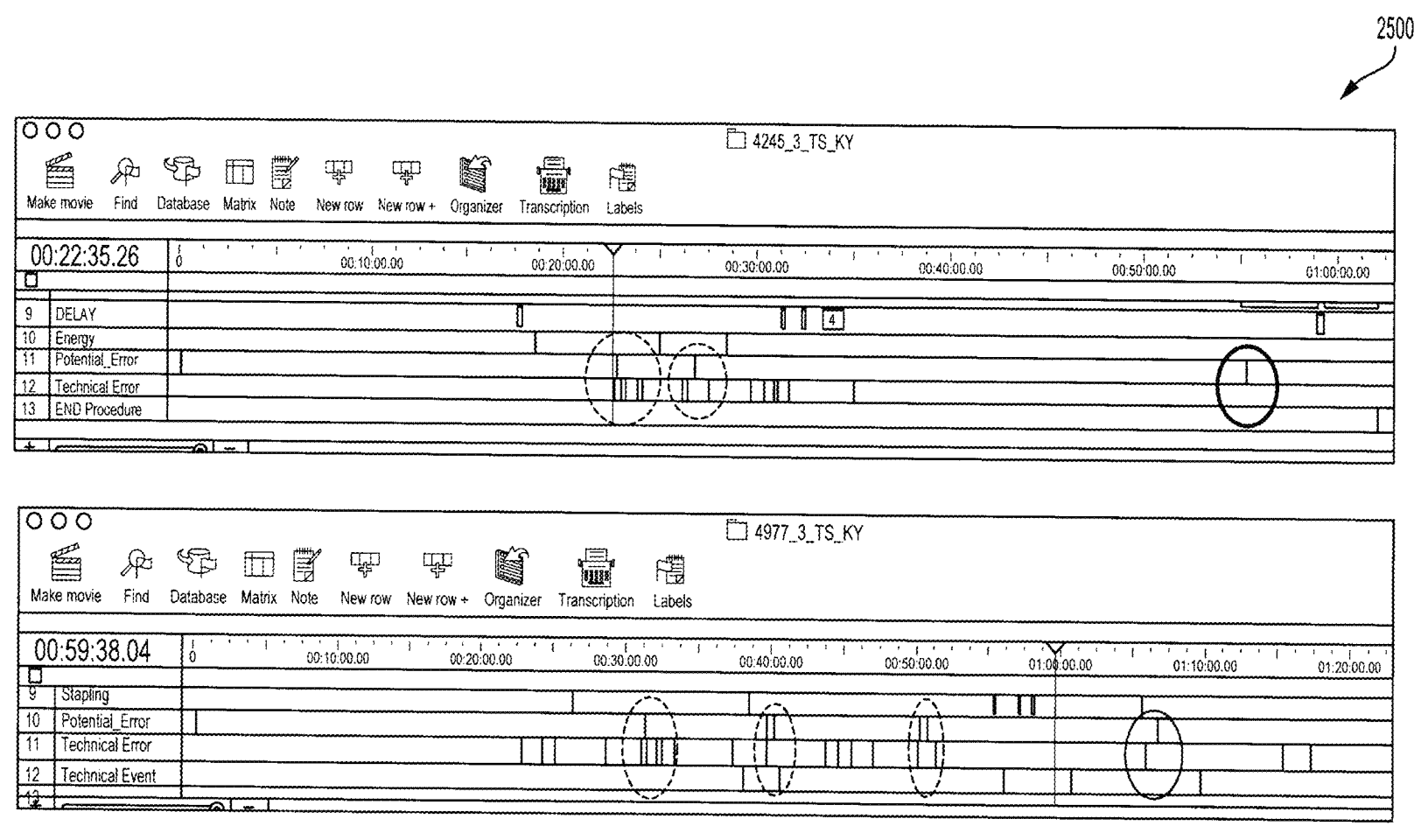

FIG. 25 is a timeline chart 2500 illustrative of some results where the system was able to identify potential errors in proximity to actual technical errors and/or technical events, according to some embodiments. The chart may be generated as part of a user interface with interface indicator elements for clinical events detected in the session container file.

As indicated in the results of FIG. 24 and FIG. 25, the analysis may be susceptible to the training and/or parameters of the machine-learning approach utilized.

The results however, may be indicative that the embodiment of the system was able to estimate some clinical events as noted as "potential errors" in proximity to actual technical errors, technical events as determined by surgical raters. The results further indicate that the system was more accurate when technical errors occurred in clusters. The removal of features may be particularly important where some of the features originally thought to be useful may actually be misleading and detrimentally impact the training of the system. For example, some features may be helpful from the perspective of providing useful splitting criterion, while other features may simply provide "bad data" where patterns cannot be ascertained.

As noted in FIGS. 24 and 25, there are some "potential errors" that were found to be false positives. In view of the operating environment of the black box system 1600, the perception engine 2000 may be tuned such that more false positives are tolerated, as long as true positives are also caught (e.g., a reduction of false positives). This may be particularly important for surgical or medical environments, where an uncaught clinical event may have significantly severe adverse outcomes. While false positives are also undesirable, they may at least be rectified on later review.

Figure 26:
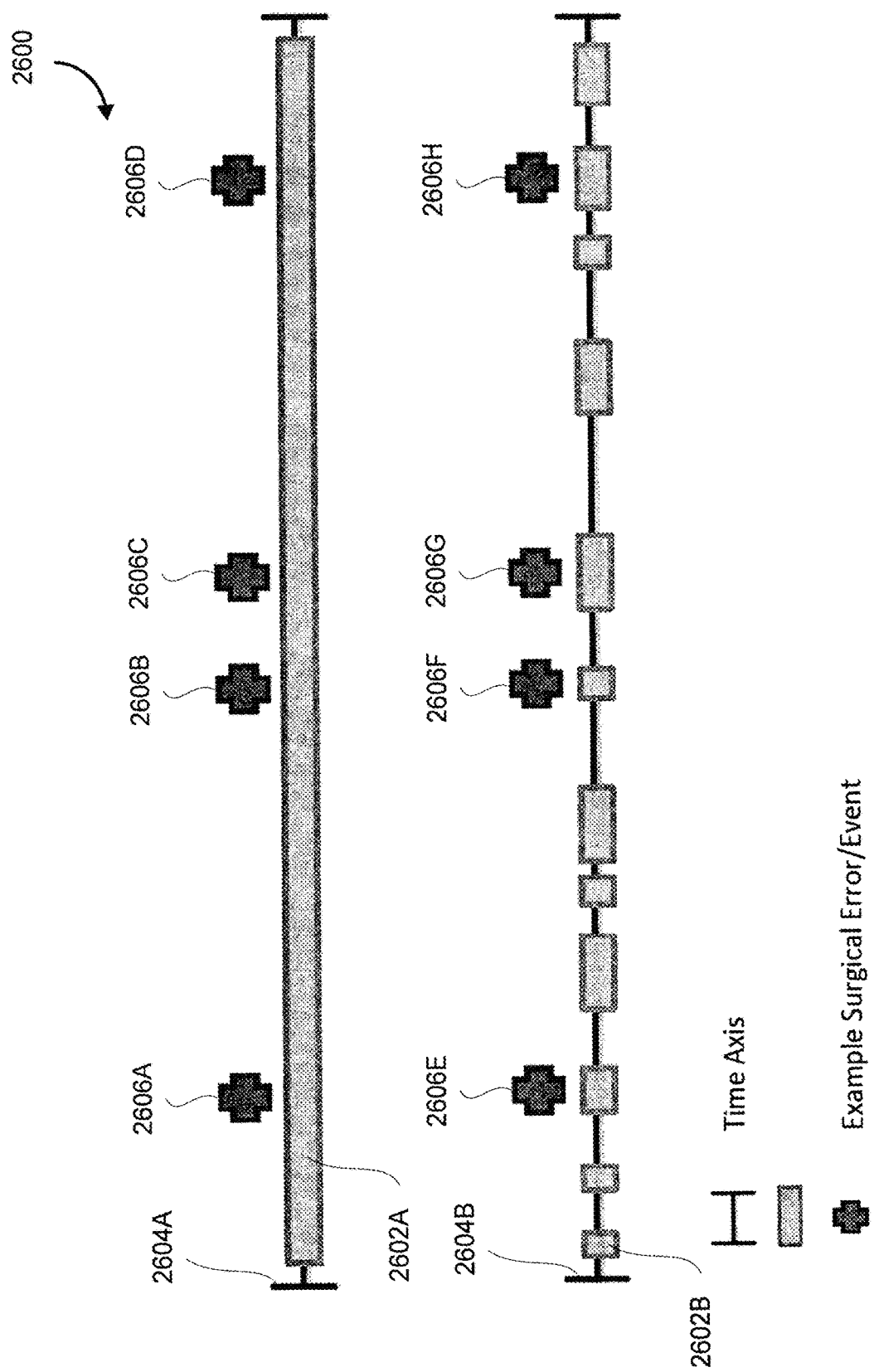
FIG. 26 is a timeline chart comparing a conventional method of reviewing surgical procedures compared to a proposed method of reviewing surgical procedures, according to some embodiments.

FIG. 26 is a timeline chart comparing a conventional method of reviewing surgical procedures compared to a proposed method of reviewing surgical procedures, according to some embodiments. The time in which a surgical procedure is monitored in the bars 2602A and 2602B, and the entirety of the timespan is provided in the lines 2604A and 2604B. The crosses 2606A-H are illustrative of example surgical errors and events. For example, audio may be cut into various slices, and for each audio section, the revisers may check whether there is an error prediction and whether there is an annotated error. Based on the feedback, an appropriated label may be applied (e.g., the alert is correct, a false alarm, etc.). This label may be re-fed into the perception engine 2000 so that the perception engine 2000 may modify and/or tailor various parameters for use in machine learning.

Applying the outputs of the perception engine 2000, the system may be able to generate notifications and/or other control commands indicative of the periods of time when a reviewer should be reviewing a surgical procedures, reducing the amount of time required from various human reviewers. As provided in 2602B, and 2604B the machine-learning approaches may be utilized to reduce the amount of time the surgical procedure should be reviewed (as indicated by the reduction of 2602B relative to 2602A into staggered portions of time).

For example, instruction sets may be utilized to generate notifications and/or other representations of when a particular surgical record may require validation. In some embodiments, the determinations of when the surgical record should require validation by a reviewer may be established through filtering the timeframe to include portions where the potential likelihood of a clinical event as determined by the perception engine 2000 is greater than a particular threshold (e.g., 20%, 40%, 60%, 80%, 85%, 90%, 100%, or percentages in between). Accordingly, the cost and expense allocated to review may be better focused on time periods in which a potential error may have occurred.

In some embodiments, confidence scores and/or levels may be indicated through visual means and/or representations, such as the use of colors to indicate differing confidence levels. For example, red may be indicative of higher levels of confidence about a clinical event, orange may be indicative of medium levels of confidence, and green may be indicative of low level of confidence.

Figure 27:
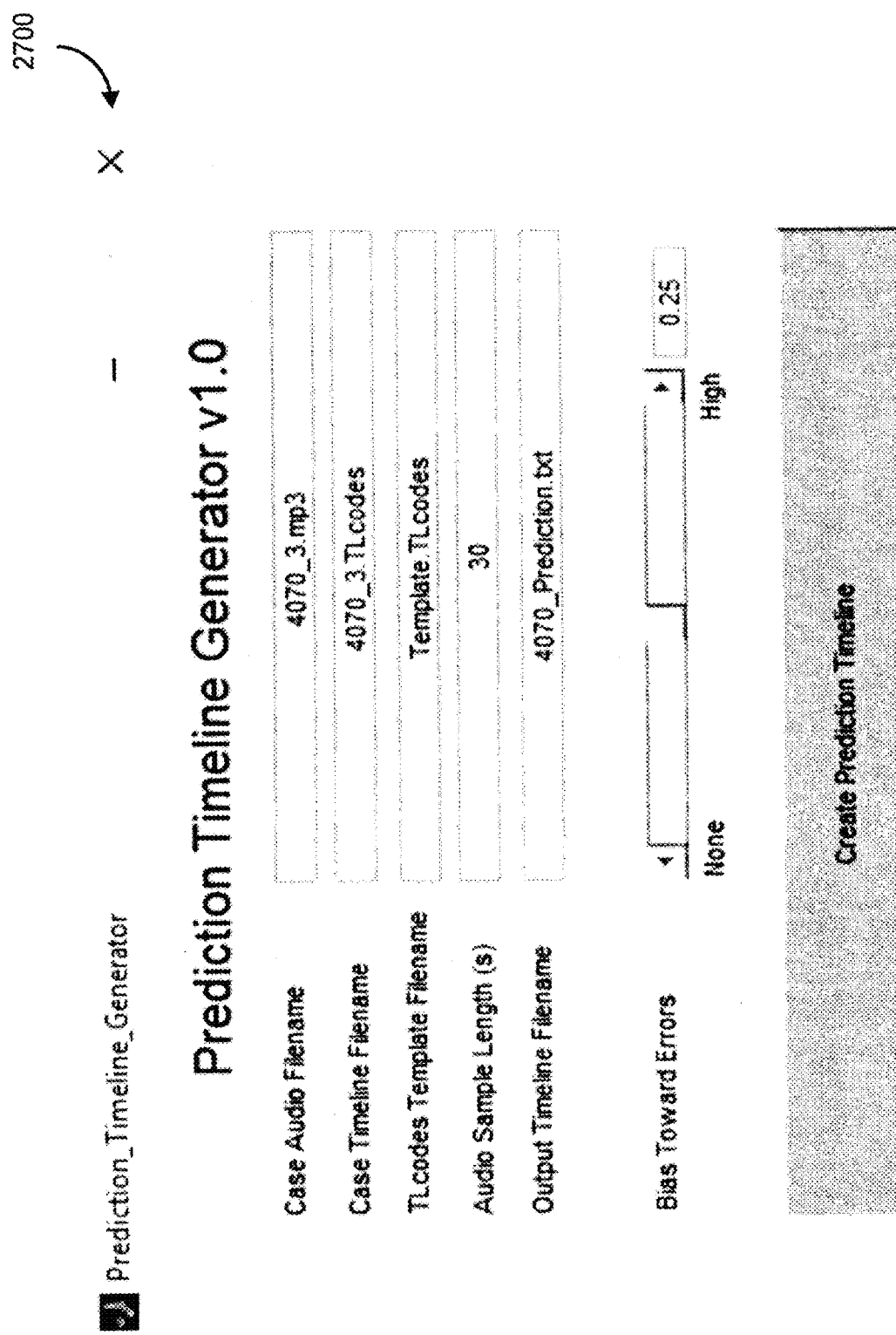
FIG. 27 is illustrative of a sample user interface, according to some embodiments.

FIG. 27 is illustrative of a sample user interface 2700, according to some embodiments.

Example to Predict Locations of Surgical Error in Timeline

In some embodiments, Matlab™ code may be utilized to predict locations of surgical error. While other types of code (e.g., Python™, LISP™, C™, Java™, Visual Basic™) may be utilized, the following is provided as an illustrative example. The Matlab™ code can be split into two parts. The first part of the code generates an Attribute-Relation File Format (.arff) file which can be used to generate a machine-learning algorithm. The second part of the code uses the machine learning algorithm generated in the first part to create a timeline with predicted locations of a surgical error to be provided to surgical raters to assist them with their ratings of various surgical procedures.

Generating an .arff file: The following steps are taken by the Matlab™ code to generate a .arff file: Matlab™ reads in an audio file, whose file name is specified by the user Matlab™ reads in a rated Timeline associated with the audio file, with technical error annotations specific to the audio file. Using the rated timeline, the Matlab™ code finds a timestamp of a surgical error, and cuts out an audio clip surrounding that timestamp from the larger audio.

The Matlab code extracts audio features from the smaller audio clip. The Matlab™ code prints the data about the audio clip into the .arff file. The Matlab™ code also labels the audio "yes", as in "yes, there is a surgical error in this audio clip". The Matlab™ code takes an audio clip from a random point in the audio not close to a surgical error annotation, and repeats steps 4-5 for that audio clip. The audio clip is labelled "no" since this audio clip has no surgical error in it. The Matlab code repeats the steps for all rated surgical errors and all surgical audios specified by the user.

The end result is an .arff file with a library of audio clips both associated with and not associated with a surgical error, with the numerical values of the audio features for each audio clip.

Generating a machine learning algorithm: The .arff file may be used by the hardware engine configured to generate decision trees to generate an Alternating Decision Tree (ADTree). This ADTree is converted from the output into a Matlab function, which takes the features of an audio clip as inputs, and outputs a prediction: whether the audio clip has a surgical error associated with it or not.

Generating a timeline with predicted error timestamps: Using the ADTree, Matlab™ then generates a file with annotations where the ADTree predicts there might be a surgical error. Matlab™ may be configured to utilize the following steps to do so:

Matlab™ reads in an unrated surgical audio file and the empty studiocode .TLCodes file associated with the audio. Matlab™ extracts relevant data, such as the video file location, from the empty studiocode .TLCodes file. Matlab segments the audio file into smaller pieces, whose length is specified by the user. For each audio segment, Matlab extracts features for that audio and runs the data through the alternating decision tree. Matlab keeps track of the timestamps where the ADTree predicts that a surgical error has occurred. Using the information from step 2 and step 4, Matlab™ writes the data into a pre-built .TLCodes template file. The end result is a studiocode .TLCodes file that, when opened, will produce the video associated with the audio file, as well as a timeline with locations of predicted errors.

This can be used by surgical raters to assist them with their surgical ratings.

A user interface may be provided where a user can specify an audio filename, TLCodes filename, TLCodes template filename, desired audio sample length, desired output filename, and a desired bias towards predicting errors, among others. After this, the user can click the "Create prediction timeline" button and a predictive timeline will generate in the same folder as the surgical audio.

Educational Strategies Generated Using the Black Box Data

Embodiments described herein may implement educational interventions based on OR black box performance analysis. For example, embodiments may provide training solutions or provide output data files that may be used to generate training solutions.

The data obtained from the systematic analysis of operative procedures may provide insight into the complex processes within the healthcare system, allow assessment of performance on an individual and team level, and evaluate human interactions with modern technology. Furthermore, this data can be used to determine specific individual and team performance deficiencies, hazard zones within procedures as well as characterize the cascade of events that result in "near misses" or adverse patient outcomes. This information may deliver critical knowledge content required to tailor effective educational interventions based on real life observations rather than hypothetical scenarios used in current training. This concept, grounded in theory of experiential learning may be used to create generalizable educational strategies that can be packaged and delivered to sites that do not have access to their own real-life data.

All training interventions may be tested using rigorous research methodology to generate a set of validated training solutions rooted in real observation.

The educational interventions may employ diverse instructional strategies such as team debriefing, individual and team coaching, error awareness and mitigation training, behavior modeling and warm-up simulation training.

Embodiments described herein may provide identification of root-causes of adverse outcomes and design of training scenarios. By way of example, the cause of adverse patient outcomes may remain elusive as they are frequently multifactorial and based on retrospective analysis. Embodiments described herein with black box generated data may allow analysis of prospectively documented adverse outcomes. Patterns of recurrent problems may be identified, characterized and used to generate a set of scenarios based on real experiences. This knowledge may be relevant to all OR teams involved in patient treatment in similar clinical contexts. The educational content may be compiled and delivered to information sheets, textbooks, e-learning software, virtual-reality simulation tools and software as well as integrated into SOPs at an institutional level.

Beyond summarizing common or significant root-causes of adverse outcomes, these scenarios may be used to generate software packages for full-scale simulations in virtual OR's. The variables can be programmed into the simulation software and thus be packaged, commercialized and exported to educational institutions worldwide.

Embodiments described herein may provide technical analysis to determine error frequencies, distribution and hazard zones. For example, the end-user of this data may be practicing physicians/surgeons and trainees. Mapping procedure complexity and identifying potential hazard zones can be used to create educational strategies targeted directly at these steps. Instructional strategies such as deliberate practice can then be used to train surgeons to be better prepared for these steps and thus minimize the risk of adverse events. Informing surgeons about complex or hazardous steps also enables the design of SOPs (such as in aviation for example with the "sterile" cockpit concept during takeoff and landing), to limit distractions during these sensitive steps (no irrelevant conversation, minimize room traffic, reduce overall noise).

Embodiments described herein may provide identification of beneficial and detrimental team interactions, and design and validation of simulated team training scenarios.

The functioning of the team may be influenced by non-technical skills such as communication. Non-technical skills have also been linked to patient outcome. Therefore, recognition of specific behavior patterns within teams that are either beneficial or detrimental to patient outcome is a step that may be required to subsequently fashion specific team training interventions and debriefing sessions. The core will thus use the data generated through the OR black box observations to identify specific patterns in non-technical performance of the teams. This information may serve as the basis for design specific team interventions using OR simulations, role-play and debriefing sessions. Recurrent themes that are identified as affecting team performance on an organizational level may be addressed by policy recommendations and the design of SOPs.

The end user of this data may be all inter-professional OR teams. Educational interventions derived from the black box data will be designed as a teaching package for interdisciplinary team training. Behavior patterns identified to cause disruptions in organizational processes will be addressed by policy changes at local and regional level.

Embodiments described herein may contribute to improvements over current and/or previous designs. For example, embodiments described herein may provide scalability. Additional devices can be added to the configuration without excessive and costly hardware and cabling. As another example, embodiments described herein may provide optimization. They may be an improved ability to address varied physical spaces and add additional capture zones for wider range of event chains. As a further example, embodiments described herein may provide increased content with a greater ability to add additional data types for richer content. As an additional example, embodiments described herein may provide improved synchronization for devices with a reduced reliance on expensive hardware encoders, increased accuracy, and reduced exposure to latency. Embodiments described herein may provide greater leverage of general purpose computing equipment and reduced overall platform cost.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, routers, portals, platforms, or other systems formed from computing device hardware. The computing devices may have at least one processor configured to execute software instructions stored on a computer readable tangible, non-transitory medium. For example, a server can include one or more computers operating as a web server, database server, or other type of computer server in a manner to fulfill described roles, responsibilities, or functions.

The description provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

Although the embodiments have been described in detail, it should be understood that various changes, substitutions and alterations can be made herein in different embodiments.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized.

As can be understood, the examples described above and illustrated are intended to be exemplary only.

The invention claimed is:

1. A computer implemented system for automatically processing audio-visual recordings of one or more surgical procedures to automatically generate data structures representing durations of time where predicted errors are estimated to augment rendering of a surgical decision support graphical user interface associating digital recordings of one or more surgical procedures with the predicted errors based on predictions generated by an artificial neural network, the system comprising:
   a plurality of hardware units for collecting real-time medical or surgical data streams having a control interface coupled by a network to cameras, sensors, audio devices, and patient monitoring hardware, the real-time medical or surgical data streams relating to a real-time medical procedure within an operating or clinical site;
   an encoder for synchronizing and recording the real-time medical or surgical data streams to a common clock or timeline to generate a session container data structure storing at least one of video or audio data streams;
   a processor, coupled with a non-transitory computer-readable memory maintaining a trained predictive data model, the processor configured to:
      identify, using the trained predictive data model, one or more potential time-stamped clinical error events within the session container data structure;
      generate a time-synchronized metadata track representing timestamp markers corresponding to specific timestamps or timestamp ranges of the durations of time corresponding to the at least one of video or audio data streams of the session container data structure, each timestamp marker of the timestamp markers corresponding to a specific time-stamped potential clinical error event;
      train the predictive data model using reviewer validation inputs representing one or more labels corresponding to at least one of the time-stamped potential clinical error events, the one or more labels each indicating whether the corresponding time-stamped potential clinical error event was correct or false; and
      control rendering of the surgical decision support graphical user interface by overlaying a visual rendering of the time-synchronized metadata track upon a rendering of a timeline chart, one or more interactive visual interface elements, each interactive visual interface element corresponding to the corresponding specific time-stamped potential clinical error event.

2. The computer implemented system of claim 1, wherein the surgical decision support graphical user interface is configured to receive the reviewer validation inputs representing one or more labels, each label of the one or more labels indicating whether an alert corresponding to the specific time-stamped potential clinical error event is a correct alarm or a false alarm.

3. The computer implemented system of claim 1, wherein the surgical decision support graphical user interface is configured to render only the timestamp markers corresponding to a specific time-stamped potential clinical error event where the corresponding specific time-stamped potential clinical error event has an associated confidence level greater than a pre-defined threshold.

4. The computer implemented system of claim 1, wherein the surgical decision support graphical user interface is configured to render the timestamp markers corresponding to a specific time-stamped potential clinical error event with different colors based on threshold ranges indicative of a range of an associated confidence level.

5. The computer implemented system of claim 1, wherein the trained predictive data model is maintained within one or more attribute-relation file format files.

6. The computer implemented system of claim 5, wherein the one or more attribute-relation file format files are utilized to instantiate the trained predictive data model, which is then used to process a recording to generate the time-synchronized metadata track and to identify the specific time-stamped potential clinical error event.

7. The computer implemented system of claim 6, wherein upon identifying the specific time-stamped potential clinical error event using the trained predictive data model, a random time point in a media clip not proximate to any specific time-stamped potential clinical error event is selected and the trained predictive data model is run again on the random time point to identify an example time point with no surgical error.

8. The computer implemented system of claim 7, wherein a final output session container data structure is generated from the session container data structure, storing the one or more attribute-relation file format files alongside one or more media clips both associated with and not associated with a surgical error.

9. The computer implemented system of claim 8, wherein for each of the one or more media clips, one or more numerical representations are maintained, each associated with one or more features of the one or more media clips.

10. The computer implemented system of claim 1, wherein the predictive data model is tuned to tolerate an increased number of false positive predictions.

11. A computer implemented method for automatically processing audio-visual recordings of one or more surgical procedures to automatically generate data structures representing durations of time where predicted errors are estimated to augment rendering of a surgical decision support graphical user interface associating digital recordings of one or more surgical procedures with the predicted errors based on predictions generated by an artificial neural network, the method comprising:

collecting real-time medical or surgical data streams having a control interface coupled by a network to cameras, sensors, audio devices, and patient monitoring hardware, the real-time medical or surgical data streams relating to a real-time medical procedure within an operating or clinical sit;

synchronizing and recording the real-time medical or surgical data streams to a common clock or timeline to generate a session container data structure storing at least one of video or audio data streams;

maintaining a trained predictive data model;

identifying, using the trained predictive data model, one or more potential time-stamped clinical error events within the session container data structure;

generating a time-synchronized metadata track representing timestamp markers corresponding to specific timestamps or timestamp ranges of the durations of time corresponding to the at least one of video or audio data streams of the session container data structure, each timestamp marker of the timestamp markers corresponding to a specific time-stamped potential clinical error event and including a data field representing the associated confidence level;

training the predictive data model using reviewer validation inputs representing one or more labels corresponding to at least one of the time-stamped potential clinical error events, the one or more labels each indicating whether the corresponding time-stamped potential clinical error event was correct or false; and controlling rendering of the surgical decision support graphical user interface by overlaying a visual rendering of the time-synchronized metadata track upon a rendering of a timeline chart, one or more interactive visual interface elements, each interactive visual interface element corresponding to the corresponding specific time-stamped potential clinical error event.

12. The computer implemented method of claim 11, wherein the surgical decision support graphical user interface is configured to receive the reviewer validation inputs representing the one or more labels, each label of the one or more labels indicating whether an alert corresponding to the specific time-stamped potential clinical error event is a correct alarm or a false alarm.

13. The computer implemented method of claim 11, wherein the surgical decision support graphical user interface is configured to render only the timestamp markers corresponding to a specific time-stamped potential clinical error event where the corresponding specific time-stamped potential clinical error event has an associated confidence level greater than a pre-defined threshold.

14. The computer implemented method of claim 11, wherein the surgical decision support graphical user interface is configured to render the timestamp markers corresponding to a specific time-stamped potential clinical error event with different colors based on threshold ranges indicative of a range of an associated confidence level.

15. The computer implemented method of claim 11, wherein the predictive data model is maintained within one or more attribute-relation file format files.

16. The computer implemented method of claim 15, wherein the one or more attribute-relation file format files are utilized to instantiate the trained predictive data model, which is then used to process a recording to generate the time-synchronized metadata track and to identify the specific time-stamped potential clinical error event.

17. The computer implemented method of claim 16, wherein upon identifying the specific time-stamped potential clinical error event using the trained predictive data model, a random time point in a media clip not proximate to any specific time-stamped potential clinical error event is selected and the trained predictive data model is run again on the random time point to identify an example time point with no surgical error.

18. The computer implemented method of claim 17, wherein a final output session container data structure is generated from the session container data structure, storing the one or more attribute-relation file format files alongside one or more media clips both associated with and not associated with a surgical error.

19. The computer implemented method of claim 18, wherein for each of the one or more media clips, one or more numerical representations are maintained, each associated with one or more features of the one or more media clips.

20. A non-transitory computer readable medium, storing machine interpretable instruction sets, which when executed by a processor, cause the processor to perform a computer implemented method for automatically processing audio-visual recordings of one or more surgical procedures to automatically generate data structures representing durations of time where predicted errors are estimated to augment rendering of a surgical decision support graphical user interface associating digital recordings of one or more surgical procedures with the predicted errors based on predictions generated by an artificial neural network, the method comprising:

collecting real-time medical or surgical data streams having a control interface coupled by a network to cameras, sensors, audio devices, and patient monitoring hardware, the real-time medical or surgical data streams relating to a real-time medical procedure within an operating or clinical site;

synchronizing and recording the real-time medical or surgical data streams to a common clock or timeline to generate a session container data structure storing at least one of video or audio data streams;

maintaining a trained predictive data model;

identifying, using the trained predictive data model, one or more potential time-stamped clinical error events within the session container data structure;

generating a time-synchronized metadata track representing timestamp markers corresponding to specific timestamps or timestamp ranges of the durations of time corresponding to the at least one of video or audio data streams of the session container data structure, each timestamp marker of the timestamp markers corresponding to a specific time-stamped potential clinical error event;

training the predictive data model using reviewer validation inputs representing one or more labels corresponding to at least one of the time-stamped potential clinical error events, the one or more labels each indicating whether the corresponding time-stamped potential clinical error event was correct or false; and controlling rendering of the surgical decision support graphical user interface by overlaying a visual rendering of the time-synchronized metadata track upon a rendering of a timeline chart, one or more interactive visual interface elements, each interactive visual interface element corresponding the corresponding specific time-stamped potential clinical error event.

* * * * *